(12) United States Patent
Yu et al.

(10) Patent No.: US 11,958,830 B2
(45) Date of Patent: Apr. 16, 2024

(54) PROTEASE INHIBITORS, PREPARATION, AND USES THEREOF

(71) Applicant: WESTLAKE PHARMACEUTICALS (HANGZHOU) CO., LTD., Hangzhou (CN)

(72) Inventors: Hongtao Yu, Hangzhou (CN); Qi Hu, Hangzhou (CN); Jing Huang, Hangzhou (CN); Tingliang Wang, Hangzhou (CN); Ningke Hou, Hangzhou (CN); Lijing Zhang, Hangzhou (CN); Wenyi Zhang, Hangzhou (CN); Qiaozhu Tan, Hangzhou (CN)

(73) Assignee: WESTLAKE PHARMACEUTICALS (HANGZHOU) CO., LTD., Hangzhou (CN)

(*) Notice: Subject to any disclaimer, the term of this patent is extended or adjusted under 35 U.S.C. 154(b) by 28 days.

(21) Appl. No.: 17/215,313

(22) Filed: Mar. 29, 2021

(65) Prior Publication Data

US 2022/0227731 A1    Jul. 21, 2022

(30) Foreign Application Priority Data

Jan. 12, 2021 (WO) ................ PCT/CN2021/071256

(51) Int. Cl.
| | | |
|---|---|---|
| C07D 401/06 | (2006.01) | |
| C07D 217/26 | (2006.01) | |
| C07D 401/12 | (2006.01) | |
| C07D 471/10 | (2006.01) | |
| C07D 491/044 | (2006.01) | |

(52) U.S. Cl.
CPC ......... *C07D 401/06* (2013.01); *C07D 217/26* (2013.01); *C07D 401/12* (2013.01); *C07D 471/10* (2013.01); *C07D 491/044* (2013.01)

(58) Field of Classification Search
None
See application file for complete search history.

(56) References Cited

U.S. PATENT DOCUMENTS

| 6,335,350 B1 | 1/2002 | Bloom et al. |
| 7,732,446 B1 | 6/2010 | Gwaltney et al. |
| 2004/0259910 A1 | 12/2004 | Bolin et al. |
| 2005/0020644 A1 | 1/2005 | Bisaha et al. |
| 2014/0343036 A1 | 11/2014 | Chen et al. |
| 2015/0105393 A1 | 4/2015 | Yamagishi et al. |
| 2018/0282317 A1 | 10/2018 | Lin et al. |

FOREIGN PATENT DOCUMENTS

| CN | 1642940 A | 7/2005 |
| CN | 1791581 A | 6/2006 |
| CN | 104334532 A | 2/2015 |
| CN | 104364235 A | 2/2015 |
| CN | 107674029 A | 2/2018 |
| CN | 108351169 A | 7/2018 |
| WO | WO2013113669 | 8/2013 |
| WO | WO2014025651 A1 | 2/2014 |
| WO | WO2015034271 A1 | 3/2015 |
| WO | WO2016036638 A1 | 3/2016 |
| WO | WO2017053604 | 3/2017 |
| WO | WO2018002848 A1 | 1/2018 |
| WO | WO2020065613 A1 | 4/2020 |

OTHER PUBLICATIONS

Database Registry Chemical Abstracts Service, Columbus, Ohio, Accession No. RN 1367763-60-7, Entered STN: Apr. 13, 2012.*
Database Registry [Online] Chemical Abstracts Service; Jun. 18, 2020, retrieved from STN; Database accession Nos. 2427843-20-5 and others, 46 pages.
Emsley et al., "Features and development of Coot," Acta Crystallogr D Biol Crystallogr, 2010, 66(Pt 4):486-501.
Fehr et al., "Coronaviruses: an overview of their replication and pathogenesis," Methods Mol Biol, 2015, 1282:1-23.
Lei et al., "Nsp3 of coronaviruses: Structures and functions of a large multi-domain protein," Antiviral Res, 2018, 149:58-74.
Liebschner et al., "Macromolecular structure determination using X-rays, neutrons and electrons: recent developments in Phenix," Acta Crystallogr D Struct Biol, 2019, 75(Pt 10):861-877.
McCoy et al., "Phaser crystallographic software," J Appl Crystallogr, 2007, 40(Pt 4):658-674.
Pillaiyar et al., "An Overview of Severe Acute Respiratory Syndrome-Coronavirus (SARS-CoV) 3CL Protease Inhibitors: Peptidomimetics and Small Molecule Chemotherapy," J Med Chem, 2016, 59(14): 6595-6628.
Wang et al., σ-Hole Bond vs π-Hole Bond: A Comparison Based on Halogen Bond. Chem Rev, 2016, 116(9):5072-5104.
Xie et al., "A nanoluciferase SARS-CoV-2 for rapid neutralization testing and screening of anti-infective drugs for COVID-19," Nat Commun, 2020, 11(1): 5214, 11 pages.

(Continued)

*Primary Examiner* — Samantha L Shterengarts
(74) *Attorney, Agent, or Firm* — FINNEGAN, HENDERSON, FARABOW, GARRETT & DUNNER LLP

(57) ABSTRACT

The disclosure provides at compounds of Formula I, compositions comprising the same, and methods of using the same, including use in treating a disease and/or a symptom of a disease caused by a coronavirus.

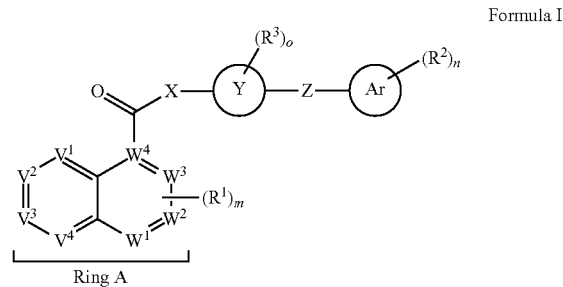

Formula I

40 Claims, 17 Drawing Sheets

Specification includes a Sequence Listing.

(56) References Cited

OTHER PUBLICATIONS

Xue et al., "Production of authentic SARS-CoV M(pro) with enhanced activity: application as a novel tag-cleavage endopeptidase for protein overproduction," J Mol Biol, 2007, 366(3):965-975.
Zhou et al., "A pneumonia outbreak associated with a new coronavirus of probable bat origin," Nature, 2020, 579:270-273.
Dai et al., "Synthesis of 3-Substituted 4-Aroylisoquinolines via Pd-Catalyzed Carbonylative Cyclization of o-(1-Alkynyl)benzaldimines", *Org. Lett*, 4, 193-196 (2002).
Saari et al., "Microwave-assisted synthesis of quinoline, isoquinoline, quinoxaline and quinazoline derivatives as CB2 receptor agonists", *Bioorg. & Med. Chem.*, 19, 939-950 (2011).
Abdusalam et al., "Identification of Potential Inhibitors of 3CL Protease of SARS-CoV-2 From ZINC Database by Molecular Docking-Based Virtual Screening", *Front. Mol. Biosci.*, 7, 603037 (2020).
Theerawatanasirikul et al., "Structural-based virtual screening and in vitro assays for small molecules inhibiting the feline coronavirus 3CL protease as a surrogate platform for coronaviruses", *Antiviral Res.*, 182, 104927 (2020).
Liu et al., "The development of Coronavirus 3C-Like protease (3CLpro) inhibitors from 2010 to 2020", *Eur J Med Chem*, 206, 112711 (2020).
Extended European Search Report for EP21165625.1, dated Sep. 16, 2021.

\* cited by examiner

| Compound No. | Structure |
|---|---|
| 2 | 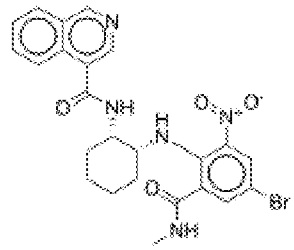 |
| 1 | 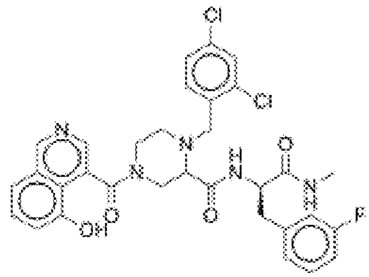 |
| 8 | 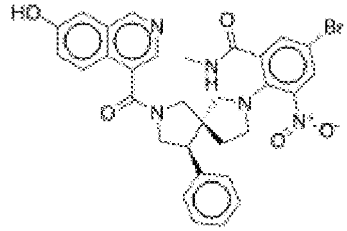 |

| Compound No. | Structure |
|---|---|
| 10 | 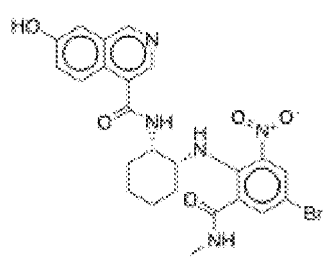 |
| 23 | 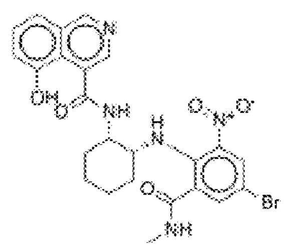 |

```
                              10         20         30         40         50         60         70
SARS-CoV2_3C..._009725301.1   SGFRKMAFPSGKVEGCMVQVTCGTTTLNGLWLDDVVYCPRHVICTSEDMLNPNYEDLLIRKSNHNFLVQ-  69
SARS-CoV_NP_828863.1          SGFRKMAFPSGKVEGCMVQVTCGTTTLNGLWLDDTVYCPRHVICTAEDMLNPNYEDLLIRKSNHSFLVQ-  69
MERS_YP_009047217             GGLVKMSHPSGDVEACMVQVTCGSMTLNGLWLDNTVWCPRHVMCPADQLSDPNYDALLISMTNHSFSVQK  70
                                                                     ▲          ▲

80         90        100        110        120        130        140
SARS-CoV2_3C..._009725301.1   --AGNVQLRVIGHSMQNCVLKLKVDTANPKTPKYKFVRIQPGQTFSVLACYNGSPSGVYQCAMRPNFTIK  137
SARS-CoV_NP_828863.1          --AGNVQLRVIGHSMQNCLLRLKVDTSNPKTPKYKFVRIQPGQTFSVLACYNGSPSGVYQCAMRPNHTIK  137
MERS_YP_009047217             HIGAPANLRVVGHAMQGTLLKLTVDVANPSTPAYTFTTVKPGAAFSVLACYNGRPTGTFTVVMRPNYTIK  140

150        160        170        180        190        200        210
SARS-CoV2_3C..._009725301.1   GSFLNGSCGSVGFNIDYDCVSFCYMHHMELPTGVHAGTDLEGNFYGPFVDRQTAQAAGTDTTITVNVLAW  207
SARS-CoV_NP_828863.1          GSFLNGSCGSVGFNIDYDCVSFCYMHHMELPTGVHAGTDLEGKFYGPFVDRQTAQAAGTDTTITLNVLAW  207
MERS_YP_009047217             GSFLCGSCGSVGYTKEGSVINFCYMHQMELANGTHTGSAFDGTMYGAFMDKQVHQVQLTDKYCSVNVVAW  210
                              ▲▲▲▲▲▲            ▲▲▲▲ ▲   ▲              ▲▲▲▲▲ ▲

220        230        240        250        260        270        280
SARS-CoV2_3C..._009725301.1   NY-EPLTQDHVDILGPLSAQTGIAVLDMCASLKELLQNGMNGRTILGSALLEDEFTPFDVVRQCSGVTFQ  276
SARS-CoV_NP_828863.1          NY-EPLTQDHVDILGPLSAQTGIAVLDMCAALKELLQNGMNGRTILGSTILEDEFTPFDVVRQCSGVTFQ  276
MERS_YP_009047217             QFTEFVGTQSVDM---LAVKTGVAIEQLLYAIQQLY-TGFQGKQILGSTMLEDEFTPEDVNMQIMGVVMQ  276

290        300        310
SARS-CoV2_3C..._009725301.1   NGRTILGSALLEDEFTPFDVVRQCSGVTFQ  306
SARS-CoV_NP_828863.1          NGRTILGSTILEDEFTPFDVVRQCSGVTFQ  306
MERS_YP_009047217             QGKQILGSTMLEDEFTPEDVNMQIMGVVMQ  305
```

FIGURE 13

SEQUENCE LISTING

<160> NUMBER OF SEQ ID NOS: 5

<210> SEQ ID NO 1
<211> LENGTH: 306
<212> TYPE: PRT
<213> ORGANISM: Severe acute respiratory syndrome coronavirus 2

<400> SEQUENCE: 1

```
Ser Gly Phe Arg Lys Met Ala Phe Pro Ser Gly Lys Val Glu Gly

```
                225                 230                 235                 240
Pro Leu Thr Gln Asp His Val

```
Asp Glu Phe Thr Pro Phe Asp Val Val Arg Gln Cys Ser Gly Val Thr
    290                 295                 300
Phe Gln
305

<210> SEQ ID NO 3
<211> LENGTH: 306
<212> TYPE: PRT
<213> ORGANISM: Middle East respiratory syndrome-related coronavirus

<400> SEQUENCE: 3

Ser Gly Leu Val Lys Met Ser His Pro Ser Gly Asp Val Glu Ala Cys
1               5                   10                  15

Met Val Gln Val Thr Cys Gly Ser Met Thr Leu Asn Gly Leu Trp Leu
            20                  25                  30

Asp Asn Thr Val Trp Cys Pro Arg His Val Met Cys Pro Ala Asp Gln
        35                  40                  45

Leu Ser Asp Pro Asn Tyr Asp Ala Leu Leu Ile Ser Met Thr Asn His
    50                  55                  60

Ser Phe Ser Val Gln Lys His Ile Gly Ala Pro Ala Asn Leu Arg Val
65                  70                  75                  80

Val Gly His Ala Met Gln Gly Thr Leu Leu Lys Leu Thr Val Asp Val
                85                  90                  95

Ala Asn Pro Ser Thr Pro Ala Tyr Thr Phe Thr Thr Val Lys Pro Gly
            100                 105                 110

Ala Ala Phe Ser Val Leu Ala Cys Tyr Asn Gly Arg Pro Thr Gly Thr
        115                 120                 125

Phe Thr Val Val Met Arg Pro Asn Tyr Thr Ile Lys Gly Ser Phe Leu
    130                 135                 140

Cys Gly Ser Cys Gly Ser Val Gly Tyr Thr Lys Glu Gly Ser Val Ile
145                 150                 155                 160

Asn Phe Cys Tyr Met His Gln Met Glu Leu Ala Asn Gly Thr His Thr
                165                 170                 175

Gly Ser Ala Phe Asp Gly Thr Met Tyr Gly Ala Phe Met Asp Lys Gln
            180                 185                 190

Val His Gln Val Gln Leu Thr Asp Lys Tyr Cys Ser Val Asn Val Val
        195                 200                 205

Ala Trp Leu Tyr Ala Ala Ile Leu Asn Gly Cys Ala Trp Phe Val Lys
    210                 215                 220

Pro Asn Arg Thr Ser Val Val Ser Phe Asn Glu Trp Ala Leu Ala Asn
225                 230                 235                 240

Gln Phe Thr Glu Phe Val Gly Thr Gln Ser Val Asp Met Leu Ala Val
                245                 250                 255

Lys Thr Gly Val Ala Ile Glu Gln Leu Leu Tyr Ala Ile Gln Gln Leu
            260                 265                 270

Tyr Thr Gly Phe Gln Gly Lys Gln Ile Leu Gly Ser Thr Met Leu Glu
        275                 280                 285

Asp Glu Phe Thr Pro Glu Asp Val Asn Met Gln Ile Met Gly Val Val
    290                 295                 300

Met Gln
305

<210> SEQ ID NO 4
<211> LENGTH: 13
<212> TYPE: PRT
<213> ORGANISM: Artificial Sequence
```

```
<220> FEATURE:
<223> OTHER INFORMATION: Lys at position 1 is labelled with Dabcyl, and
      Met is labelled with Edans

<400> SEQUENCE: 4

Lys Thr Ser Ala Val Leu Gln Ser Gly Phe Arg Lys Met
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Met is labelled with Edans

<400> SEQUENCE: 5

Ser Gly Phe Arg Lys Met
1               5
```

PROTEASE INHIBITORS, PREPARATION, AND USES THEREOF

CROSS-REFERENCE TO RELATED APPLICATIONS

This application claims the priority under 35 U.S.C. § 119(a) of International Application No. PCT/CN2021/071256, filed on Jan. 12, 2021. The content of this application is incorporated herein by reference in its entirety.

Please insert the sequence listing, filed herewith in electronic format, into the application before the claims.

FIELD OF THE DISCLOSURE

The present disclosure relates to compounds that inhibit proteases such as 3C-like protease (3CLpro), compositions comprising the compounds, methods of preparing the compounds, and methods of using the compounds to treat a disease or a symptom of a disease caused by a coronavirus, e.g., severe acute respiratory syndrome coronavirus 2 (SARS-CoV-2).

BACKGROUND OF THE DISCLOSURE

The COVID-19 pandemic is caused by a novel coronavirus, SARS-CoV-2. There is a great need for drugs that specifically treat diseases caused by SARS-CoV-2 or other coronaviruses. The positive-sense RNA virus SARS-CoV-2 has more than 70% of its genome encode 16 non-structural proteins (nsps), named nsp1 to nsp16 (1, 2). The 16 nsps are translated as two polyproteins pp1a and pp1ab from which the individual nsps are generated by proteolytic cleavage. Specifically, pp1a is cleaved into nsp1 to nsp11, while pp1ab is cleaved into nsp1 to nsp10 and nsp12 to nsp16 (1). The cleavage is carried out by two proteases included in the 16 nsps—nsp3 and nsp5. Nsp3 is a large protein containing several domains among which the papain-like protease (PLpro) domain is responsible for the cleavage of the peptide bonds between nsp1 and 2, nsp2 and 3, and nsp3 and 4 (1, 3). Nsp5 is 3CLpro, a cysteine protease that cleaves peptide bonds to release nsp4 to nsp16 (1). 3CLpro has almost the same function in other coronaviruses.

After cleaving itself from pp1a and pp1ab, 3CLpro form a homodimer with a significant increased protease activity, facilitating it to cleave peptide bonds between other nsps. At the catalytic center of 3CLpro there is a catalytic dyad composed by His41 and Cys145. The working mechanism and the protein sequence of the catalytic domain of 3CLpro are conserved among different coronaviruses. The sequence identity between the 3CLpro of SARS-CoV-2 and that of SARS-CoV reaches 96%.

Inhibition of the protease activity of 3CLpro would block the release of nsp4 to nsp16 that are necessary for coronavirus replication. For example, nsp12 and nsp13, also known as the RNA-dependent RNA polymerase (RdRp) and helicase, respectively, are enzymes that catalyze the replication of the virus RNA genome. Therefore, 3CLpro is a promising target for the development of anti-coronavirus drugs. Several research teams have spent significant efforts in the development of inhibitors of SARS-CoV 3CLpro and SARS-CoV-2 3CLpro. The majority of these inhibitors are covalent inhibitors optimized from peptidic scaffolds (4). A large number of non-covalent inhibitors were also reported, however, most of them only showed poor activity in cell-free or cell-based assays.

The present disclosure provides non-covalent inhibitors of proteases such as SARS-CoV-2 3CLpro, as well as preparations and uses of these inhibitors.

SUMMARY OF THE DISCLOSURE

One aspect of this disclosure provides a compound selected from compounds of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, which can be employed in the treatment of diseases and/or symptoms thereof caused by a coronavirus. For example, disclosed herein is a compound of the following structural Formula I:

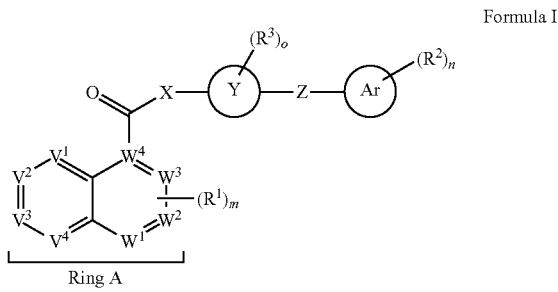

Formula I a tautomer thereof, a deuterated derivative of the compound or the tautomer, or a pharmaceutically acceptable salt of the foregoing, wherein:

Ar is phenyl or 6-membered heteroaryl;
Ring A is 9- or 10-membered heteroaryl, wherein:
  $V^1$, $V^2$, $V^3$, and $V^4$ are each absent, —CH—, or N; wherein:
    no more than one of $V^1$, $V^2$, $V^3$, and $V^4$ can be absent; and
    when one of $W^1$, $W^2$, $W^3$, and $W^4$ is absent, then none of $V^1$, $V^2$, $V^3$, and
  $V^4$ can be absent;
  $W^1$, $W^2$, $W^3$, and $W^4$ are each absent, —CH—, or N; wherein:
    no more than one of $W^1$, $W^2$, $W^3$, and $W^4$ can be absent; and
    at least one of $W^1$, $W^2$, $W^3$, and $W^4$ must be N;
X is absent, —$NR^a$—, or —$NR^a(CR^bR^c)_a$—;
Y is absent, $C_3$-$C_{12}$ carbocyclyl, 3- to 12-membered heterocyclyl, or 5- to 10-membered heteroaryl; wherein the $C_3$-$C_{12}$ carbocyclyl of Y, the 3- to 12-membered heterocyclyl of Y, and the 5- to 10-membered heteroaryl of Y are each substituted with o groups of $R^3$;
Z is absent, —$NR^d$—, —$(CR^eR^f)_bNR^d$—, or —$C(=O)NR^d(CR^gR^h)_c$—; wherein:
  $R^a$ and $R^d$, for each occurrence, are each independently hydrogen or $C_1$-$C_4$ alkyl;
  $R^b$, $R^c$, $R^e$, and $R^f$, for each occurrence, are each independently hydrogen or $C_1$-$C_4$ alkyl that is optionally substituted with 1 to 3 groups selected from halogen, cyano, and $C_1$-$C_4$ alkoxy;
  $R^g$ and $R^h$, for each occurrence, are each independently hydrogen or $C_1$-$C_4$ alkyl that is optionally substituted with 1 to 3 groups selected from halogen, cyano, $C_1$-$C_4$ alkoxy, and —$C(=O)NR^iR^j$; wherein:
    $R^i$ and $R^j$, for each occurrence, are each independently hydrogen or $C_1$-$C_4$ alkyl; and a, b, and c are each independently an integer selected from 1, 2, 3, and 4;

$R^1$, $R^2$, and $R^3$, for each occurrence, are each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)$NR^pR^q$, —$NR^pR^q$, —$NR^pR^q$, —$NR^pC$(=O)$R^s$, —$NR^pC$(=O)$OR^s$, —$NR^pC$(=O)$NR^qR^r$, —$NR^pS$(=O)$_wR^s$, —$NO_2$, —$NO_2^+$, —NH(=O)OH, —$OR^s$, —OC(=O)$R^s$, —OC(=O)$OR^s$, —OC(=O)$NR^pR^q$, —S(=O)$_wR^s$, —S(=O)$_wNR^pR^q$, —$SO_3^-$, $C_3$-$C_{12}$ carbocyclyl, 3 to 12-membered heterocyclyl, phenyl, and 5 to 10-membered heteroaryl; wherein:

the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(=O)($C_1$-$C_6$ alkyl) are each optionally substituted with 1 to 3 groups selected from halogen, cyano, —C(=O)$R^s$, —C(=O)$OR^s$, —C(=O)$NR^pR^q$, —$NR^pR^q$, —$NR^pC$(=O)$R^s$, —$NR^pC$(=O)$OR^s$, —$NR^pC$(=O)$NR^qR^r$, —$NR^pS$(=O)$_wR^s$. —$OR^s$, —OC(=O)$R^s$, —OC(=O)$OR^s$, —OC(=O)$NR^pR^q$, —S(=O)$_wR^s$, —S(=O)$_wNR^pR^q$, $C_3$-$C_6$ cycloalkyl, and phenyl that is optionally substituted with 1 to 3 halogen atoms;

the $C_3$-$C_{12}$ carbocyclyl, the 3 to 12-membered heterocyclyl, the phenyl, the 5 to 10-membered heteroaryl of any one of $R^1$, $R^2$, and $R^3$ are each optionally substituted with 1 to 3 groups selected from halogen, cyano, $C_1$-$C_4$ alkyl, —$NR^pR^q$, and —$OR^s$;

$R^p$, $R^q$, and $R^r$, for each occurrence, are each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$ r is optionally substituted with 1 to 3 groups selected from halogen, cyano, and —OH;

$R^s$, for each occurrence, is each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$ is optionally substituted with 1 to 3 groups selected from halogen, cyano, and —OH;

w is an integer selected from 1 and 2; and $R^1$, for each occurrence, may be attached to any of the ring atoms on either of the two monocyclic rings that are fused together to form Ring A in formula I, as long as valency permits; and m is an integer selected from 0, 1, 2, 3, 4, 5, and 6;

n is an integer selected from 1, 2, 3, 4, and 5; and o is an integer selected from 0, 1, 2, and 3.

In one aspect of the disclosure, the compounds of Formula I are selected from Compounds 1 to 23 shown below, a tautomer thereof, a deuterated derivative of the compound or the tautomer, or a pharmaceutically acceptable salt of the foregoing.

In some embodiments, the disclosure provides pharmaceutical compositions comprising a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, and a pharmaceutically acceptable carrier. In some embodiments, the pharmaceutical compositions may comprise a compound selected from Compounds 1 to 23 shown below, a tautomer thereof, a deuterated derivative of the compound or the tautomer, or a pharmaceutically acceptable salt of the foregoing. These compositions may further comprise an additional active pharmaceutical agent.

Another aspect of the disclosure provides methods of treating a disease and/or a symptom of a disease caused by a coronavirus (e.g., a respiratory tract infectious disease), comprising administering to a subject, a therapeutically effective amount of a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or a pharmaceutical composition comprising any of the foregoing. In some embodiments, the methods of treatment comprise administering to a subject, a compound selected from Compounds 1 to 23 shown below, a tautomer thereof, a deuterated derivative of the compound or the tautomer, or a pharmaceutically acceptable salt of the foregoing, or a pharmaceutical composition comprising any of the foregoing.

In some embodiments, the methods of treatment comprise administration of an additional active pharmaceutical agent to the subject in need thereof, either in the same pharmaceutical composition as a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or in a separate composition. In some embodiments, the methods of treatment comprise administering a compound selected from Compounds 1 to 23 shown below, a tautomer thereof, a deuterated derivative of the compound or the tautomer, or a pharmaceutically acceptable salt of the foregoing with an additional active pharmaceutical agent either in the same pharmaceutical composition or in a separate composition.

Also disclosed herein are methods of reducing or inhibiting the activity of a protease of a coronavirus, comprising administering to a subject, a therapeutically effective amount of a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the activity of a coronavirus protease comprise administering to a subject, a compound selected from Compounds 1 to 23 shown below, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the activity of a protease of a coronavirus comprise contacting said coronavirus or said protease with a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the activity of a protease of a coronavirus comprise contacting said coronavirus or said protease with a compound selected from Compounds 1 to 23 shown below, a tautomer thereof, a deuterated derivative of the compound or the tautomer, or a pharmaceutically acceptable salt of the foregoing, or a pharmaceutical composition comprising any of the foregoing.

Further disclosed herein are methods of reducing or inhibiting the replication of a coronavirus, comprising administering to a subject, a therapeutically effective amount of a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the replication of a coronavirus comprise administering to a subject, a compound selected from Compounds 1 to 23 shown below, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the replication of a coronavirus contacting said coronavirus or a protease of the coronavirus with a compound of Formulae I, II, IIIa, IIIb-1, IIIb-2, IIIc, IVa, IVb-1, IVb-2, IVc, Va, or Vb-2, a tautomer thereof, a deuterated derivative of the compound or the tautomer, or a pharmaceutically acceptable salt of the foregoing, or a pharmaceutical composition comprising any of the foregoing. In some embodiments, the methods of reducing or inhibiting the replication of a coronavirus contacting said coronavirus or a protease of the coronavirus with a compound selected from Compounds 1 to 23 shown below, a tautomer thereof, a deuterated derivative of the compound or the tautomer, or a pharmaceutically acceptable salt of the foregoing, or a pharmaceutical composition comprising any of the foregoing.

BRIEF DESCRIPTION OF THE DRAWINGS

FIG. 8A shows that Compound 2 (sticks) binds into the catalytic pocket of 3CLpro. The surface electrostatic potential of 3CLpro was calculated by PyMol. FIG. 8B shows interactions between Compound 2 and 3CLpro. The hydrogen bonds are indicated by dashed lines.

FIG. 9A shows that Compound 8 (sticks) binds into the catalytic pocket of 3CLpro. The surface electrostatic potential of 3CLpro was calculated by PyMol. FIG. 9B shows interactions between Compound 8 and 3CLpro. The hydrogen bonds are indicated by dashed lines.

FIG. 10A shows that Compound 1 (sticks) binds into the catalytic pocket of 3CLpro. The surface electrostatic potential of 3CLpro was calculated by PyMol. FIG. 10B shows interactions between Compound 1 and 3CLpro. The hydrogen bonds are indicated by dashed lines.

FIG. 13 shows the alignment of the amino acid sequences of 3CL proteases of SARS-CoV-2 (SEQ ID NO: 1), SARS-CoV (SEQ ID NO: 2), and MERS-CoV (SEQ ID NO: 3). Residues within 5 A of Compound 2 in the SARS-CoV-2 3CLpro are indicated by triangles.

DETAILED DESCRIPTION OF THE DISCLOSURE

I. Definitions

Figure 1A:
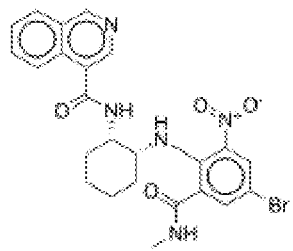
FIGS. 1A and 1B show the chemical structures of three inhibitors (FIG. 1A) and two analogues of Compound 2 (FIG. 1B).
Figure 1A:
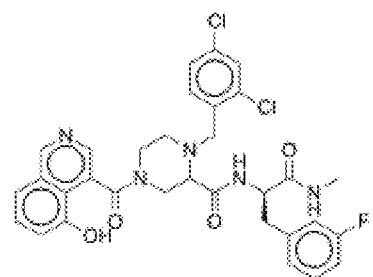
Figure 1A:
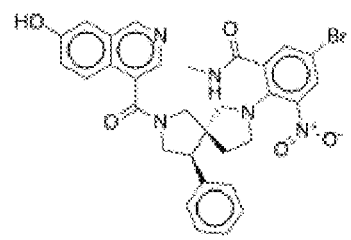

The term "a" or "an" when referring to a noun as used herein encompasses the expression "at least one" and therefore encompasses both singular and plural units of the noun. For example, "an additional pharmaceutical agent" means a single or two or more additional pharmaceutical agents.

The term "coronavirus" as used herein refers to a group of related RNA viruses that cause diseases in mammals and birds, such as typically respiratory tract infectious diseases in humans and birds that can range from mild to lethal, diarrhea in cows and pigs, and hepatitis and encephalomyelitis in mice. Coronaviruses are enveloped viruses with a positive-sense single-stranded RNA genome and a nucleocapsid of helical symmetry. They have characteristic club-shaped spikes that project from their surface, which in electron micrographs create an image reminiscence of the solar corona, from which their names. The lethal varieties of coronavirus include those that can case SARS (severe acute respiratory syndrome), MERS (Middle East respiratory syndrome), and COVID-19 (contagious disease caused by severe acute respiratory syndrome coronavirus 2 or SARS-CoV-2).

The term "inhibitor" as used herein refers to an organic chemistry small molecule compound (≤10 kDa) that has the ability to reduce or inhibit the expression of, and/or to reduce or inhibit the activity of any one or more proteases (e.g., by blocking the active site of the protease) of a coronavirus as defined above, including but not limited to the 3C-like protease ($3CL^{pro}$ or 3CLpro) or formally known as C30 endopeptidase that is the main protease of coronaviruses. The 3C-like protease cleaves the coronavirus polyprotein at multiple conserved sites having a glutamine-serine/glutamine-alanine/glutamine-glycine peptide bond, and is important in the processing of the coronavirus replicase polyprotein P0C6U8. Other examples of coronavirus proteases include the papain-like protease PLpro that is required for processing viral polyproteins to generate a functional replicase complex and enable viral spread.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors, including, for example, the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted," refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer" as used herein refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at a level that is well above its natural isotopic abundance, which is typically about 0.015%. In some embodiments, the deuterated derivatives disclosed herein have an isotopic enrichment factor for each deuterium atom, of at least 3500 (52.5% deuterium incorporation at each designated deuterium), at least 4500 (67.5% deuterium incorporation at each designated deuterium), at least 5000 (75% deuterium incorporation at each designated deuterium), at least 5500 (82.5% deuterium incorporation at each designated deuterium), at least 6000 (90% deuterium incorporation at each designated deuterium), at least 6333.3 (95% deuterium incorporation at each designated deuterium), at least 6466.7 (97% deuterium incorporation at each designated deuterium), or at least 6600 (99% deuterium incorporation at each designated deuterium).

The term "isotopic enrichment factor" as used herein means the ratio between the isotopic abundance and the natural abundance of a specified isotope.

The term "alkyl" as used herein, means a linear or branched, substituted or unsubstituted hydrocarbon chain that is completely saturated. Unless otherwise specified, an alkyl group contains 1 to 20 alkyl carbon atoms. In some embodiments, an alkyl group contains 1 to 10 aliphatic carbon atoms. In some embodiments, an alkyl group contains 1 to 8 aliphatic carbon atoms. In some embodiments, an alkyl group contains 1 to 6 alkyl carbon atoms. In some embodiments, an alkyl group contains 1 to 4 alkyl carbon atoms. In other embodiments, an alkyl group contains 1 to 3 alkyl carbon atoms. And in yet other embodiments, an alkyl group contains 1 to 2 alkyl carbon atoms. In some embodiments, alkyl groups are substituted. In some embodiments, alkyl groups are unsubstituted. In some embodiments, alkyl groups are linear or straight-chain or unbranched. In some embodiments, alkyl groups are branched.

The term "cycloalkyl" refers to a monocyclic $C_{3-8}$ hydrocarbon or a spirocyclic, fused, or bridged bicyclic or tricyclic $C_{8-14}$ hydrocarbon that is completely saturated, wherein any individual ring in said bicyclic ring system has 3 to 7 members. In some embodiments, cycloalkyl groups are substituted. In some embodiments, cycloalkyl groups are unsubstituted. In some embodiments, the cycloalkyl is a $C_3$ to $C_{12}$ cycloalkyl. In some embodiments, the cycloalkyl is a $C_3$ to $C_8$ cycloalkyl. In some embodiments, the cycloalkyl is a $C_3$ to $C_6$ cycloalkyl. Non-limiting examples of monocyclic cycloalkyls include cyclopropyl, cyclobutyl, cyclopentanyl, and cyclohexyl.

The term "carbocyclyl" encompasses the term "cycloalkyl" and refers to a monocyclic $C_{3-8}$ hydrocarbon or a spirocyclic, fused, or bridged bicyclic or tricyclic $C_{8-14}$ hydrocarbon that is completely saturated, or is partially saturated as it contains one or more units of unsaturation but is not aromatic, wherein any individual ring in said bicyclic ring system has 3 to 7 members. Bicyclic carbocyclyls include combinations of a monocyclic carbocyclic ring fused to, for example, a phenyl. In some embodiments, carbocyclyl groups are substituted. In some embodiments, carbocyclyl groups are unsubstituted. In some embodiments, the carbocyclyl is a $C_3$ to $C_{12}$ carbocyclyl. In some embodiments, the carbocyclyl is a $C_3$ to $C_{10}$ carbocyclyl. In some embodiments, the carbocyclyl is a $C_3$ to $C_8$ carbocyclyl.

The term "alkenyl" as used herein, means a linear or branched, substituted or unsubstituted hydrocarbon chain that contains one or more double bonds. In some embodiments, alkenyl groups are substituted. In some embodiments, alkenyl groups are unsubstituted. In some embodiments, alkenyl groups are linear, straight-chain, or unbranched. In some embodiments, alkenyl groups are branched.

The term "heterocyclyl" as used herein means non-aromatic (i.e., completely saturated or partially saturated as in it contains one or more units of unsaturation but is not aromatic), monocyclic, or spirocyclic, fused, or bridged bicyclic or tricyclic ring systems in which one or more ring members is an independently chosen heteroatom. Bicyclic heterocyclyls include, for example, the following combinations of monocyclic rings: a monocyclic heteroaryl fused to a monocyclic heterocyclyl; a monocyclic heterocyclyl fused to another monocyclic heterocyclyl; a monocyclic heterocyclyl fused to phenyl; a monocyclic heterocyclyl fused to a monocyclic carbocyclyl/cycloalkyl; and a monocyclic heteroaryl fused to a monocyclic carbocyclyl/cycloalkyl. In some embodiments, the "heterocyclyl" group contains 3 to 14 ring members in which one or more ring members is a heteroatom independently chosen, for example, from oxygen, sulfur, nitrogen, and phosphorus. In some embodiments, each ring in a bicyclic or tricyclic ring system contains 3 to 7 ring members. In some embodiments, the heterocycle has at least one unsaturated carbon-carbon bond. In some embodiments, the heterocycle has at least one unsaturated carbon-nitrogen bond. In some embodiments, the heterocycle has one heteroatom independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has two heteroatoms that are each independently selected from nitrogen and oxygen. In some embodiments, the heterocycle has three heteroatoms that are each independently selected from nitrogen and oxygen. In some embodiments, heterocycles are substituted. In some embodiments, heterocycles are unsubstituted. In some embodiments, the heterocyclyl is a 3- to 12-membered heterocyclyl. In some embodiments, the heterocyclyl is a 3- to 10-membered heterocyclyl. In some embodiments, the heterocyclyl is a 4- to 9-membered heterocyclyl, for example, a 4- to 9-membered heterocyclyl containing at least one N atom and optionally at least one O atom. In some embodiments, the heterocyclyl is a 5- to 10-membered heterocyclyl. In some embodiments, the heterocyclyl is a 5- to 8-membered heterocyclyl. In some embodiments, the heterocyclyl is a 5- or 6-membered heterocyclyl. In some embodiments, the heterocyclyl is a 6-membered heterocyclyl. Non-limiting examples of monocyclic heterocyclyls include piperidinyl, piperazinyl, tetrahydropyranyl, azetidinyl, tetrahydrothiophenyl 1,1-dioxide, etc.

The term "heteroatom" means one or more of oxygen, sulfur, and nitrogen, including, any oxidized form of nitrogen or sulfur; the quaternized form of any basic nitrogen or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated", as used herein, means that a moiety has one or more units or degrees of unsaturation. Unsaturation is the state in which not all of the available valence bonds in a compound are satisfied by substituents and thus the compound contains one or more double or triple bonds.

The term "alkoxy" as used herein, refers to an alkyl group, as defined above, wherein one carbon of the alkyl group is replaced by an oxygen ("alkoxy") atom, provided that the oxygen atom is linked between two carbon atoms.

The term "halogen" includes F, Cl, Br, and I, i.e., fluoro, chloro, bromo, and iodo, respectively.

As used herein, a "cyano" or "nitrile" group refers to —C≡N.

As used herein, an "aromatic ring" refers to a carbocyclic or heterocyclic ring that contains conjugated, planar ring systems with delocalized pi electron orbitals comprised of [4n+2] p orbital electrons, wherein n is an integer of 0 to 6. A "non-aromatic" ring refers to a carbocyclic or heterocyclic that does not meet the requirements set forth above for an aromatic ring, and can be either completely or partially saturated. Nonlimiting examples of aromatic rings include aryl and heteroaryl rings that are further defined as follows.

The term "aryl" used alone or as part of a larger moiety as in "arylalkyl," "arylalkoxy," or "aryloxyalkyl," refers to monocyclic or spirocyclic, fused, or bridged bicyclic or tricyclic ring systems having a total of five to fourteen ring members, wherein every ring in the system is an aromatic ring containing only carbon atoms and wherein each ring in a bicyclic or tricyclic ring system contains 3 to 7 ring members. Nonlimiting examples of aryl groups include phenyl ($C_6$) and naphthyl ($C_{10}$) rings. In some embodiments, aryl groups are substituted. In some embodiments, aryl groups are unsubstituted.

The term "heteroaryl" refers to monocyclic or spirocyclic, fused, or bridged bicyclic or tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. Bi-cyclic heteroaryls include, for example, the following combinations of monocyclic rings: a monocyclic heteroaryl fused to another monocyclic heteroaryl; and a monocyclic heteroaryl fused to a phenyl. Non-limiting examples of bi-cyclic heteroaryls are isoquinolinyl, quinolinyl, quinazolinyl, phthalazinyl, purinyl, and 1H-pyrrolo[2,3-c]pyridinyl. In some embodiments, heteroaryl groups are substituted. In some embodiments, heteroaryl groups have one or more heteroatoms chosen, for example, from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted. In some embodiments, the heteroaryl is a 3- to 12-membered heteroaryl. In some embodiments, the heteroaryl is a 3- to 10-membered heteroaryl. In some embodiments, the heteroaryl is a 3- to 8-membered heteroaryl. In some embodiments, the heteroaryl is a 5- to 10-membered heteroaryl. In some embodiments, the heteroaryl is a 5- to 8-membered heteroaryl. In some embodiments, the heteroaryl is a 5- or 6-membered heteroaryl. In some embodiments, the heteroaryl is a 6-membered heteroaryl. Non-limiting examples of monocyclic heteroaryls are pyridinyl, pyrimidinyl, thiophenyl, thiazolyl, isoxazolyl, etc.

Non-limiting examples of suitable solvents that may be used in this disclosure include water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether (Et$_2$O), methyl-tert-butyl ether (MTBE), 1,4-dioxane, and N-methyl pyrrolidone (NMP).

Non-limiting examples of suitable bases that may be used in this disclosure include 1,8-diazabicyclo[5.4.0] undec-7-ene (DBU), potassium tert-butoxide (KOtBu), potassium carbonate (K$_2$CO$_3$), N-methylmorpholine (NMM), triethylamine (Et$_3$N; TEA), diisopropyl-ethyl amine (i-Pr$_2$EtN; DIPEA), pyridine, potassium hydroxide (KOH), sodium hydroxide (NaOH), lithium hydroxide (LiOH) and sodium methoxide (NaOMe; NaOCH$_3$).

Disclosed herein are pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences*, 1977, 66, pp. 1 to 19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and N$^+$(C$_{1-4}$alkyl)$_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The term "subject" refers to an animal including a human.

The term "therapeutically effective amount" refers to that amount of a compound that produces the desired effect for which it is administered (e.g., improvement in a disease and/or a symptom of a disease caused by a coronavirus, lessening the severity of a disease and/or a symptom of a disease caused by a coronavirus, and/or reducing progression of a disease and/or a symptom caused by a coronavirus). The exact amount of a therapeutically effective amount will depend on the purpose of the treatment and will be ascertainable by one skilled in the art using known techniques (see, e.g., Lloyd (1999), The Art, Science and Technology of Pharmaceutical Compounding).

As used herein, the term "treatment" and its cognates refer to slowing or stopping disease progression. "Treatment" and its cognates as used herein include, but are not limited to the following: complete or partial remission, curing a disease caused by a coronavirus, lower risk of a disease and/or a symptom of a disease caused by a coronavirus. Improvements in or lessening the severity of any of these symptoms can be assessed according to methods and techniques known in the art.

The terms "about" and "approximately," when used in connection with a number such as a percentage include the number as specified, and a range of the number (e.g., a range of percentages) that is recognized by one of ordinary skill in the art.

II. Compounds and Compositions

In a first embodiment, a compound of this disclosure is a compound of the following structural formula I:

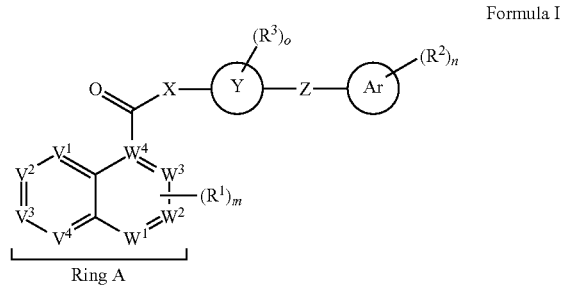

a tautomer thereof, a deuterated derivative of the compound or the tautomer, or a pharmaceutically acceptable salt of the foregoing, wherein:

Ar is phenyl or 6-membered heteroaryl;

Ring A is 9- or 10-membered heteroaryl, wherein:
V$^1$, V$^2$, V$^3$, and V$^4$ are each absent, —CH—, or N;
wherein:
no more than one of V$^1$, V$^2$, V$^3$, and V$^4$ can be absent; and
when one of W$^1$, W$^2$, W$^3$, and W$^4$ is absent, then none of V$^1$, V$^2$, V$^3$, and V$^4$ can be absent;
W$^1$, W$^2$, W$^3$, and W$^4$ are each absent, —CH—, or N;
wherein:
no more than one of W$^1$, W$^2$, W$^3$, and W$^4$ can be absent; and
at least one of W$^1$, W$^2$, W$^3$, and W$^4$ must be N;

X is absent, —NR$^a$—, or —NR$^a$(CR$^b$R$^c$)$_a$—;

Y is absent, C$_3$-C$_{12}$ carbocyclyl, 3- to 12-membered heterocyclyl, or 5- to 10-membered heteroaryl; wherein the $C_3$-$C_{12}$ carbocyclyl of Y, the 3- to 12-membered heterocyclyl of Y, and the 5- to 10-membered heteroaryl of Y are each substituted with o groups of $R^3$;

Z is absent, —$NR^d$—, —$(CR^eR^f)_b NR^d$—, or —C(=O)$NR^d(CR^gR^h)_c$—; wherein:

$R^a$ and $R^d$, for each occurrence, are each independently hydrogen or $C_1$-$C_4$ alkyl;

$R^b$, $R^c$, $R^e$, and $R^f$, for each occurrence, are each independently hydrogen or $C_1$-$C_4$ alkyl that is optionally substituted with 1 to 3 groups selected from halogen, cyano, and $C_1$-$C_4$ alkoxy;

$R^g$ and $R^h$, for each occurrence, are each independently hydrogen or $C_1$-$C_4$ alkyl that is optionally substituted with 1 to 3 groups selected from halogen, cyano, $C_1$-$C_4$ alkoxy, and —C(=O)$NR^iR^j$; wherein:

$R^i$ and $R^j$, for each occurrence, are each independently hydrogen or $C_1$-$C_4$ alkyl; and a, b, and c are each independently an integer selected from 1, 2, 3, and 4;

$R^1$, $R^2$, and $R^3$, for each occurrence, are each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)$NR^pR^q$, —$NR^pR^q$, —$NR^pC(=O)R^s$, —$NR^pC(=O)OR^s$, —$NR^pC(=O)NR^qR^r$, —$NR^pS(=O)_wR^s$, —$NO_2$, —$NO_2^+$, —NH(=O)OH, —$OR^s$, —OC(=O)$R^s$, —OC(=O)$OR^s$, —OC(=O)$NR^pR^q$, —S(=O)$_wR^s$, —S(=O)$_wNR^pR^q$, —$SO_3^-$, $C_3$-$C_{12}$ carbocyclyl, 3 to 12-membered heterocyclyl, phenyl, and 5 to 10-membered heteroaryl; wherein:

the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(=O)($C_1$-$C_6$ alkyl) are each optionally substituted with 1 to 3 groups selected from halogen, cyano, —C(=O)$R^s$, —C(=O)$OR^s$, —C(=O)$NR^pR^q$, —$NR^pR^q$, —$NR^pC(=O)R^s$, —$NR^pC(=O)OR^s$, —$NR^pC(=O)NR^qR^r$, —$NR^pS(=O)_wR^s$. —$OR^s$, —OC(=O)$R^s$, —OC(=O)$OR^s$, —OC(=O)$NR^pR^q$, —S(=O)$_wR^s$, —S(=O)$_wNR^pR^q$, $C_3$-$C_6$ cycloalkyl, and phenyl that is optionally substituted with 1 to 3 halogen atoms;

the $C_3$-$C_{12}$ carbocyclyl, the 3 to 12-membered heterocyclyl, the phenyl, the 5 to 10-membered heteroaryl of any one of $R^1$, $R^2$, and $R^3$ are each optionally substituted with 1 to 3 groups selected from halogen, cyano, $C_1$-$C_4$ alkyl, —$NR^pR^q$, and —$OR^s$;

$R^p$, $R^q$, and $R^r$, for each occurrence, are each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$ r is optionally substituted with 1 to 3 groups selected from halogen, cyano, and —OH;

$R^s$, for each occurrence, is each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$ is optionally substituted with 1 to 3 groups selected from halogen, cyano, and —OH;

w is an integer selected from 1 and 2; and $R^1$, for each occurrence, may be attached to any of the ring atoms on either of the two monocyclic rings that are fused together to form Ring A in formula I, as long as valency permits; and m is an integer selected from 0, 1, 2, 3, 4, 5, and 6;

n is an integer selected from 1, 2, 3, 4, and 5; and o is an integer selected from 0, 1, 2, and 3.

In one embodiment in formula I, Ar is phenyl, pyridinyl, or pyrimidinyl, each of which optionally substituted with m groups of $R^1$; and all other variables not specifically defined herein are as defined in the first embodiment. In one embodiment in formula I, Ar is phenyl optionally substituted with m groups of $R^1$; and all other variables not specifically defined herein are as defined in the first embodiment.

In one embodiment in formula I, Ring A is isoquinolinyl, quinolinyl, quinazolinyl, phthalazinyl, purinyl, or 1H-pyrrolo[2,3-c]pyridinyl, each of which optionally substituted with m groups of $R^1$; and all other variables not specifically defined herein are as defined in the first embodiment.

In one embodiment in formula I, Ring A is isoquinolinyl optionally substituted with m groups of $R^1$, wherein:

$V^1$, $V^2$, $V^3$, and $V^4$ are all —CH—;
$W^2$ is N; and
$W^1$, $W^3$, and $W^4$ are —CH—;

and all other variables not specifically defined herein are as defined above.

In one embodiment in formula I, Ring A is quinolinyl optionally substituted with m groups of $R^1$, wherein:

$V^1$, $V^2$, $V^3$, and $V^4$ are all —CH—;
$W^1$ is N; and
$W^2$, $W^3$, and $W^4$ are —CH—;

and all other variables not specifically defined herein are as defined in the first embodiment.

In one embodiment in formula I, Ring A is quinazolinyl optionally substituted with m groups of $R^1$, wherein:

$V^1$, $V^2$, $V^3$, and $V^4$ are all —CH—;
$W^2$ is —CH—; and
$W^1$, $W^3$, and $W^4$ are N;

and all other variables not specifically defined herein are as defined in the first embodiment.

In one embodiment in formula I, Ring A is phthalazinyl optionally substituted with m groups of $R^1$, wherein:

$V^1$, $V^2$, $V^3$, and $V^4$ are all —CH—;
$W^1$ is —CH—; and
$W^2$, $W^3$, and $W^4$ are N;

and all other variables not specifically defined herein are as defined in the first embodiment.

In one embodiment in formula I, Ring A is purinyl optionally substituted with m groups of $R^1$, wherein:

$V^1$, $V^2$, $V^3$, and $V^4$ are all —CH—; or alternatively $V^1$ and $V^3$ are all —CH— and $V^2$ and $V^4$ are N;
$W^1$ is absent;
$W^2$ is —CH—; and
$W^1$ and $W^3$ are N;

and all other variables not specifically defined herein are as defined in the first embodiment.

In one embodiment in formula I, Ring A is purinyl optionally substituted with m groups of $R^1$, wherein:

$V^1$ is absent;
$V^3$ is —CH—;
$V^2$ and $V^4$ are N;
$W^1$ and $W^3$ are —CH— and $W^2$ and $W^4$ are N; or alternatively $W^1$ and $W^3$ are N and $W^2$ and $W^4$ are —CH—;

and all other variables not specifically defined herein are as defined in the first embodiment.

In one embodiment in formula I, Ring A is 1H-pyrrolo[2,3-c]pyridinyl optionally substituted with m groups of $R^1$, wherein:

V⁴ is absent;
V¹ is N;
V² and V³ are —CH—;
W³ is N;
W¹, W², and W⁴ are —CH—;
and all other variables not specifically defined herein are as defined in the first embodiment.

In one embodiment in formula I, Ring A is 1H-pyrrolo[2,3-c]pyridinyl optionally substituted with m groups of R¹, wherein:
V⁴ is absent;
V³ is N;
V¹ and V² are —CH—;
W² is N;
W¹, W³, and W⁴ are —CH—;
and all other variables not specifically defined herein are as defined in the first embodiment.

In one embodiment in formula I, Ring A is 1H-pyrrolo[2,3-c]pyridinyl optionally substituted with m groups of R¹, wherein:
V³ is N;
V¹, V², and V⁴ are —CH—;
W¹ is absent;
W² is N;
W³ and W⁴ are —CH—;
and all other variables not specifically defined herein are as defined in the first embodiment.

In a second embodiment, a compound of the disclosure is one of the following structural formula II:

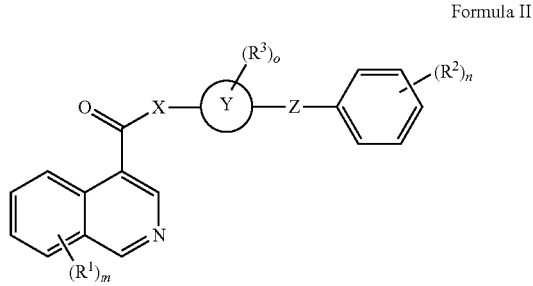

Formula II a tautomer thereof, a deuterated derivative of the compound or the tautomer, or a pharmaceutically acceptable salt of the foregoing; and all other variables not specifically defined herein are as defined in the preceding embodiment.

In a third embodiment, a compound of the disclosure is of one of the following structural formula IIIa:

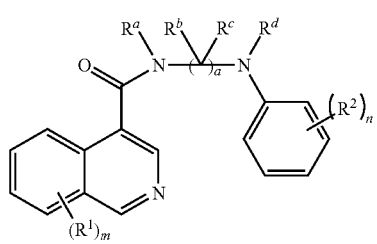

Formula IIIa a tautomer thereof, a deuterated derivative of the compound or the tautomer, or a pharmaceutically acceptable salt of the foregoing; and all other variables not specifically defined herein are as defined in any one of the preceding embodiments.

In a fourth embodiment, a compound of the disclosure is of the following structural formula IVa:

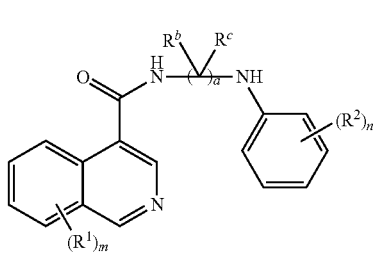

Formula IVa a tautomer thereof, a deuterated derivative of the compound or the tautomer, or a pharmaceutically acceptable salt of the foregoing; wherein:
$R^b$ and $R^c$, for each occurrence, are each independently hydrogen or $C_1$-$C_2$ alkyl that is optionally substituted with 1 to 3 groups selected from halogen, cyano, and $C_1$-$C_4$ alkoxy; and
a is an integer selected from 1 and 2;
and all other variables not specifically defined herein are as defined in any one of the preceding embodiments.

In a fifth embodiment, a compound of the disclosure is of the following structural formula Va:

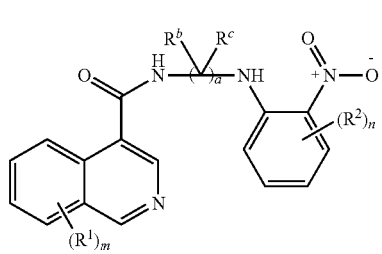

Formula Va a tautomer thereof, a deuterated derivative of the compound or the tautomer, or a pharmaceutically acceptable salt of the foregoing; wherein n is an integer selected from 1, 2, 3, and 4; and all other variables not specifically defined herein are as defined in any one of the preceding embodiments.

In a sixth embodiment, in a compound, tautomer, deuterated derivative, or pharmaceutically acceptable salt of this disclosure, Y is $C_3$-$C_{12}$ cycloalkyl or 3- to 12-membered heterocyclyl; and all other variables not specifically defined herein are as defined in any one of the preceding embodiments.

In a seventh embodiment, in a compound, tautomer, deuterated derivative, or pharmaceutically acceptable salt of this disclosure:
$R^a$, $R^b$, $R^c$, $R^d$, $R^e$, and $R^f$, for each occurrence, are each independently hydrogen or $C_1$-$C_2$ alkyl;
$R^g$ and $R^h$, for each occurrence, are each independently hydrogen or $C_1$-$C_2$ alkyl that is optionally substituted —C(=O)NR$^i$R$^j$; wherein:
$R^i$ and $R^j$, for each occurrence, are each independently hydrogen or $C_1$-$C_2$ alkyl; and
a, b, and c are each independently an integer selected from 1 and 2;
and all other variables not specifically defined herein are as defined in any one of the preceding embodiments.

In an eighth embodiment, a compound of the disclosure is of the following structural formula IIIb-1:

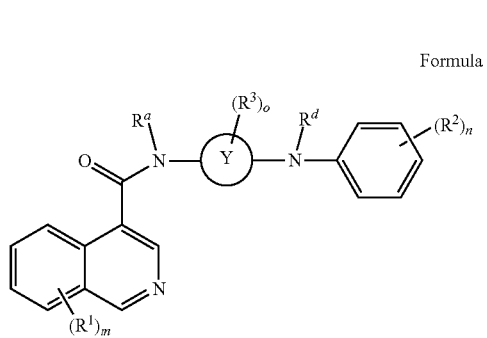

Formula IIIb-1 a tautomer thereof, a deuterated derivative of the compound or the tautomer, or a pharmaceutically acceptable salt of the foregoing; wherein:

Y is $C_3$-$C_{10}$ cycloalkyl; and o is an integer selected from 0 and 1;

and all other variables not specifically defined herein are as defined in any one of the preceding embodiments.

In a ninth embodiment, a compound of the disclosure is of the following structural formula IVb-1:

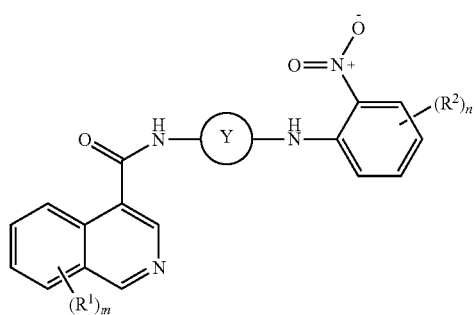

Formula IVb-1 a tautomer thereof, a deuterated derivative of the compound or the tautomer, or a pharmaceutically acceptable salt of the foregoing; wherein:

Y is $C_3$-$C_6$ cycloalkyl; and n is an integer selected from 1, 2, 3, and 4;

and all other variables not specifically defined herein are as defined in any one of the first, sixth, seventh, and eighth embodiments.

In a tenth embodiment, in a compound, tautomer, deuterated derivative, or pharmaceutically acceptable salt of this disclosure, Y is cyclohexyl; and all other variables not specifically defined herein are as defined in any one of the preceding embodiments.

In an eleventh embodiment, a compound of the disclosure is of the following structural formula IIIb-2:

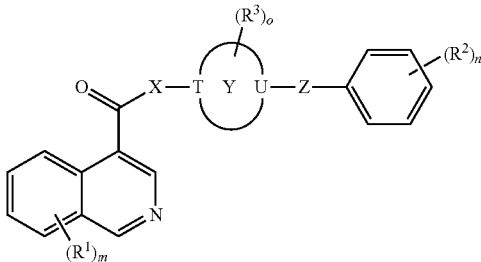

Formula IIIb-2 a tautomer thereof, a deuterated derivative of the compound or the tautomer, or a pharmaceutically acceptable salt of the foregoing; wherein:

Y is 3- to 10-membered heterocyclyl containing at least one N atom and optionally at least one other heteroatom selected from O and S;

at least one of T and U is N; and o is an integer selected from 0, 1, and 2;

and all other variables not specifically defined herein are as defined in any one of the preceding embodiments.

In a twelfth embodiment, in a compound, tautomer, deuterated derivative, or pharmaceutically acceptable salt of this disclosure:

X is absent, —NH—, or —NHCH$_2$—; and

Z is absent, —NH—, —[CH(CH(CH$_3$)$_2$)]NH—, or —C(=O)NHCH[(CONHCH$_3$)CH$_2$]—; and all other variables not specifically defined herein are as defined in any one of the preceding embodiments.

In a thirteenth embodiment, a compound of the disclosure is of the following structural formula IVb-2:

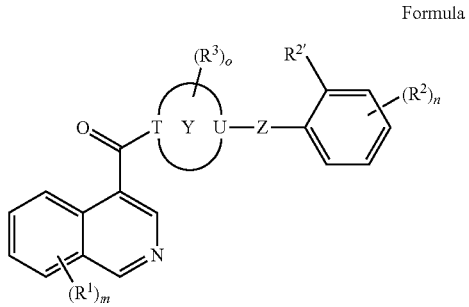

Formula IVb-2 a tautomer thereof, a deuterated derivative of the compound or the tautomer, or a pharmaceutically acceptable salt of the foregoing; wherein:

Y is 4- to 9-membered heterocyclyl containing at least one N atom and optionally at least one O atom;

at least one of T and U is N;

$R^{2'}$ is halogen, cyano, —NO$_2^+$, —NH(=O)OH, or —SO$_3^-$;

n is an integer selected from 1, 2, 3, and 4; and o is an integer selected from 0 and 1;

and all other variables not specifically defined herein are as defined in any one of the preceding embodiments.

In a fourteenth embodiment, a compound of the disclosure is of the following structural formula Vb-2:

Formula Vb-2

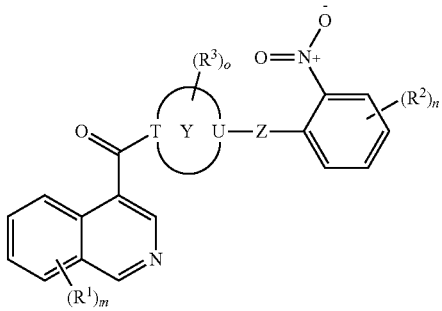

a tautomer thereof, a deuterated derivative of the compound or the tautomer, or a pharmaceutically acceptable salt of the foregoing; and all other variables not specifically defined herein are as defined in any one of the preceding embodiments.

In a fifteenth embodiment, in a compound, tautomer, deuterated derivative, or pharmaceutically acceptable salt of this disclosure, Y is azetidinyl, piperidinyl, piperazinyl, 2,7-diazaspiro[4.4]nonanyl, octahydrocyclopenta[c]pyrrolyl, 2-oxa-6-azaspiro[3.4]octanyl, or octahydro-1H-isoindolyl; and all other variables not specifically defined herein are as defined in any one of the preceding embodiments.

In a sixteenth embodiment, a compound of the disclosure is of the following structural formula IIIc:

Formula IIIc

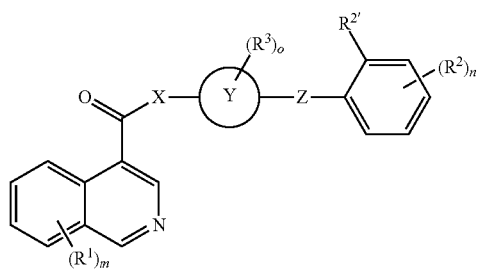

a tautomer thereof, a deuterated derivative of the compound or the tautomer, or a pharmaceutically acceptable salt of the foregoing; wherein:

$R^{2'}$ is halogen, cyano, $-NO_2^+$, $-NH(=O)OH$, or $-SO_3^-$; and n is an integer selected from 1, 2, 3, and 4;

and all other variables not specifically defined herein are as defined in any one of the preceding embodiments.

In a seventeenth embodiment, a compound of the disclosure is of the following structural formula IVc:

Formula IVc

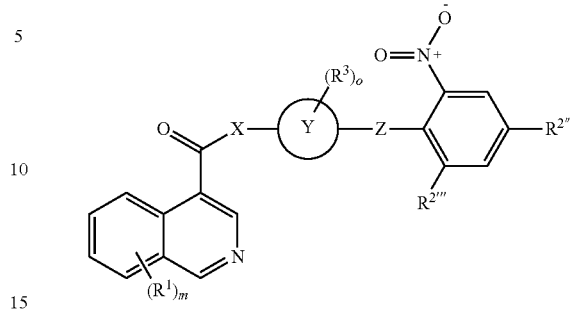

a tautomer thereof, a deuterated derivative of the compound or the tautomer, or a pharmaceutically acceptable salt of the foregoing; wherein:
  $R^{2''}$ is halogen or $C_1$-$C_4$ alkyl; and
  $R^{2'''}$ is $-C(=O)NR^pR^q$; wherein:
    $R^p$ and $R^q$ are each independently hydrogen or $C_1$-$C_4$ alkyl;
and all other variables not specifically defined herein are as defined any one of the preceding embodiments.

In an eighteenth embodiment, in a compound, tautomer, deuterated derivative, or pharmaceutically acceptable salt of this disclosure, wherein:
  $R^{2''}$ is F, Cl, Br or $C_1$-$C_2$ alkyl; and
  $R^{2'''}$ is $-C(=O)NR^pR^q$; wherein:
    $R^P$ and $R^q$ are each independently hydrogen or $C_1$-$C_2$ alkyl;
and all other variables not specifically defined herein are as defined in any one of the preceding embodiments.

In a nineteenth embodiment, in a compound, tautomer, deuterated derivative, or pharmaceutically acceptable salt of this disclosure, wherein:
  $R^{2''}$ is Br or $-CH_3$; and
  $R^{2'''}$ is $-C(=O)NHCH_3$;
and all other variables not specifically defined herein are as defined in any one of the seventeenth and eighteenth embodiments.

In a twentieth embodiment, in a compound, tautomer, deuterated derivative, or pharmaceutically acceptable salt of this disclosure, $R^1$, for each occurrence, is independently selected from halogen, cyano, $C_1$-$C_4$ alkyl, $C_1$-$C_4$ alkoxy, $-C(=O)(C_1$-$C_4$ alkyl), $-C(=O)NR^pR^q$, $-NR^pR^q$, and $-OR^s$ wherein:
  the $C_1$-$C_4$ alkyl and the $C_1$-$C_4$ alkoxy of $R^1$ and the $C_1$-$C_4$ alkyl of $-C(=O)(C_1$-$C_4$ alkyl) are each optionally substituted with 1 to 3 groups selected from halogen, cyano, and $-OR^s$;
  $R^p$ and $R^q$, for each occurrence, are each independently selected from hydrogen and $C_1$-$C_2$ alkyl; and
  $R^s$, for each occurrence, is independently selected from hydrogen and $C_1$-$C_2$ alkyl; and all other variables not specifically defined herein are as defined in any one of the preceding embodiments.

In a twenty-first embodiment, in a compound, tautomer, deuterated derivative, or pharmaceutically acceptable salt of this disclosure, $R^1$, for each occurrence, is independently selected from F, Cl, Br, $C_1$-$C_2$ alkyl, and $-OR^s$ wherein:
  the $C_1$-$C_2$ alkyl of $R^1$ is optionally substituted is optionally substituted with 1 to 3 groups of halogen; and
  $R^s$, for each occurrence, is independently selected from hydrogen and $C_1$-$C_2$ alkyl; and all other variables not specifically defined herein are as defined in any one of the preceding embodiments.

In a twenty-second embodiment, in a compound, tautomer, deuterated derivative, or pharmaceutically acceptable salt of this disclosure, $R^1$, for each occurrence, is independently selected from F and —OH; and all other variables not specifically defined herein are as defined in any one of the preceding embodiments.

In a twenty-third embodiment, in a compound, tautomer, deuterated derivative, or pharmaceutically acceptable salt of this disclosure, $R^3$, for each occurrence, is independently selected from halogen, cyano, $C_1$-$C_4$ alkyl, $C_1$-$C_4$ alkoxy, —C(=O)($C_1$-$C_4$ alkyl), —C(=O)$NR^pR^q$, —$NR^pR^q$, —$OR^s$, and phenyl; wherein:
  the $C_1$-$C_4$ alkyl and the $C_1$-$C_4$ alkoxy of $R^3$ and the $C_1$-$C_4$ alkyl of —C(=O)($C_1$-$C_4$ alkyl) are each optionally substituted with 1 to 3 groups selected from halogen, cyano, —$OR^s$, and phenyl that is optionally substituted with 1 to 3 halogen atoms;
  the phenyl of $R^3$ is optionally substituted with 1 to 3 groups selected from halogen, cyano, and $C_1$-$C_2$ alkyl;
  $R^p$ and $R^q$, for each occurrence, are each independently selected from hydrogen and $C_1$-$C_2$ alkyl; and
  $R^s$, for each occurrence, is independently selected from hydrogen and $C_1$-$C_2$ alkyl. and all other variables not specifically defined herein are as defined in any one of the preceding embodiments.

In a twenty-fourth embodiment, in a compound, tautomer, deuterated derivative, or pharmaceutically acceptable salt of this disclosure, $R^3$, for each occurrence, is independently selected from F, Cl, Br, $C_1$-$C_2$ alkyl, —$OR^s$, and phenyl; wherein:
  the $C_1$-$C_2$ alkyl of $R^3$ is optionally substituted is optionally substituted with 1 to 3 groups selected from halogen, cyano, and phenyl that is optionally substituted with 1 to 3 halogen atoms; and
  $R^s$, for each occurrence, is independently selected from hydrogen and $C_1$-$C_2$ alkyl; and all other variables not specifically defined herein are as defined in any one of the preceding embodiments.

In a twenty-fifth embodiment, in a compound, tautomer, deuterated derivative, or pharmaceutically acceptable salt of this disclosure, $R^3$, for each occurrence, is independently selected from —OH, phenyl and 2,4-dichloro-1-methylbenzene; and all other variables not specifically defined herein are as defined in any one of the preceding embodiments.

In a twenty-sixth embodiment, in a compound, tautomer, deuterated derivative, or pharmaceutically acceptable salt of this disclosure, $R^2$, for each occurrence, is independently selected from halogen, cyano, $C_1$-$C_4$ alkyl, $C_1$-$C_4$ alkoxy, —C(=O)($C_1$-$C_4$ alkyl), —C(=O)$NR^pR^q$, —$NR^pR^q$, —$NO_2$, —$NO_2$, —NH(=O)OH, —$OR^s$, and —$SO_3^-$; wherein:
  the $C_1$-$C_4$ alkyl and the $C_1$-$C_4$ alkoxy of $R^2$ and the $C_1$-$C_4$ alkyl of —C(=O)($C_1$-$C_4$ alkyl) are each optionally substituted with 1 to 3 groups selected from halogen, cyano, —$OR^s$;
  $R^p$ and $R^q$, for each occurrence, are each independently selected from hydrogen and $C_1$-$C_2$ alkyl; and
  $R^s$, for each occurrence, is independently selected from hydrogen and $C_1$-$C_2$ alkyl; and all other variables not specifically defined herein are as defined in any one of the preceding embodiments.

In a twenty-seventh embodiment, in a compound, tautomer, deuterated derivative, or pharmaceutically acceptable salt of this disclosure, $R^2$, for each occurrence, is independently selected from F, Cl, Br, cyano, $C_1$-$C_2$ alkyl, —C(=O)$NR^pR^q$, —$NO_2$, —$NO_2^+$, —NH(=O)OH, —$OR^s$, and —$SO_3^-$; wherein:
  the $C_1$-$C_2$ alkyl of $R^2$ is optionally substituted with 1 to 3 groups of halogen;
  $R^p$ and $R^q$, for each occurrence, are each independently selected from hydrogen and —$CH_3$; and
  $R^s$, for each occurrence, is independently selected from hydrogen and $C_1$-$C_2$ alkyl; and all other variables not specifically defined herein are as defined in any one of the preceding embodiments.

In a twenty-eighth embodiment, in a compound, tautomer, deuterated derivative, or pharmaceutically acceptable salt of this disclosure, $R^2$, for each occurrence, is independently selected from Br, —$CH_3$, —C(=O)$NHCH_3$, —$NO_2^+$, —NH(=O)OH, and —$SO_3^-$; and all other variables not specifically defined herein are as defined in any one of the preceding embodiments.

In a twenty-ninth embodiment, in a compound, tautomer, deuterated derivative, or pharmaceutically acceptable salt of this disclosure, $R^2$, for each occurrence, is independently selected from halogen, cyano, $C_1$-$C_4$ alkyl, $C_1$-$C_4$ alkoxy, —C(=O)($C_1$-$C_4$ alkyl), —C(=O)$NR^pR^q$, —$NR^pR^q$, and —$OR^s$ wherein:
  the $C_1$-$C_4$ alkyl and the $C_1$-$C_4$ alkoxy of $R^2$ and the $C_1$-$C_4$ alkyl of —C(=O)($C_1$-$C_4$ alkyl) are each optionally substituted with 1 to 3 groups selected from halogen, cyano, —$OR^s$;
  $R^p$ and $R^q$, for each occurrence, are each independently selected from hydrogen and $C_1$-$C_2$ alkyl; and
  $R^s$, for each occurrence, is independently selected from hydrogen and $C_1$-$C_2$ alkyl; and all other variables not specifically defined herein are as defined in any one of the preceding embodiments.

In a thirtieth embodiment, in a compound, tautomer, deuterated derivative, or pharmaceutically acceptable salt of this disclosure, $R^2$, for each occurrence, is independently selected from F, Cl, Br, cyano, $C_1$-$C_2$ alkyl, —C(=O)$NR^pR^q$, and —$OR^s$; wherein:
  the $C_1$-$C_2$ alkyl of $R^2$ is optionally substituted with 1 to 3 groups of halogen;
  $R^p$ and $R^q$, for each occurrence, are each independently selected from hydrogen and —$CH_3$; and
  $R^s$, for each occurrence, is independently selected from hydrogen and $C_1$-$C_2$ alkyl; and all other variables not specifically defined herein are as defined in any one of the preceding embodiments.

In a thirty-first embodiment, in a compound, tautomer, deuterated derivative, or pharmaceutically acceptable salt of this disclosure, $R^2$, for each occurrence, is independently selected from Br, —$CH_3$, and —C(=O)$NHCH_3$; and all other variables not specifically defined herein are as defined in any one of the preceding embodiments.

In a thirty-second embodiment, in a compound, tautomer, deuterated derivative, or pharmaceutically acceptable salt of this disclosure, m is an integer selected from 0 and 1; and all other variables not specifically defined herein are as defined in any one of the preceding embodiments.

In a thirty-third embodiment, in a compound, tautomer, deuterated derivative, or pharmaceutically acceptable salt of this disclosure, m is an integer selected from 1 and 2; and all other variables not specifically defined herein are as defined in any one of the preceding embodiments.

In certain embodiments, the at least one compound of the disclosure is selected from Compounds 1 to 23 depicted in Table 1, a tautomer thereof, a deuterated derivative of the compound or the tautomer, or a pharmaceutically acceptable salt of the foregoing.
TABLE 1
Compounds 1 to 23
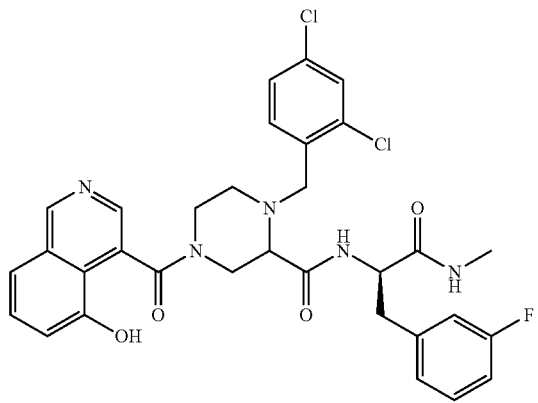 [SMILES: CNC(=O)[C@@H](Cc1cccc(F)c1)NC(=O)C1CN(C(=O)c2cncc3cccc(O)c23)CCN1Cc1ccc(Cl)cc1Cl]
1
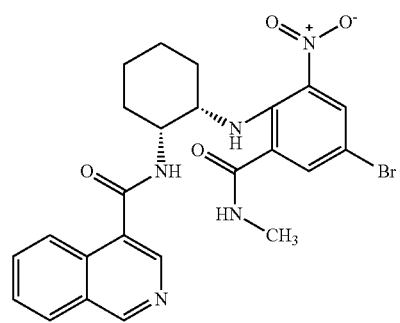 [SMILES: CNC(=O)c1cc(Br)cc([N+](=O)[O-])c1N[C@H]1CCCC[C@H]1NC(=O)c1cncc2ccccc12]
2
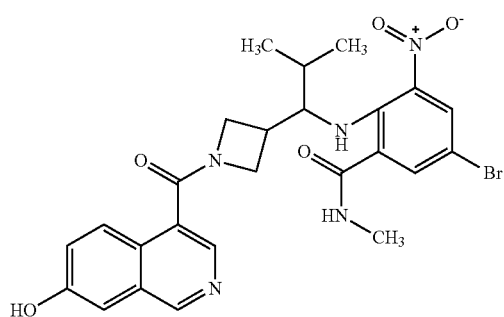
3
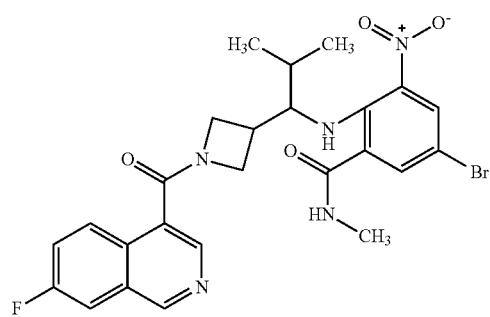 [SMILES: CNC(=O)c1cc(Br)cc([N+](=O)[O-])c1NC(C(C)C)C1CN(C(=O)c2cncc3cc(F)ccc23)C1]
4
TABLE 1-continued
Compounds 1 to 23
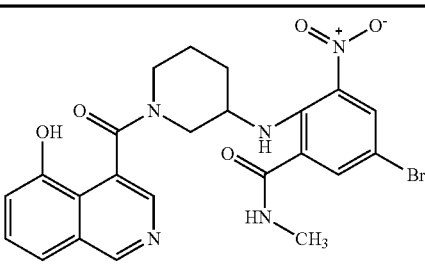
5
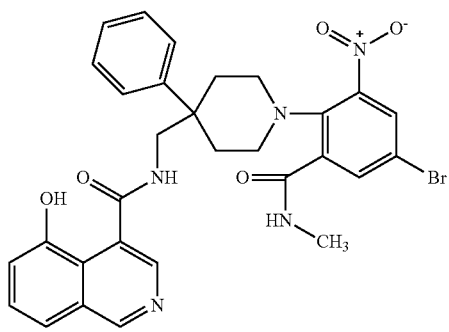 [SMILES: CNC(=O)c1cc(Br)cc([N+](=O)[O-])c1N1CCC(CNC(=O)c2cncc3cccc(O)c23)(c2ccccc2)CC1]
6
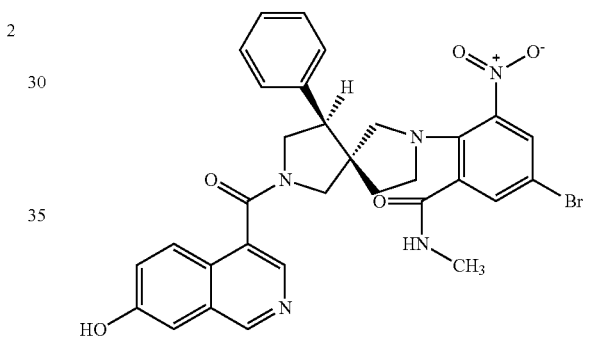
7
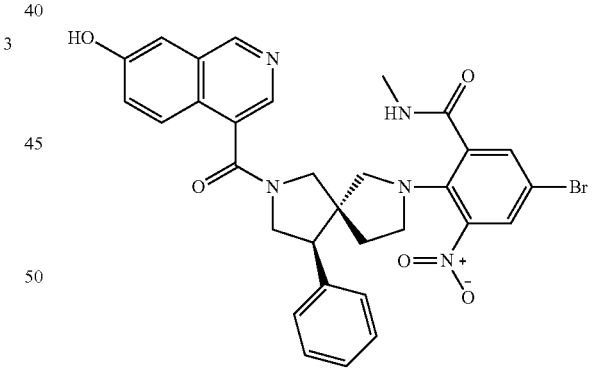
8
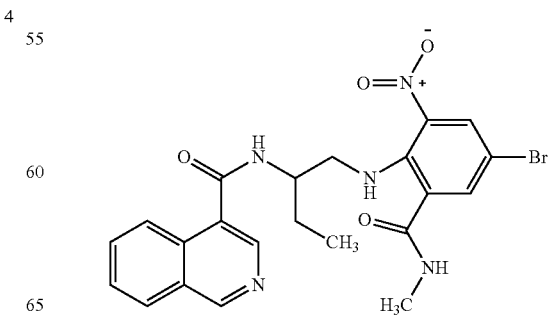
9

TABLE 1-continued
Compounds 1 to 23
10 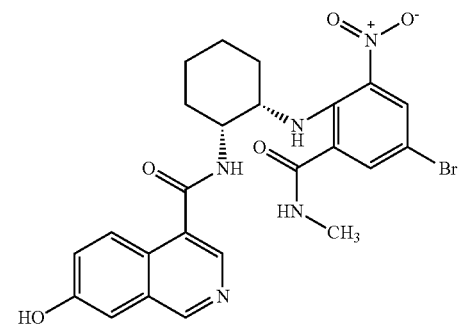 [SMILES: CNC(=O)c1cc(Br)cc([N+](=O)[O-])c1N[C@H]1CCCC[C@H]1NC(=O)c1cncc2cc(O)ccc12]
11 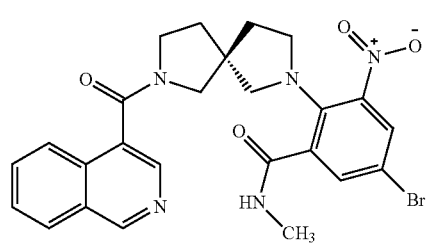 [SMILES: CNC(=O)c1cc(Br)cc([N+](=O)[O-])c1N1CC[C@@]2(CCN(C(=O)c3cncc4ccccc34)C2)C1]
12 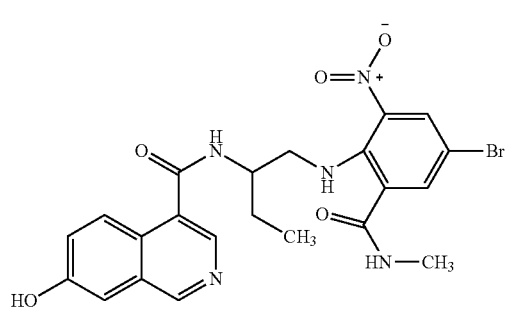 [SMILES: CCC(CNc1c(C(=O)NC)cc(Br)cc1[N+](=O)[O-])NC(=O)c1cncc2cc(O)ccc12]
13 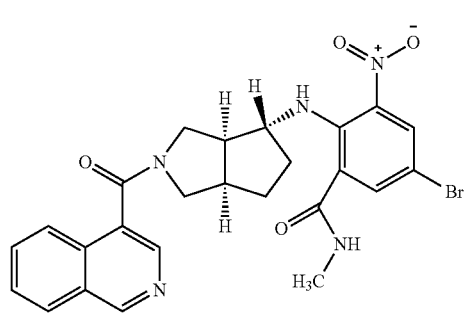 [SMILES: CNC(=O)c1cc(Br)cc([N+](=O)[O-])c1N[C@@H]1CC[C@H]2CN(C(=O)c3cncc4ccccc34)C[C@H]21]
14 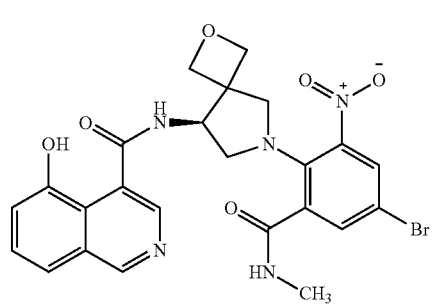 [SMILES: CNC(=O)c1cc(Br)cc([N+](=O)[O-])c1N1C[C@@H](NC(=O)c2cncc3cccc(O)c23)C2(COC2)C1]
15 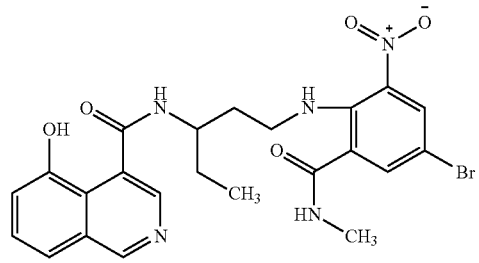 [SMILES: CCC(CCNc1c(C(=O)NC)cc(Br)cc1[N+](=O)[O-])NC(=O)c1cncc2cccc(O)c12]
16 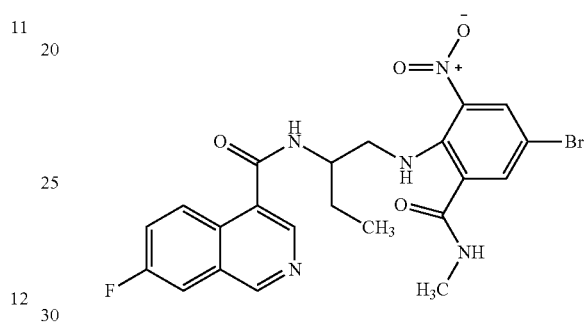
17 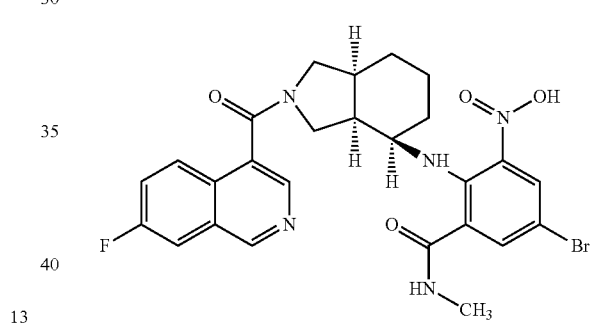
18 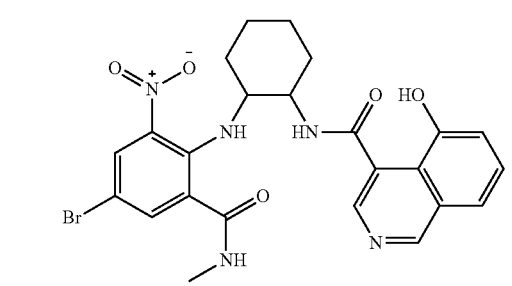
19 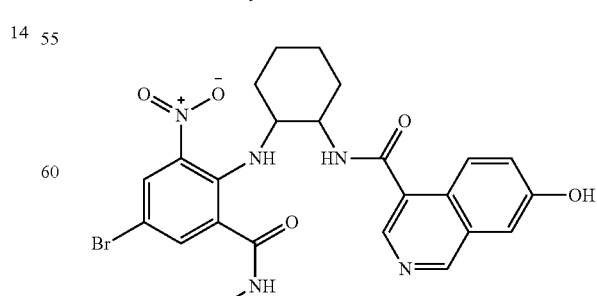

TABLE 1-continued

Compounds 1 to 23

20

21

22

23

Another aspect of the disclosure provides a pharmaceutical composition comprising at least one compound selected from a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, and at least one pharmaceutically acceptable carrier.

In some embodiments, the pharmaceutically acceptable carrier is selected from pharmaceutically acceptable vehicles and pharmaceutically acceptable adjuvants. In some embodiments, the pharmaceutically acceptable carrier is chosen from pharmaceutically acceptable fillers, disintegrants, surfactants, binders, and lubricants.

It will also be appreciated that a pharmaceutical composition of this disclosure can be employed in combination therapies; that is, the pharmaceutical compositions described herein can further include an additional active pharmaceutical agent. Alternatively, a pharmaceutical composition comprising a compound selected from a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing. The pharmaceutical composition comprising any of the foregoing can be administered as a separate composition concurrently with, prior to, or subsequent to, a composition comprising an additional active pharmaceutical agent.

As described above, the pharmaceutical compositions disclosed herein comprise a pharmaceutically acceptable carrier. The pharmaceutically acceptable carrier may be chosen from adjuvants and vehicles. The pharmaceutically acceptable carrier, as used herein, can be chosen, for example, from any and all solvents, diluents, other liquid vehicles, dispersion aids, suspension aids, surface active agents, isotonic agents, thickening agents, emulsifying agents, preservatives, solid binders, and lubricants, which are suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

III. Methods of Treatment and Uses

In another aspect of this disclosure, a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, is for use in treating a disease and/or a symptom of a disease caused by a coronavirus. In another aspect, disclosed herein is use of a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, for the manufacture of a medicament for treating a disease and/or a symptom or a disease caused by a coronavirus. In yet another aspect, disclosed herein is a method of treating a disease and/or a symptom of a disease in a subject, comprising administering a therapeutically effective amount of a compound, tautomer, deuterative derivative, or pharmaceutically acceptable salt as described herein, including a compound Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof.

In some embodiments, the disease caused by a coronavirus is a respiratory tract infection. In some embodiments, the disease caused by a coronavirus is a severe acute respiratory syndrome. In one embodiment, the disease caused by a coronavirus is COVID-19. In one embodiment, the disease caused by a coronavirus that is severe acute respiratory syndrome coronavirus 2 (SARS-CoV-2). In some embodiments, the symptom of a disease caused by a coronavirus is selected from fever or chills, cough, shortness of breath or difficulty in breathing, fatigue, muscle or body aches, headache, new loss of taste or smell, sore throat, congestion or runny nose, nausea or vomiting, diarrhea, persistent pain or pressure in the chest, new confusion, inability to wake or stay awake, bluish lips or face, and a combination thereof.

In another aspect of this disclosure, a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, is for use in reducing or inhibiting the activity of a protease of a coronavirus. In another aspect, disclosed herein is use of a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, for the manufacture of a medicament for reducing or inhibiting the activity of a protease of a coronavirus. In yet another aspect, disclosed herein is a method of reducing or inhibiting the activity of a protease of a coronavirus, comprising administering a therapeutically effective amount of a compound, tautomer, deuterative derivative, or pharmaceutically acceptable salt as described herein to a subject, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof. In yet another aspect, disclosed herein is a method of reducing or inhibiting the activity of a protease of a coronavirus, comprising contacting said coronavirus or said protease with a compound, tautomer, deuterative derivative, or pharmaceutically acceptable salt as described herein to a subject, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof. In one embodiment, the protease of a coronavirus is a 3C-like protease. In one embodiment, the coronavirus is SARS-CoV-2.

In another aspect of this disclosure, a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, is for use in reducing or inhibiting the replication of a coronavirus. In another aspect, disclosed herein is use of a compound, tautomer, deuterative derivative, or pharmaceutically acceptable salt as described herein, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof, for the manufacture of a medicament for reducing or inhibiting the replication of a coronavirus. In yet another aspect, disclosed herein is a method of reducing or inhibiting the replication of a coronavirus, comprising administering a therapeutically effective amount of a compound, tautomer, deuterative derivative, or pharmaceutically acceptable salt as described herein to a subject, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof. In yet another aspect, disclosed herein is a method of reducing or inhibiting the replication of a coronavirus, comprising contacting said coronavirus or a protease of the coronavirus with a compound, tautomer, deuterative derivative, or pharmaceutically acceptable salt as described herein to a subject, including a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof. In one embodiment, the protease of a coronavirus is a 3C-like protease. In one embodiment, the coronavirus is SARS-CoV-2.

A compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof may be administered once daily, twice daily, or three times daily, for example, for the treatment of a disease and/or a symptom of a disease caused by a coronavirus, for example, SARS-CoV-2.

In some embodiments, 2 mg to 1500 mg or 5 mg to 1000 mg of a compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof are administered once daily, twice daily, or three times daily.

A compound of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing, or a pharmaceutical composition thereof may be administered, for example, by oral, parenteral, sublingual, topical, rectal, nasal, buccal, vaginal, transdermal, patch, pump administration or via an implanted reservoir, and a pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time. Other forms of administration contemplated in this disclosure are as described in International Patent Application Nos. WO 2013/075083, WO 2013/075084, WO 2013/078320, WO 2013/120104, WO 2014/124418, WO 2014/151142, and WO 2015/023915.

EXAMPLES

In order that the disclosure described herein may be more fully understood, the following examples are disclosed herein. It should be understood that these examples are for illustrative purposes only and are not to be construed as limiting this disclosure in any way.

Example 1

Screening of 3CLpro Inhibitors

A series of non-covalent binders of SARS-CoV-2 3CLpro were identified through affinity screening and then scored through docking them into the substrate binding pocket of 3CLpro; three of these molecules that ranked high in the molecular docking study were synthesized (FIG. 1A).

Example 2

Synthesis of Exemplary Compounds

The compounds of the disclosure may be made according to standard chemical practices or as described herein, including the following synthetic schemes and in the descriptions for preparing a compound selected from compounds of Formulae I, II, IIIa, IIIb-1, IIIb-2, IIIc, IVa, IVb-1, IVb-2, IVc, Va, or Vb-2, Compounds 1 to 23, a tautomer thereof, a deuterated derivative of the compound or the tautomer, or a pharmaceutically acceptable salt of the foregoing.

General Schemes

A compound of Formula I may be prepared using exemplified synthesis procedures depicted in general Schemes A through D below. Variables not specifically defined in general Schemes A through D, such as $R^1$, $R^2$, $R^3$, $V^1$, $V^2$, $V^3$, $V^4$, $W^1$, $W^2$, $W^3$, $W^4$, m, n, and o, are as defined in Formula I in this disclosure.

General Scheme A $A^1, A^2, A^3, A^4, A^5 = N, \text{---CH---}$ $R^x$ = absent, $C_1$-$C_4$ alkyl Ring A Ring A General Scheme B $A^1, A^2, A^3, A^4, A^5 = N, \text{---CH---}$ 33
-continued
34
-continued
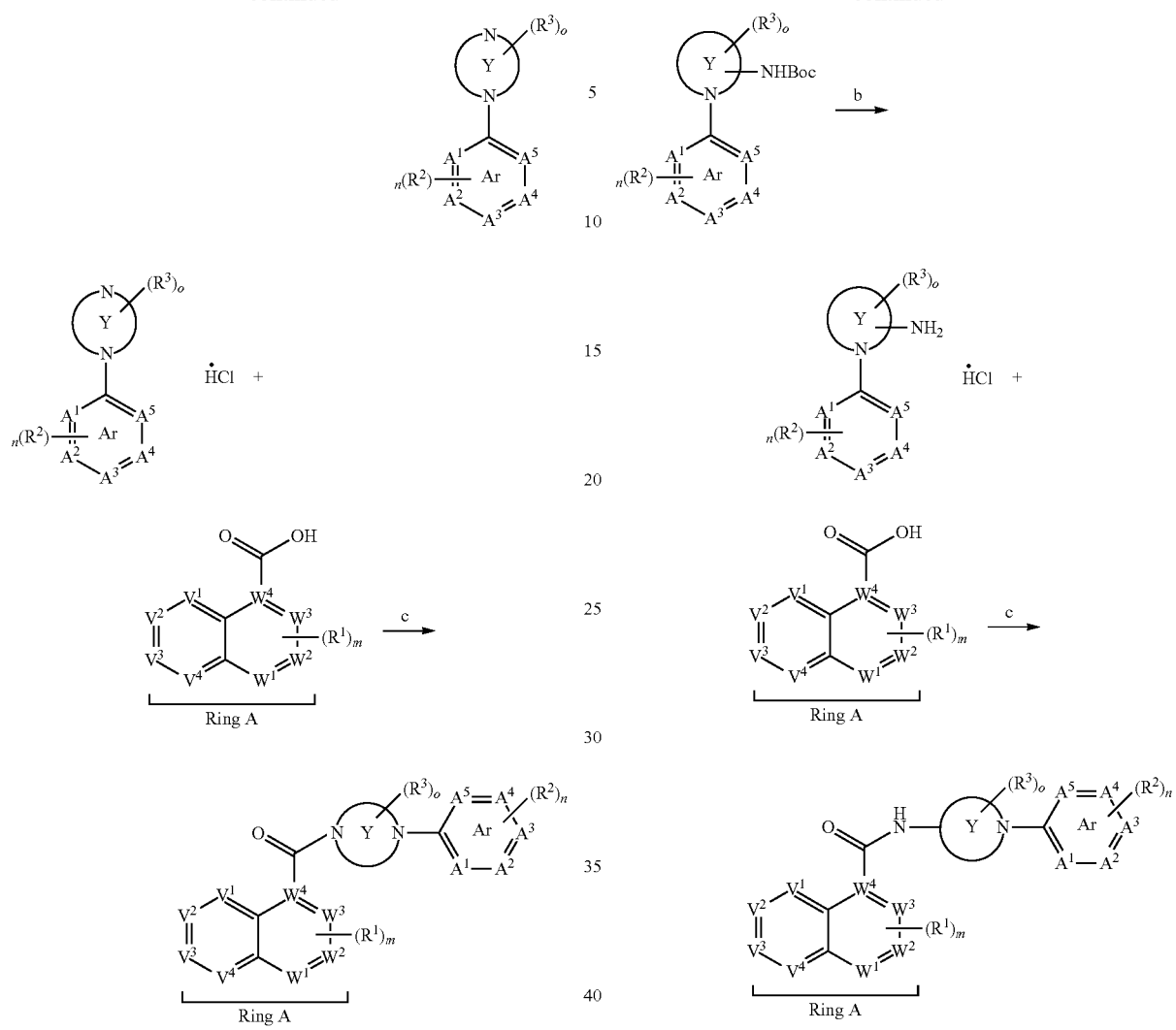
General Scheme C
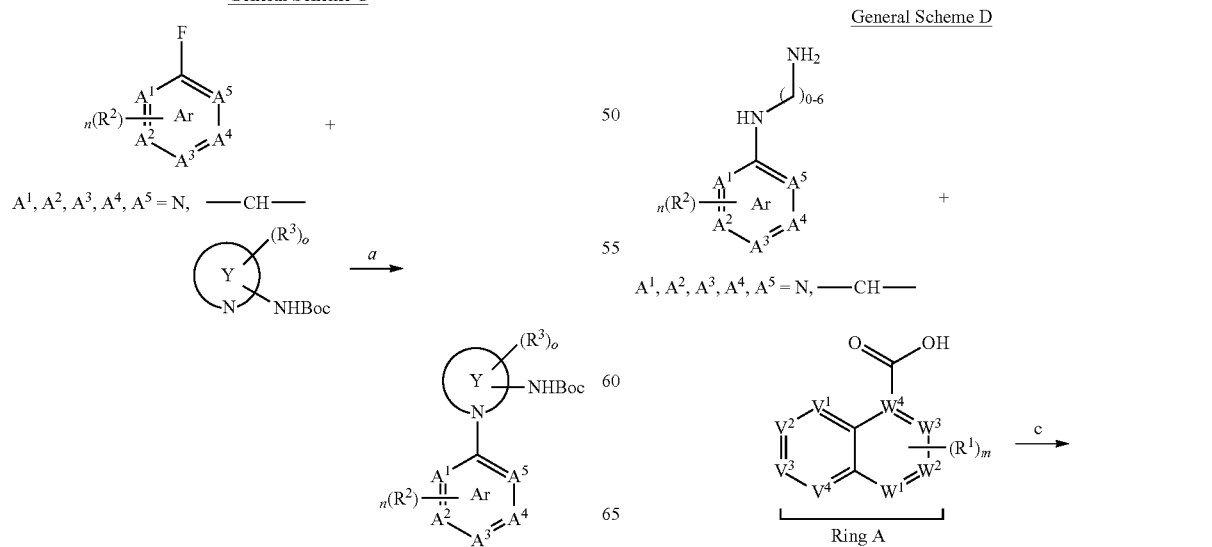
General Scheme D -continued

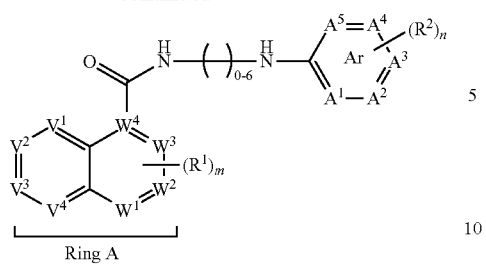

Ring A

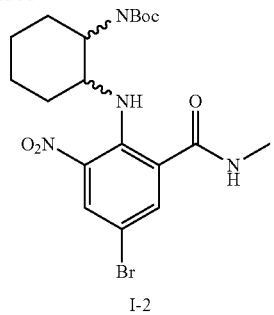

I-2

The reagents and conditions of Steps a to d as depicted in General Schemes A to D are: (a) DIPEA, dimethylformamide (DMF), 80° C., 16 h; (b) 3 M hydrogen chloride-ethyl acetate (HCl·EA), CH$_2$Cl$_2$, 1 h; (c) HATU, DIPEA, DMF, room temperature, 12 h.

Compound 2 and Analogues Compounds 10, 18, 19, 20, 21, 22, 23

Using Compounds 2 and its analogues (e.g., Compounds 10, 18, 19, 23) as representative examples, processes for preparing compounds of Formula I comprise the general reaction steps as described in Scheme 1. The wavy bond ( ⌇ ) shown in molecules in Scheme 1 such as Compounds I-2 and I-3 indicate that the stereochemistry of the bond may be undefined (e.g., ╱ which may be a racemic mixture of ▰ and ▱ such as in Compounds 18 and 19 or ▱ such as in Compounds 2, 10, and 23. Additional Compound 2 analogues such as Compounds 20, 21, and 22 may be prepared by modifying the synthesis procedure depicted in Scheme 1 as further described below.

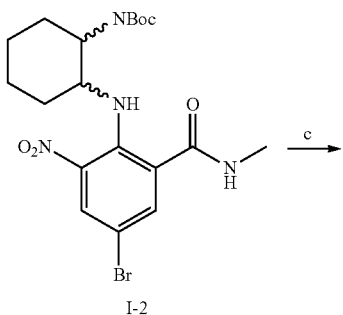

I-2

Scheme 1
Preparation of Compounds 2, 10, 18, 19, 23

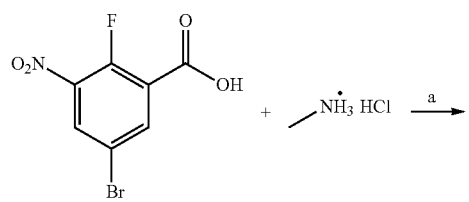

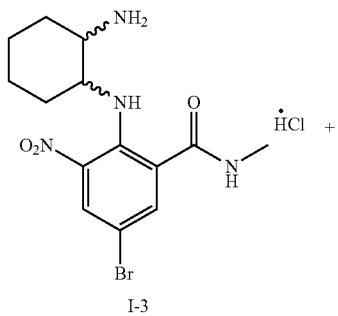

I-3

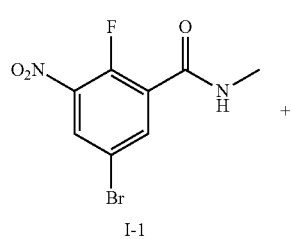

I-1

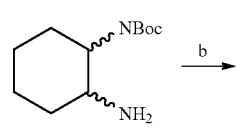

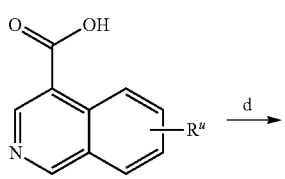

R$^u$ = H, OH, halogen

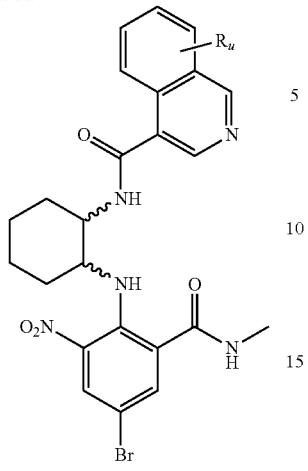

Compound 2 or an analogue thereof, e.g.
Compound 10,
Compound 19,
Compound 18,
Compound 23.

The reagents and conditions of Steps a to d as depicted in Scheme 1 and further described below are: (a) 1-[Bis(dimethylamino)methylene]-1H-1,2,3-triazolo[4,5-b]pyridinium 3-oxid hexafluorophosphate (HATU), N,N-Diisopropylethylamine (DIPEA), CH₂Cl₂ or dichloromethane (DCM), 0° C., 2 h; (b) DIPEA, dimethylformamide (DMF), 80° C., 16 h; (c) 3 M hydrogen chloride-ethyl acetate (HCl·EA), CH₂Cl₂, 1 h; (d) HATU, DIPEA, DMF, room temperature, 12 h.

Step a: Synthesis of N-methyl-5-bromo-2-fluoro-3-nitrobenzamide (I-1)

Figure 2A:
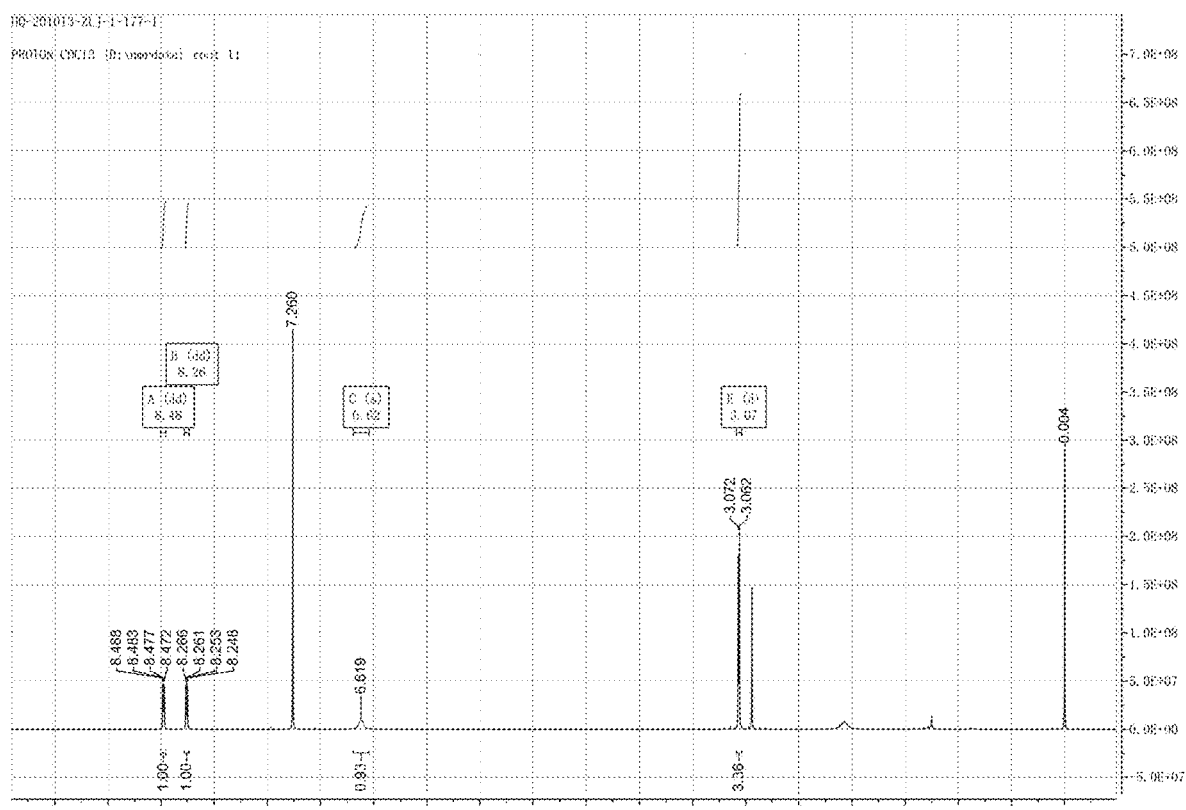
FIGS. 2A and 2B show the NMR (FIG. 2A) and mass spectrometry (FIG. 2B) characterization data of Compound I-1.
Figure 2B:
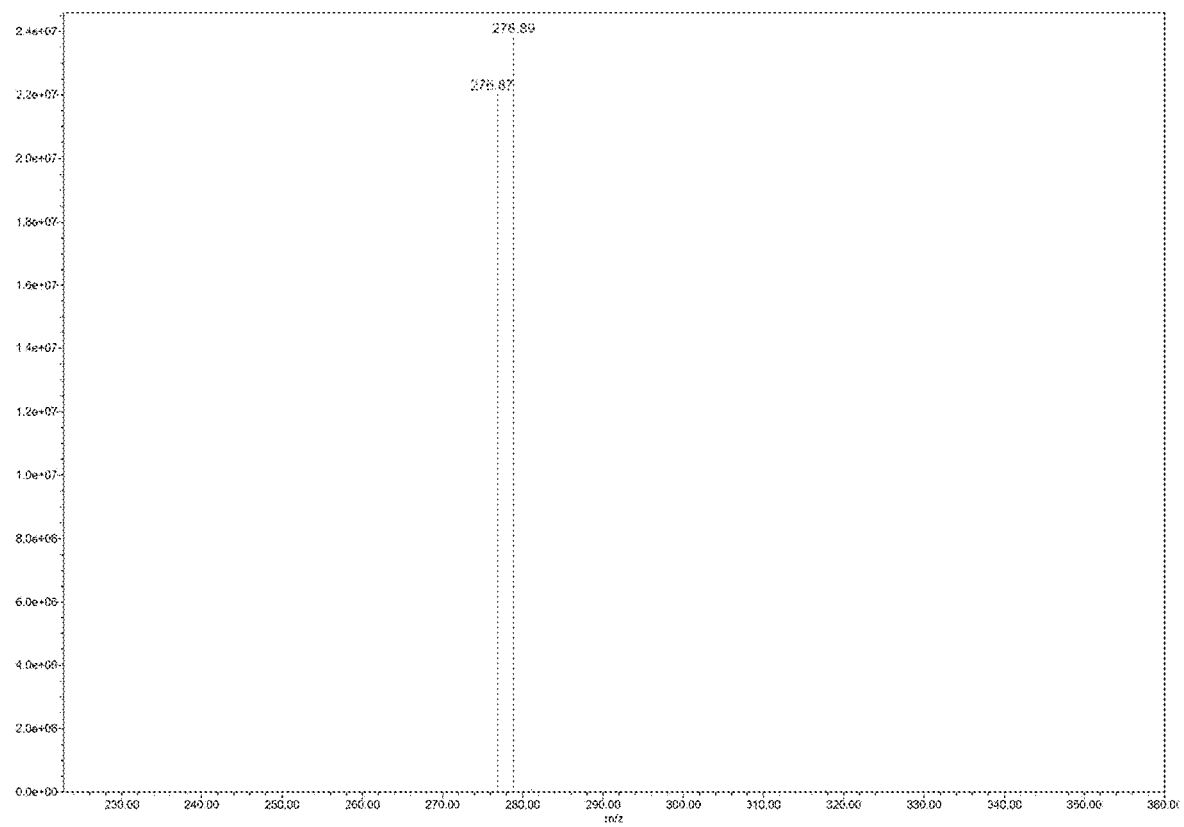

A solution of 5-bromo-2-fluoro-3-nitrobenzoic acid (0.8 g, 3.80 mmol) in dichloromethane (20 mL) was stirred at 0° C. Then, HATU (2.0 g, 5.25 mmol), DIPEA (1.88 ml, 11.4 mmol) and methylamine hydrochloride (0.31 g, 4.5 mmol) were added to the reaction. The mixture was stirred for 2 h at 0° C. and the mixture became clear. The mixture was extracted with dichloromethane three times and the combined organic layer was washed with saturated brine solution. Then the organic phase was dried over anhydrous Na₂SO₄ and concentrated under vacuum. Finally, the mixture was purified by chromatography to give Compound I-1 as yellow solid (0.8 g, 76% yield). ¹H NMR (500 MHz, CDCl₃) δ 8.48 (dd, J=5.5, 2.5 Hz, 1H), 8.26 (dd, J=6.5, 2.5 Hz, 1H), 6.62 (s, 1H), 3.07 (d, J=4.8 Hz, 3H). ESI-MS: m/z 276.87 [M+H]⁺. The NMR and mass spectrometry characterization data of Compound I-1 are presented in FIGS. 2A and 2B.

Step b: Synthesis of tert-butyl-2-(4-bromo-2-(methylcarbamoyl)-6-nitrophenyl)amino)cyclohexyl)carbamate (I-2)

A solution of Compound I-1 (0.8 g, 2.9 mmol) in DMF (15 mL) was stirred at room temperature. Then, tert-butyl ((1S,2R)-2-aminocyclohexyl)carbamate (0.75 g, 3.5 mmol) (a corresponding stereoisomer of this reagent can be used to synethesize a stereoiomer of Compound I-2(1)) and DIPEA (1.44 ml, 8.7 mmol) were added to the reaction. The mixture was warmed to 80° C. and stirred for 16 h. The mixture was extracted with ethyl acetate three times and the combined organic layer was washed with saturated brine solution. Then the organic phase was dried over anhydrous Na₂SO₄ and concentrated under vacuum to give Compound I-2(1) without further purification as yellow solid.

Compound I-2(1)

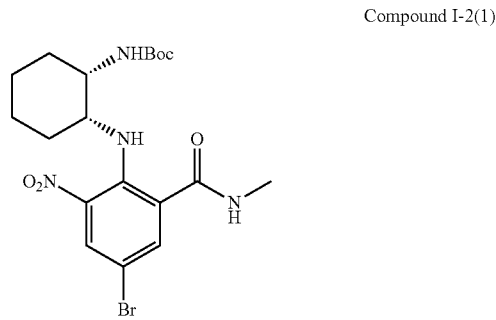

Figure 3A:
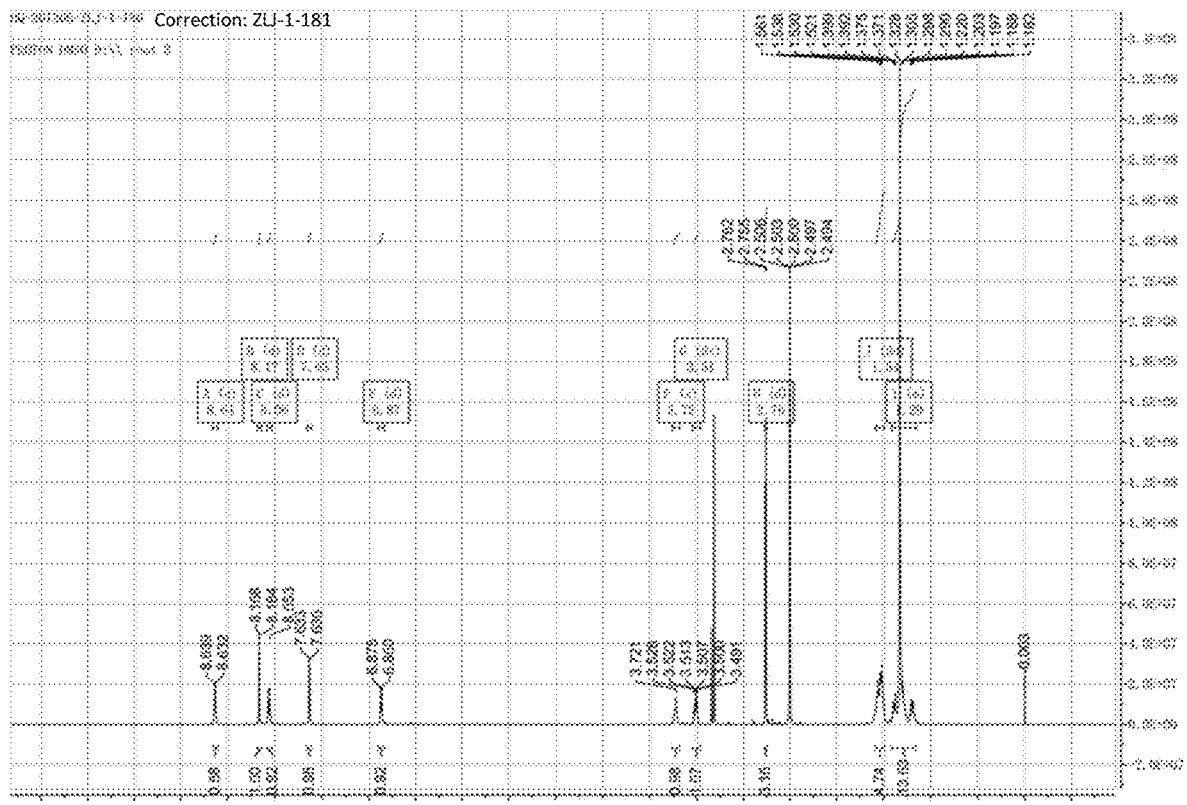
FIGS. 3A and 3B show the NMR (FIG. 3A) and mass spectrometry (FIG. 3B) characterization data of Compound I-2(1).
Figure 3B:
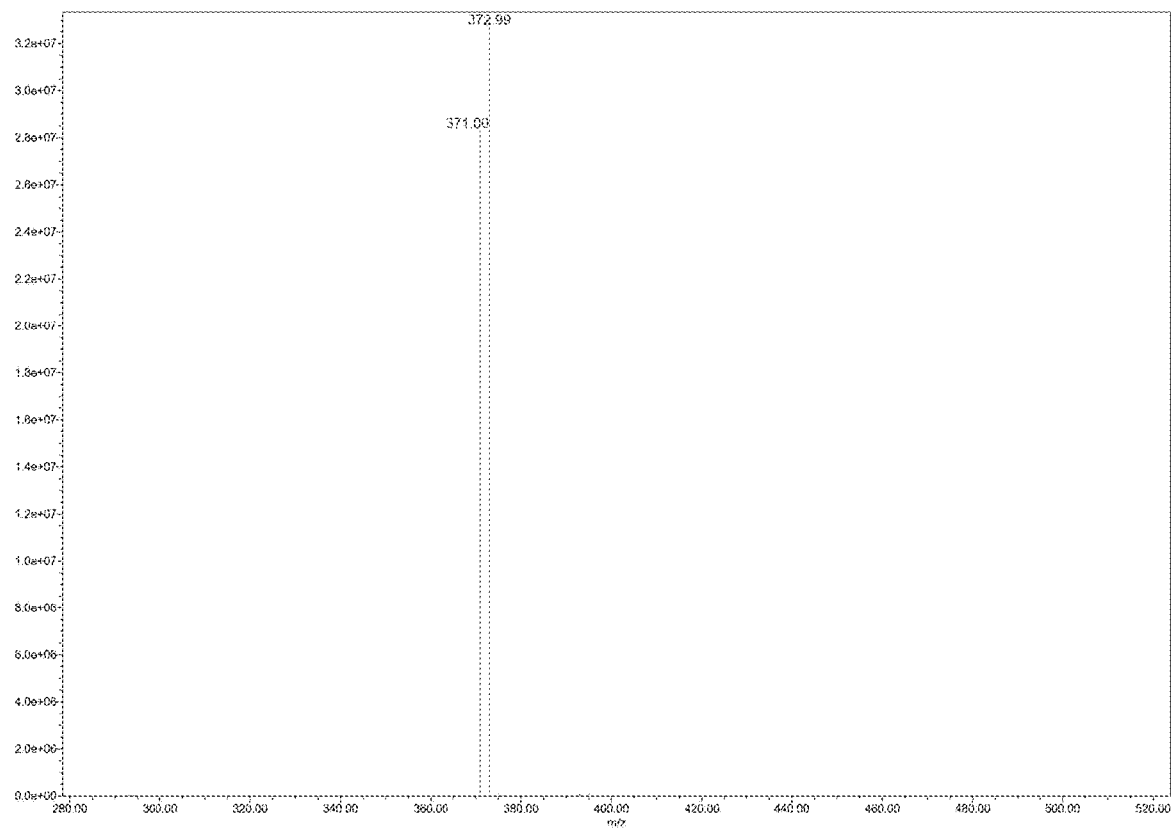

¹H NMR (600 MHz, DMSO) δ 8.64 (d, J=4.5 Hz, 1H), 8.17 (d, J=2.4 Hz, 1H), 8.06 (d, J=9.9 Hz, 1H), 7.63 (d, J=1.8 Hz, 1H), 6.87 (d, J=9.0 Hz, 1H), 3.72 (s, 1H), 3.51 (m, 1H), 2.76 (d, J=4.5 Hz, 3H), 1.54 (m, 4H), 1.41-1.15 (m, 13H). ESI-MS: m/z 371.00 [M-Boc+H]⁺. The NMR and mass spectrometry characterization data of Compound I-2(1) are presented in FIGS. 3A and 3B.

Step c: Synthesis of 2-(2-aminocyclohexyl)amino)-5-bromo-N-methyl-3-nitrobenzamide hydrochloride (I-3)

A solution of Compound I-2(1) (90 mg, 0.19 mmol) (or a corresponding stereoisomer) in anhydrous dichloromethane (6 mL) was stirred at room temperature. Then the HCl (4 mL, 3M in ethyl acetate) was added. The mixture was stirred at room temperature for 2 h. The mixture was concentrated under vacuum to give Compound I-3 without further purification as yellow solid.

Step d: Synthesis of N-((1S,2R)-2-(4-bromo-2-(methylcarbamoyl)-6-nitrophenyl)amino)cyclohexyl) iso-quinoline-4-carboxamide (Compound 2), N-((1S,2R)-(4-bromo-2-(methylcarbamoyl)-6-nitrophenyl)amino)cyclohexyl)-7-hydroxyisoquinoline-4-carboxamide (Compound 10), or N-((1S,2R)-2-((4-bromo-2-(methylcarbamoyl)-6-nitrophenyl)amino) cyclohexyl)-5-hydroxyisoquinoline-4-carboxamide (Compound 23)

Figure 4:
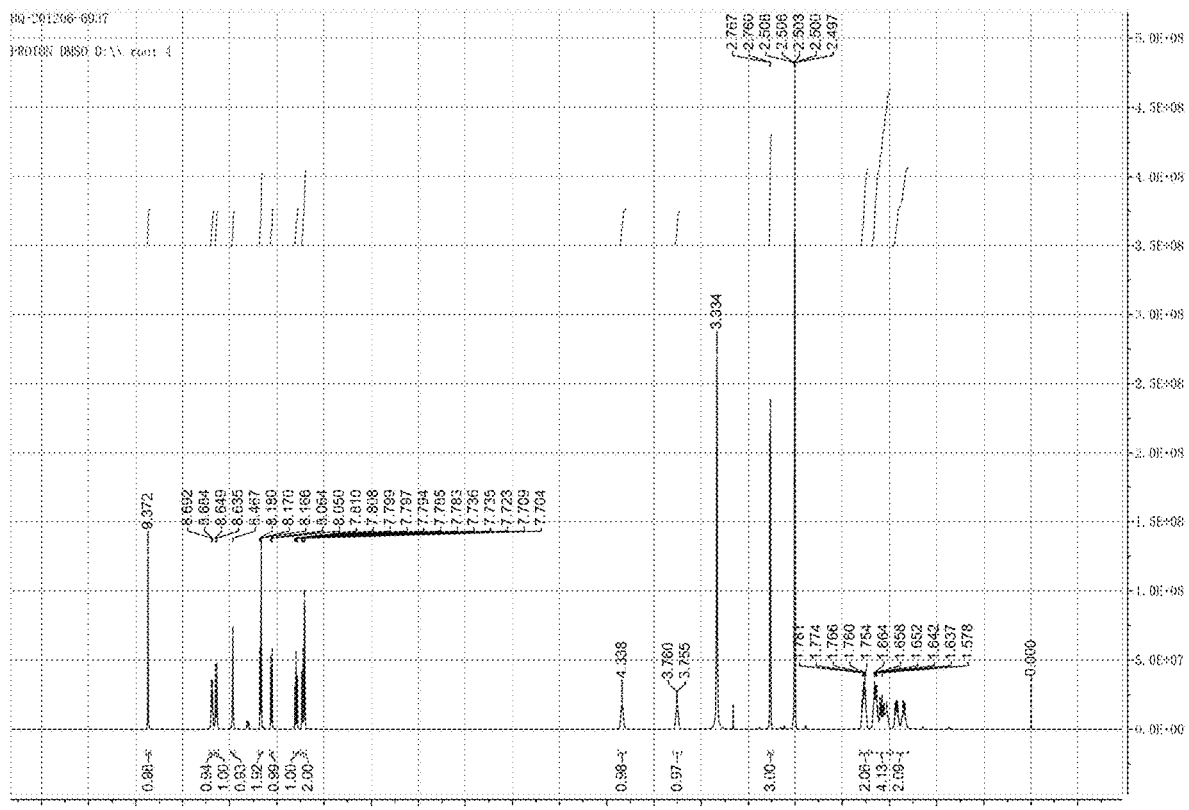
FIG. 4 shows the NMR characterization data of Compound 2.

A solution of corresponding isoquinoline-4-carboxylic acid (1 equiv.) and HATU (1.5 equiv.) in anhydrous DMF (6 mL) was stirred at room temperature. Then Compound 1-3 and DIPEA (5.0 equiv.) were added. The mixture was stirred at room temperature overnight. The mixture was extracted with ethyl acetate three times and the combined organic layer was washed with saturated brine solution. Then the organic phase was dried over anhydrous Na₂SO₄ and concentrated under vacuum. Finally, the mixture was purified by chromatography to give Compound 2, Compound 10, or Compound 23 as yellow solid (30%-80% yield):

Compound 2: ¹H NMR (600 MHz, DMSO-d₆) δ 9.37 (s, 1H), 8.69 (d, J=4.5 Hz, 1H), 8.64 (d, J=8.6 Hz, 1H), 8.47 (s, 1H), 8.19-8.15 (m, 2H), 8.06 (d, J=8.4 Hz, 1H), 7.80 (m, 1H), 7.75-7.69 (m, 2H), 4.34 (s, 1H), 3.76 (d, J=3.0 Hz, 1H), 2.76 (d, J=4.6 Hz, 3H), 1.81-1.72 (m, 2H), 1.69-1.49 (m, 4H), 1.46-1.30 (m, 2H). The NMR spectra data of Compound 2 is presented in FIG. 4.

Figure 5A:
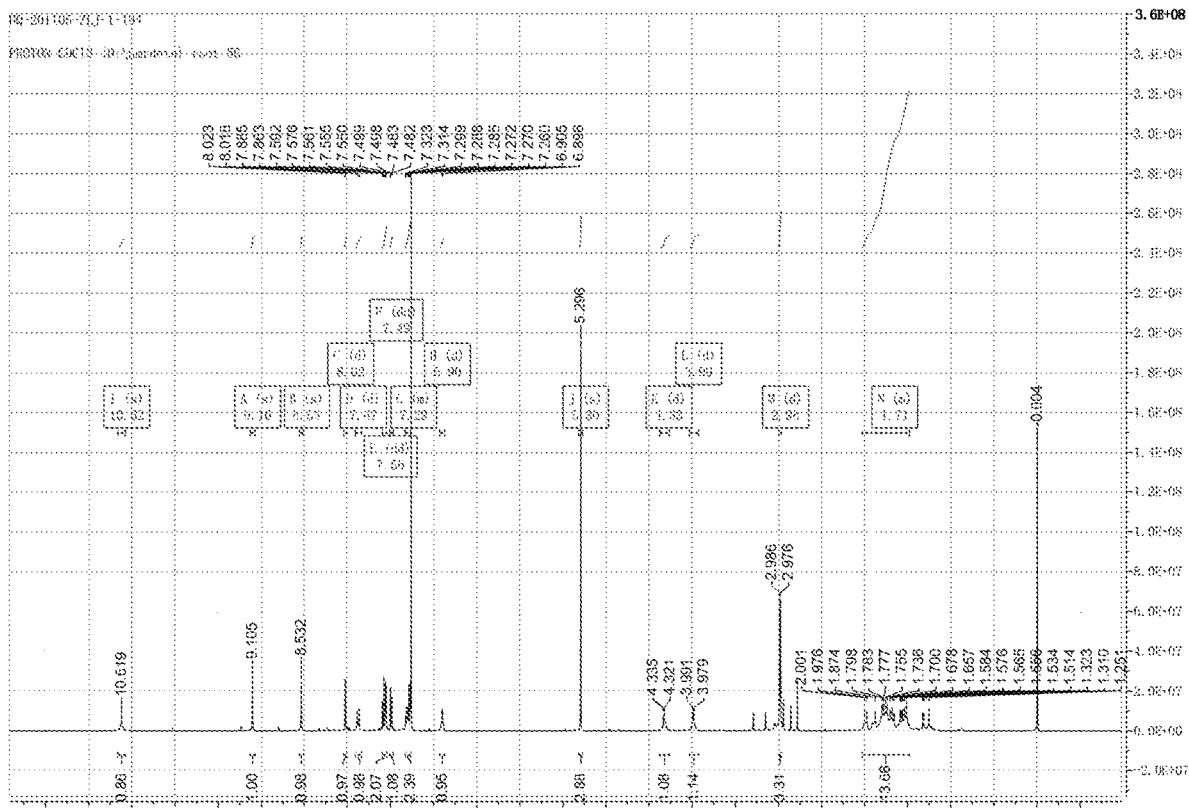
FIGS. 5A and 5B show the NMR (FIG. 5A) and mass spectrometry (FIG. 5B) characterization data of Compound 10.
Figure 5B:
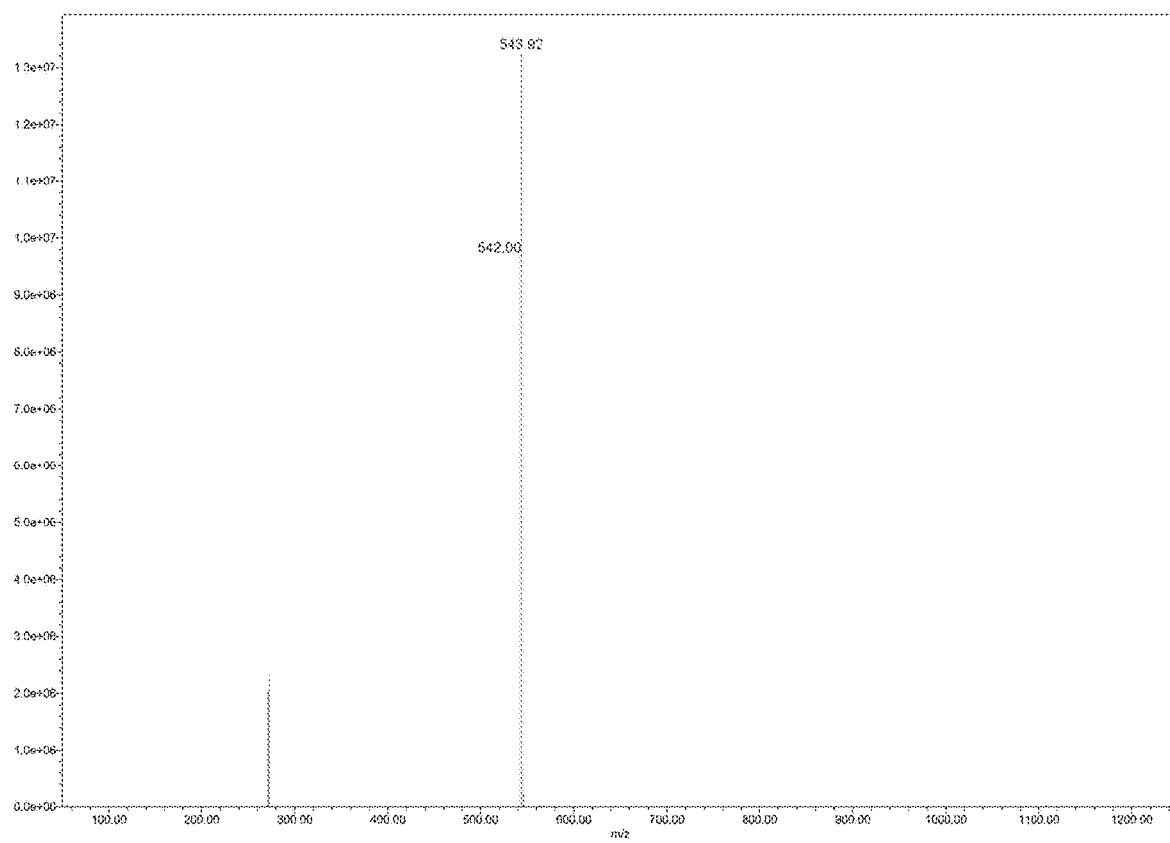

Compound 10: $^1$H NMR (500 MHz, CDCl$_3$) δ 10.62 (s, 1H), 9.10 (s, 1H), 8.53 (s, 1H), 8.02 (d, J=2.4 Hz, 1H), 7.87 (d, J=10.9 Hz, 1H), 7.56 (m, 2H), 7.49 (m, 1H), 7.33-7.27 (m, 2H), 6.90 (d, J=4.5 Hz, 1H), 4.33 (d, J=7.2 Hz, 1H), 3.99 (d, J=5.8 Hz, 1H), 2.98 (d, J=4.8 Hz, 3H), 2.03-1.48 (m, 8H). ESI-MS: m/z 542.00 [M+H]$^+$. The NMR and mass spectrometry characterization data of Compound 10 are presented in FIGS. 5A and 5B.

Figure 6A:
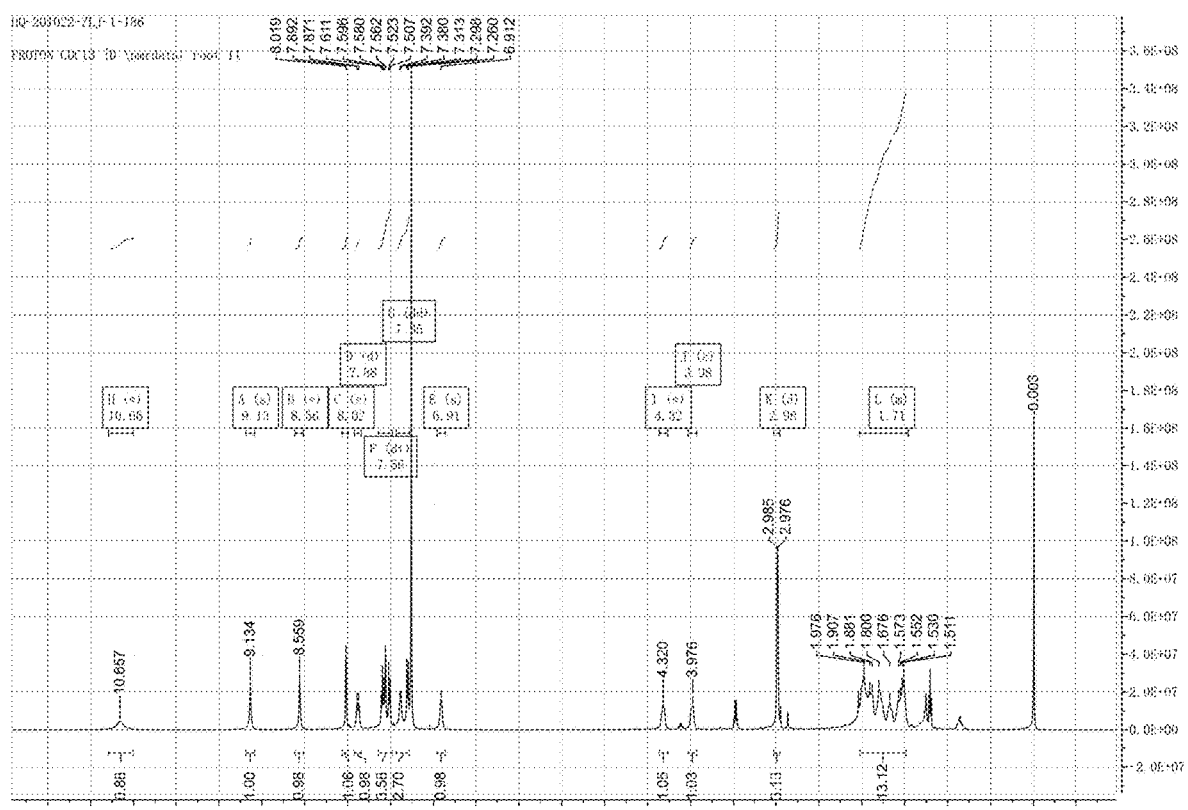
FIGS. 6A and 6B show the NMR (FIG. 6A) and mass spectrometry (FIG. 6B) characterization data of Compound 23.
Figure 6B:
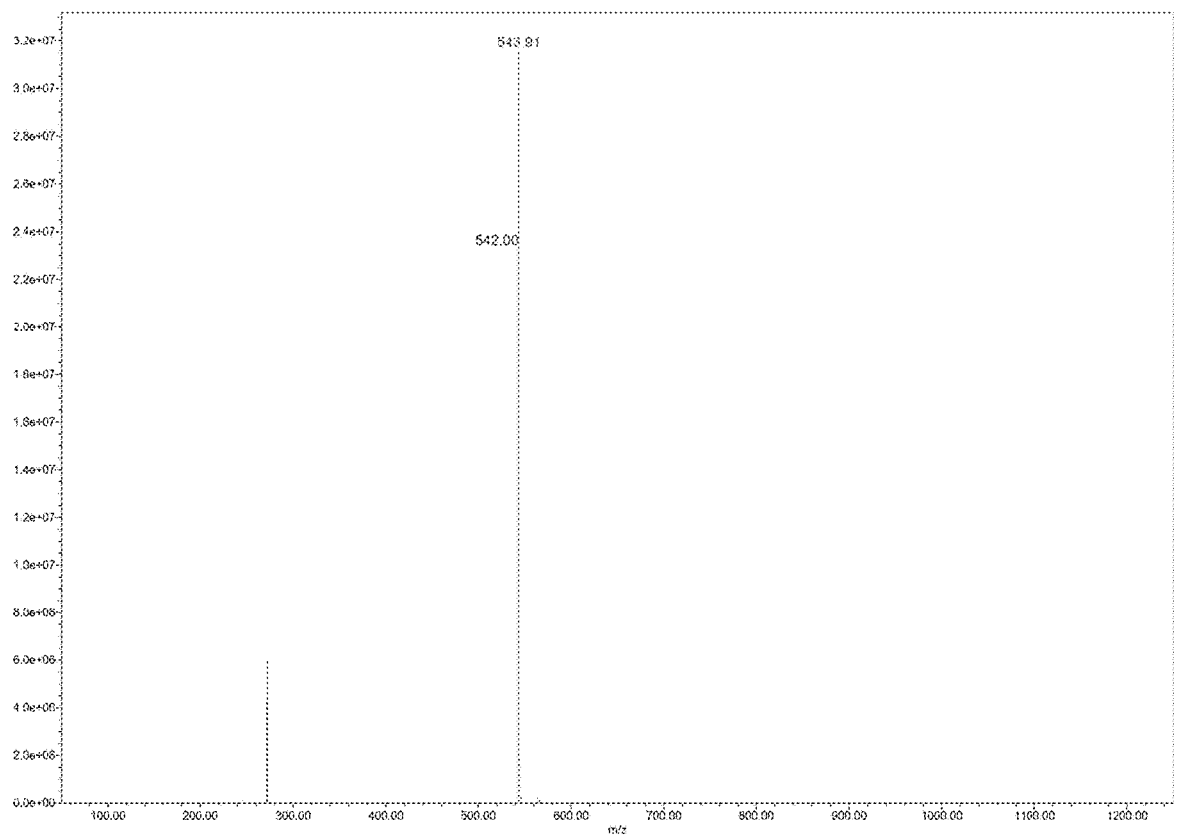

Compound 23: $^1$H NMR (500 MHz, CDCl$_3$) δ 10.66 (s, 1H), 9.13 (s, 1H), 8.56 (s, 1H), 8.02 (s, 1H), 7.88 (d, J=10.2 Hz, 1H), 7.56 (m, 3H), 7.35 (m, 2H), 6.91 (s, 1H), 4.32 (s, 1H), 3.98 (s, 1H), 2.98 (d, J=4.3 Hz, 3H), 2.03-1.46 (m, 8H). ESI-MS: m/z 542.00 [M+H]$^+$. The NMR and mass spectrometry characterization data of Compound 23 are presented in FIGS. 6A and 6B.

Compound 20

Compound 20 may be prepared by modifying the synthesis depicted in Scheme 1 and described above, i.e., by using tert-butyl (2-amino-3-hydroxycyclohexyl)carbamate or a stereoisomer thereof that is commercially available, in place of tert-butyl-2-aminocyclohexyl)carbamate (0.75 g, 3.5 mmol) or a corresponding stereoisomer thereof, in Step b, to react with Compound I-1 in the presence of DIPEA and dimethylformamide (DMF), at 80° C., and for 16 h. All other reagents and conditions are the same as the preparation of Compounds 2, 10, 18, 19, and 23 as described above.

Compounds 21 and 22

Compounds 21 and 22 may be prepared by modifying the synthesis depicted in Scheme 1, i.e., by using a different compound as a starting material (i.e., 5-bromo-2-fluoro-3-sulfobenzoic acid (for Compound 21) or 5-bromo-3-cyano-2-fluorobenzoic acid (for Compound 22) in place of 5-bromo-2-fluoro-3-nitrobenzoic acid, both of which are commercially available) in Step a. All other reagents and conditions are the same as the preparation of Compounds 2, 10, 18, 19, and 23 as described above.

Compound 1

Compound 1 or its analogues may be prepared using the procedures depicted in general Scheme 2. Preparation of Compound is shown in Scheme 3 below.

Scheme 2
General Steps a and b for Preparation of Compound 1 and Its Analogues

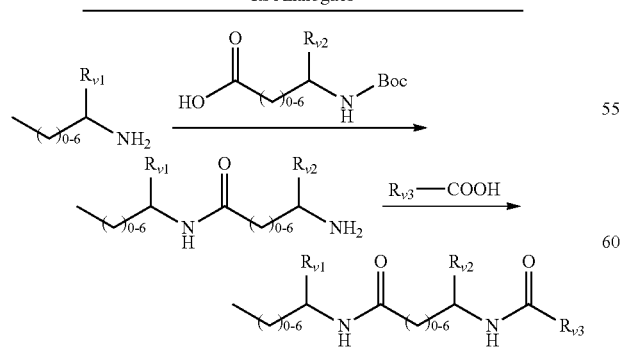

$R_{v1}, R_{v2}, R_{v3}$ = H, aliphatic chain or ring (including heteroaliphatic chain or ring).

Scheme 3: Prepration of Compound 1

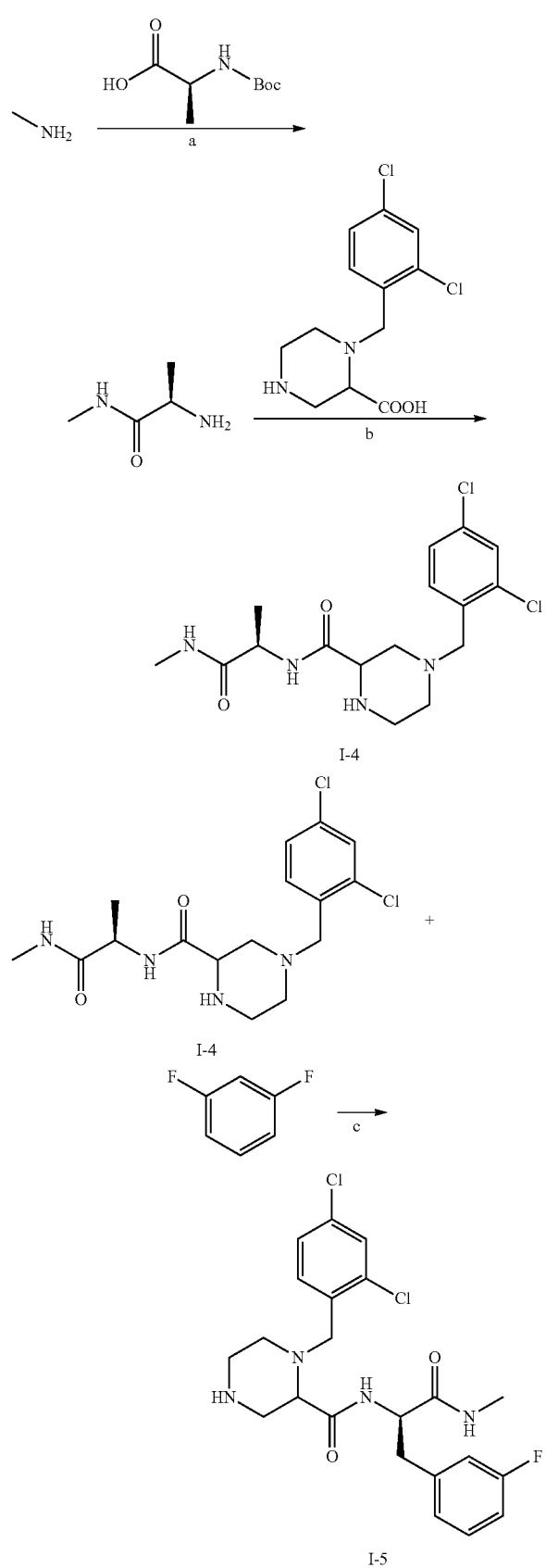

41

-continued

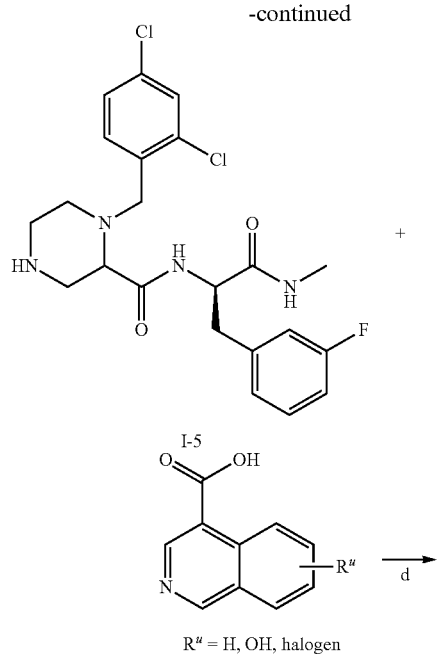

I-5

+

42

-continued

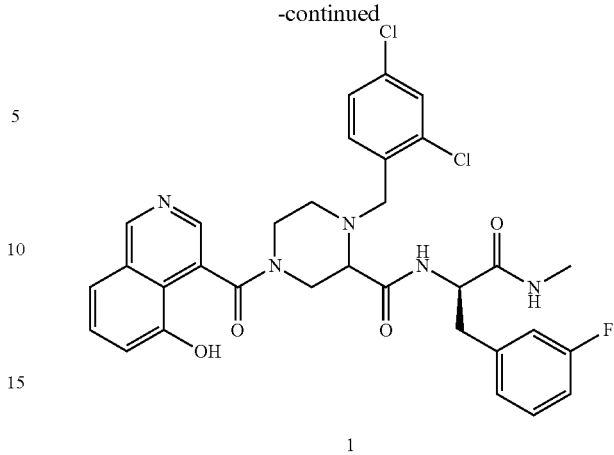

1

The reagents and conditions of Steps a to d as depicted in Scheme 3 are: (a) 3 M HCl·EA, DCM, 1 h; (b) HATU, DIPEA, DCM, 0° C., 2 h; (c) DIPEA, DMF, 80° C., 16 h; (d) HATU, DIPEA, DMF, room temperature, 12 h.

Compounds 7, 8, and 11

Compounds 7, 8, and 11 may be prepared using the procedure depicted in Scheme 4 below.

Scheme 4: Peparation of Compounds 7, 8, and 11

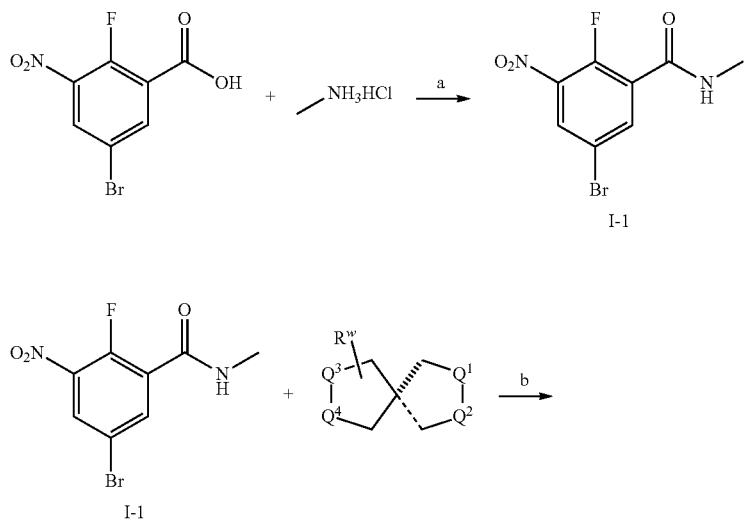

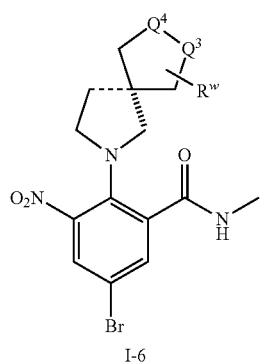

I-6

Compound 7: ⫶⫶⫶⫶⫶ is ⫶⫶⫶⫶⫶ ; ---- is ◢ ; $R^w$ = phenyl; $Q^1$ and $Q^4$ = N; $Q^2$ and $Q^3$ = C.

Compound 8: ⫶⫶⫶⫶⫶ is ⫶⫶⫶⫶⫶ ; ---- is ◢ ; $R^w$ = phenyl; $Q^1$ and $Q^3$ = N; $Q^2$ and $Q^4$ = C.

Compound 11: ⫶⫶⫶⫶⫶ is ◢ ; ---- is ⫶⫶⫶⫶⫶ ; $R^w$ = hydrogen; $Q^1$ and $Q^3$ = C; $Q^2$ and $Q^4$ = N.

-continued
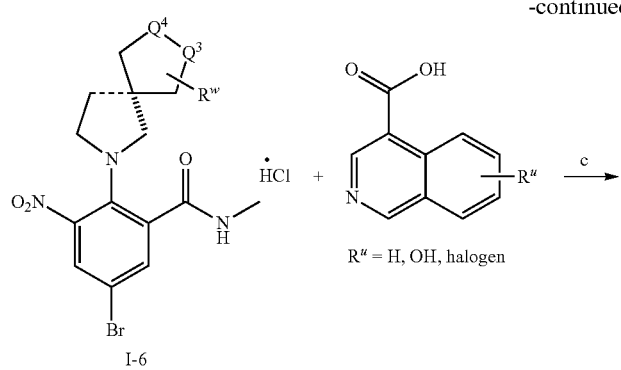
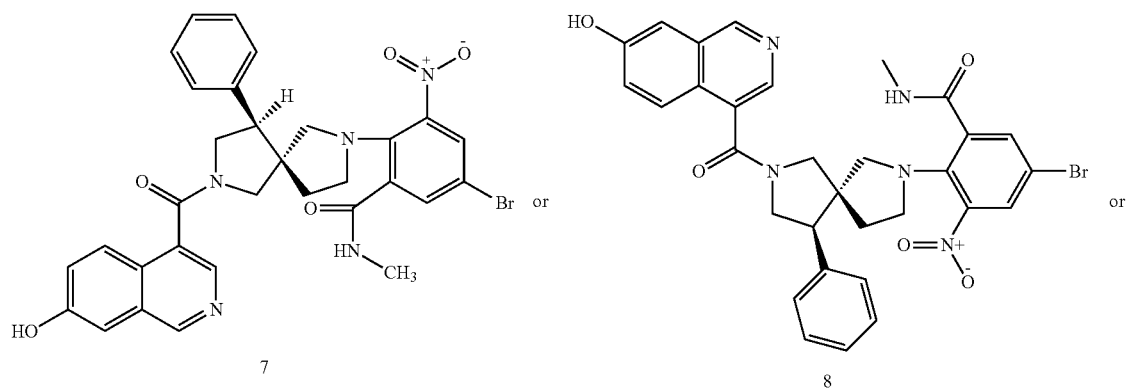
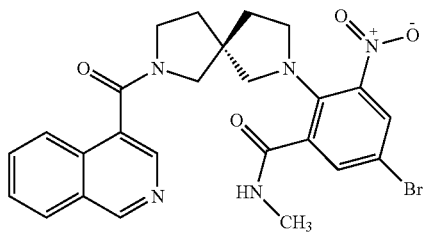
The reagents and conditions of Steps a to c as depicted in Scheme 4 are: (a) HATU, DIPEA, or DCM, 0° C., 2 h; (b) DIPEA, DMF, 80° C., 16 h; (c) HATU, DIPEA, DMF, room temperatue, 12 h.
Compounds 3 and 4
Compounds 3 and 4 may be prepared using the procedure depicted in Scheme 5 below.
Scheme 5: Preparation of Compounds 3 and 4
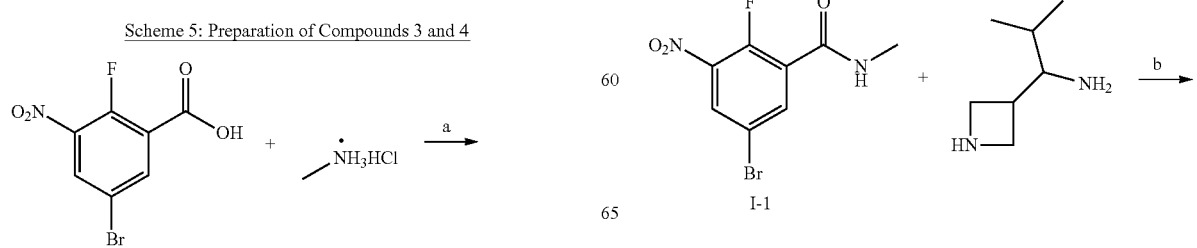
-continued -continued
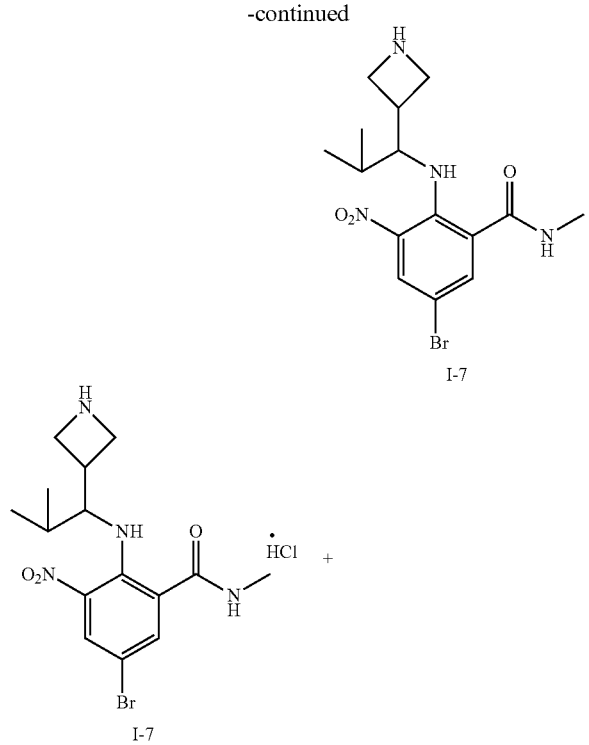
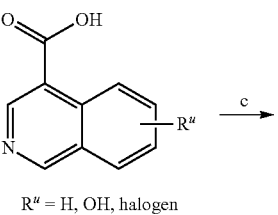
Compounds 5 and 6
Compounds 5 and 6 may be prepared using the procedure depicted in Scheme 6 below.
Scheme 6
Preparation of Compounds 5 and 6
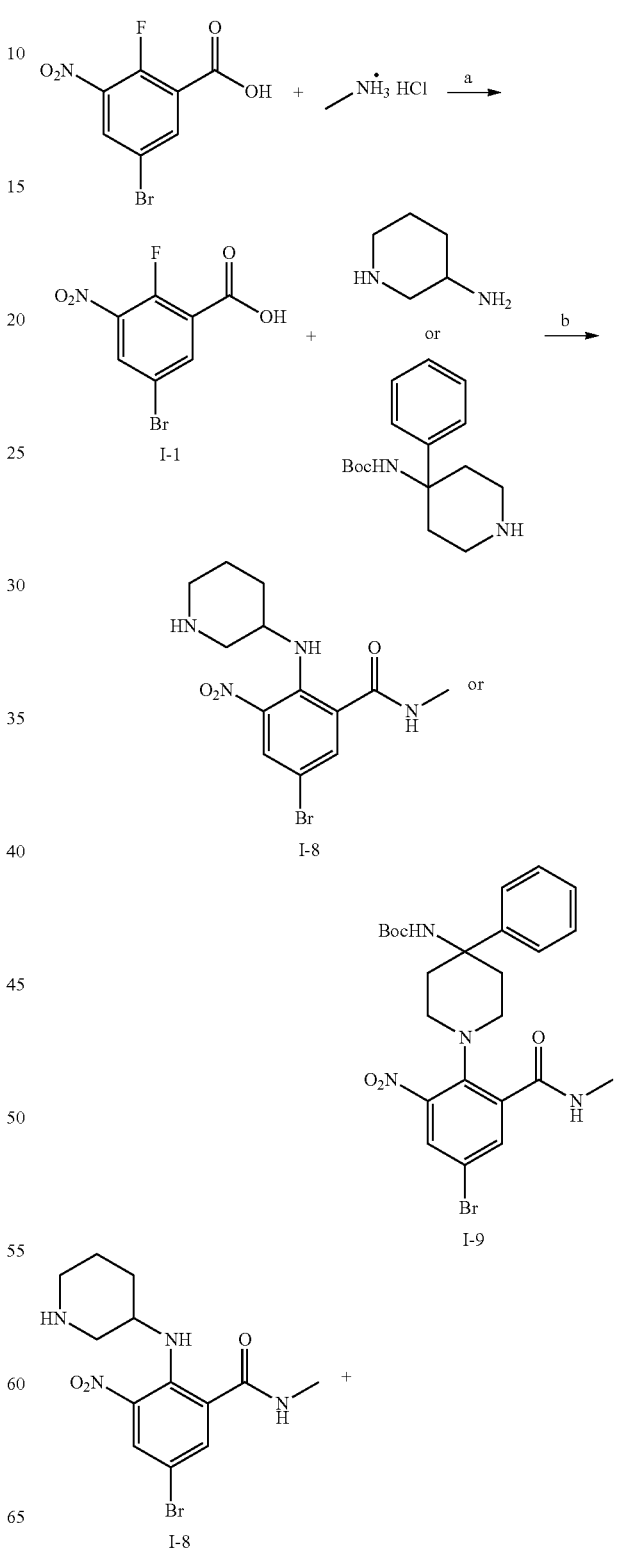
The reagents and conditions of Steps a to c as depicted in Scheme 5 are:
(a) HATU, DIPEA, or DCM, 0° C., 2 h; (b) DIPEA, DMF, 80° C., 16 h;
(c) HATU, DIPEA, DMF, room temperature, 12 h.

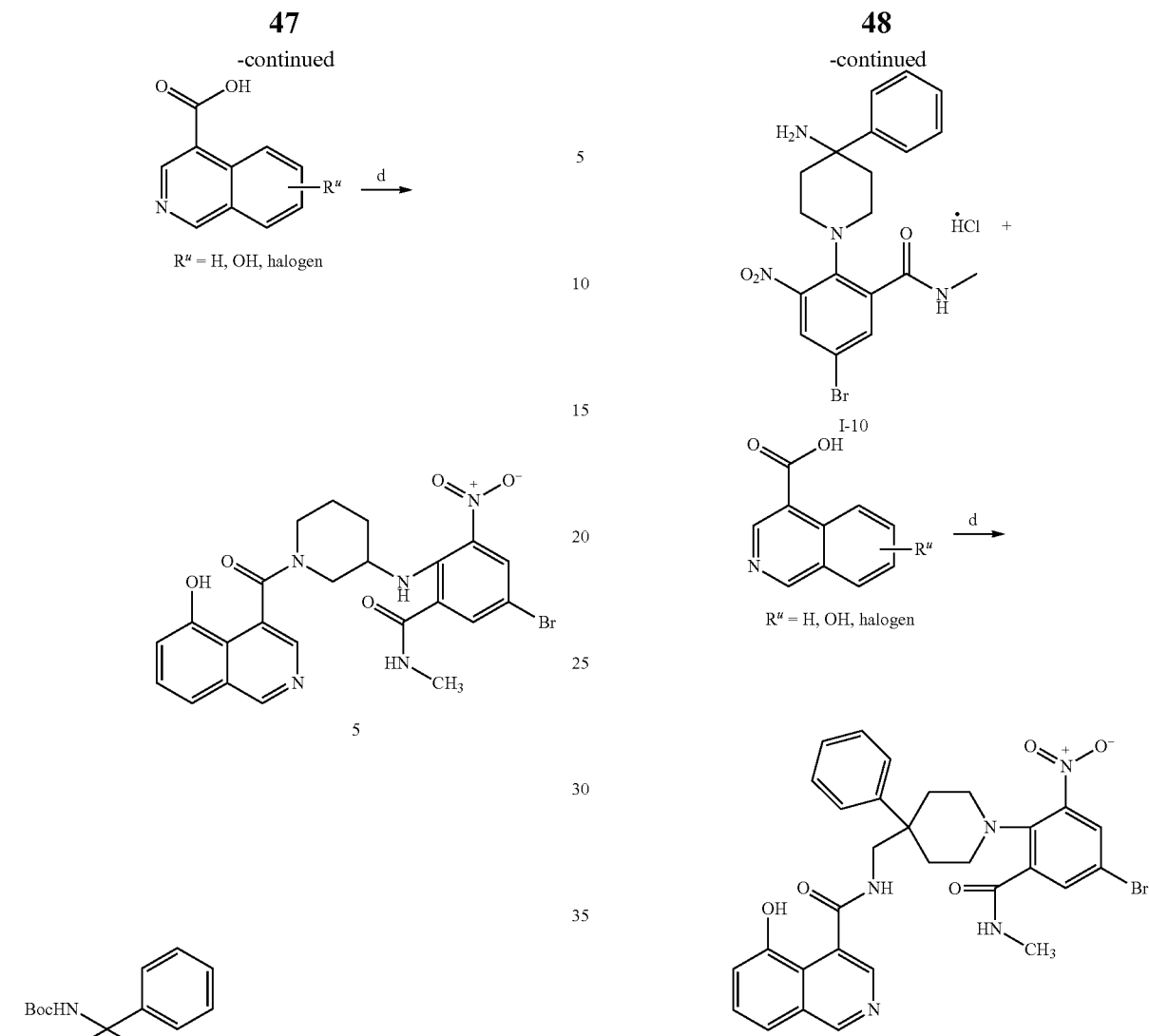
The reagents and conditions of Steps a to d as depicted in Scheme 6 are:
(a) HATU, DIPEA, or DCM, 0° C., 2 h; (b) DIPEA, DMF, 80° C., 16 h;
(c) 3M HCl·EA, DCM, 1 h; (d) HATU, DIPEA, DMF, room temperature, 12 h.
Compounds 9, 12, 15, and 16
Compounds 9, 12, 15, and 16 may be prepared using the procedure depicted in Scheme 7 below.
Scheme 7: Preparation of Compounds 9, 12, 15, and 16
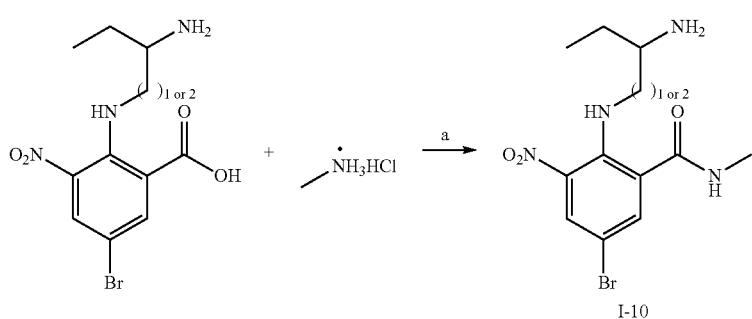

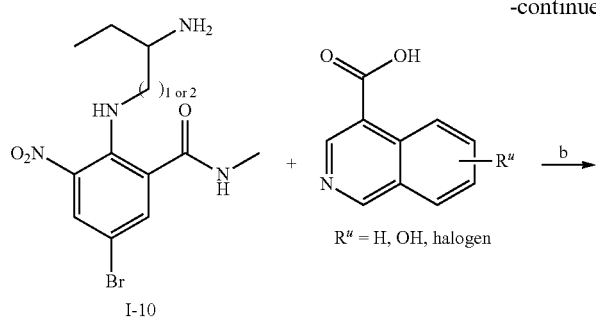
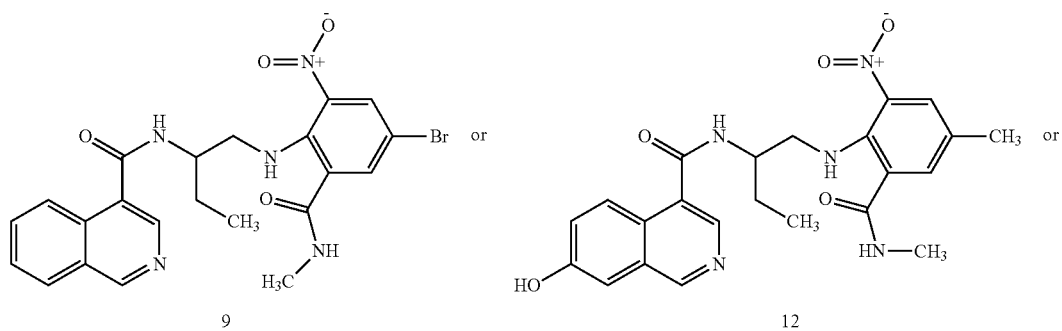
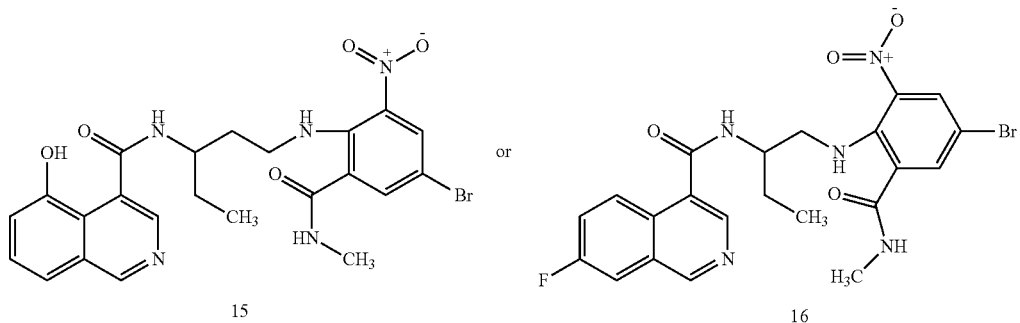
The reagents and conditions of Steps a and b as depicted in Scheme 7 and are: (a) HATU, DIPEA, or DCM, 0° C., 2 h; (b) HATU, DIPEA, DMF, room temperature, 12 h.
Compounds 13 and 17
Compounds 13 and 17 may be prepared using the procedure depicted in Scheme 8 below.
Scheme 8: Preparation of Compounds 13 and 17
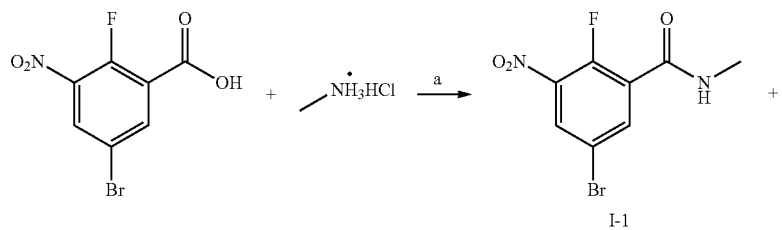

51
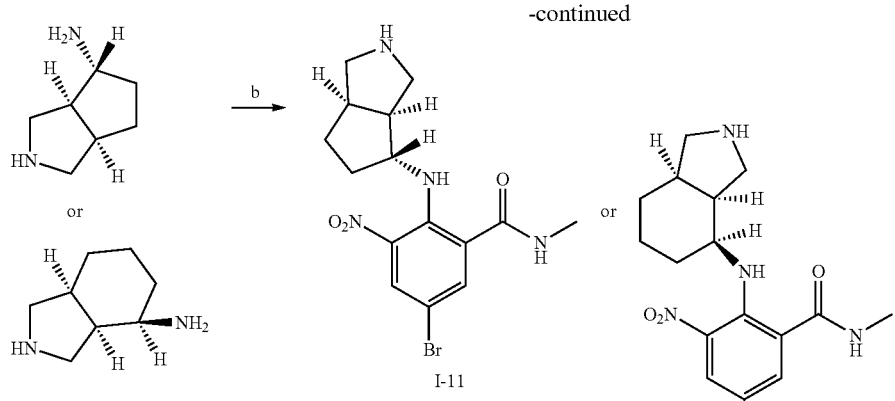
-continued
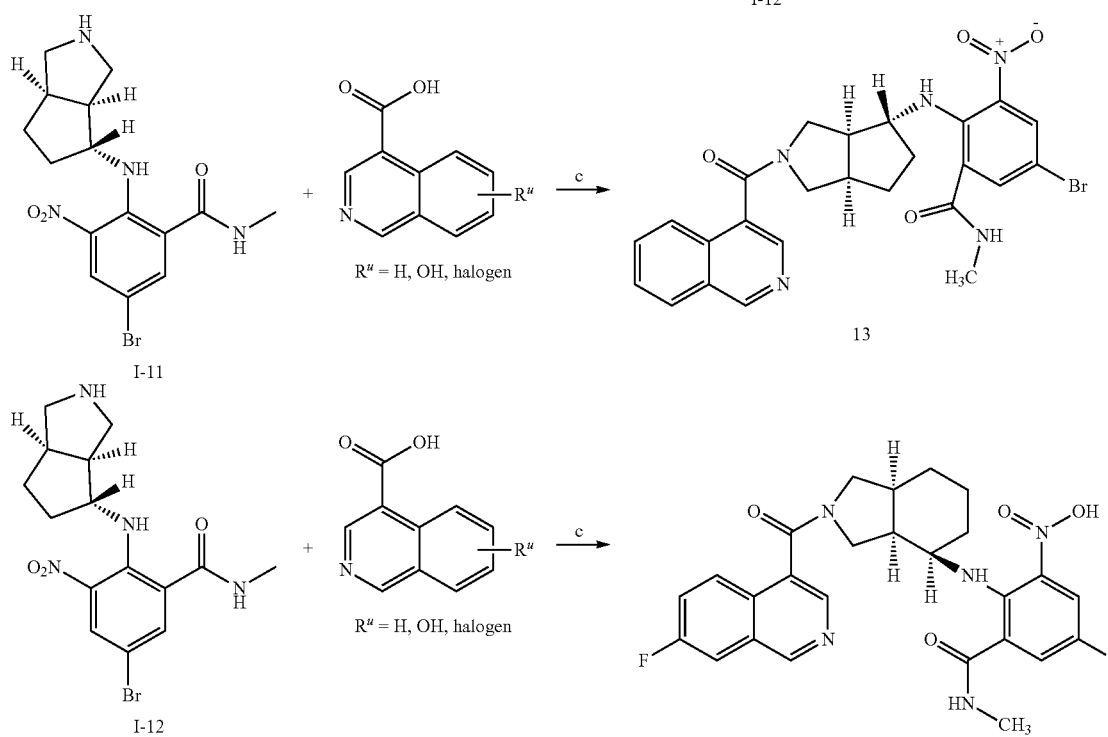
The reagents and conditions of Steps a to c as depicted in Scheme 8 are: (a) HATU, DIPEA, or DCM, 0° C., 2 h; (b) DIPEA, DMF, 80° C., 16 h; (c) HATU, DIPEA, DMF, room temperature, 12 h.
Compound 14
Compound 14 may be prepared using the procedure depicted in Scheme 9 below.
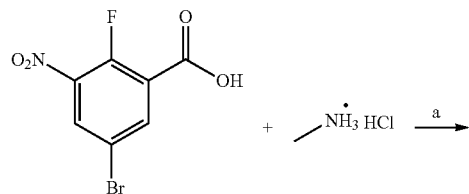
-continued
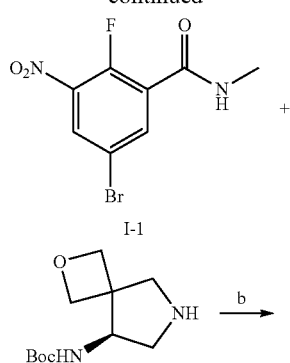

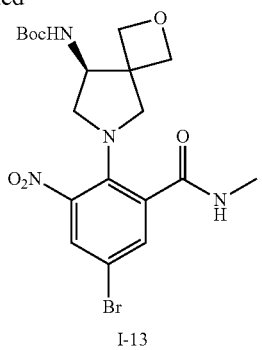

I-13

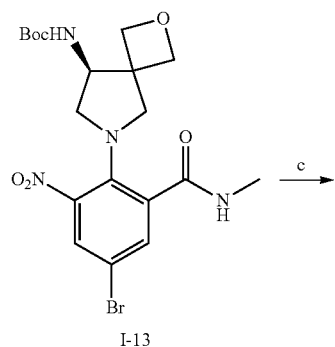

I-13

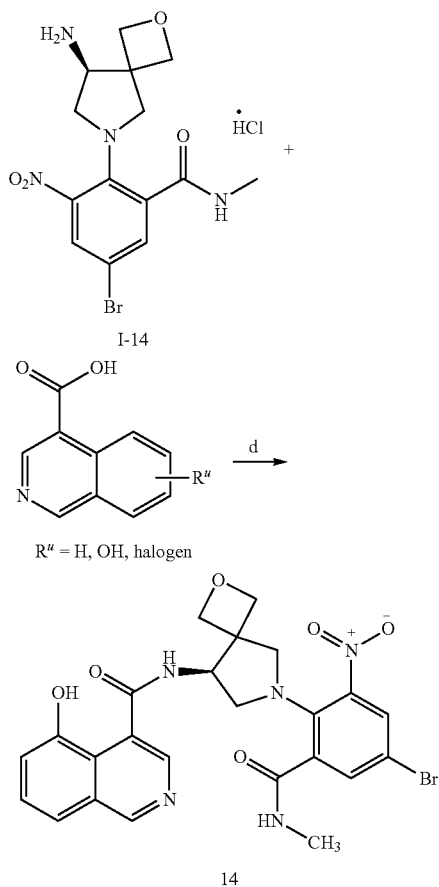

The reagents and conditions of Steps a to d as depicted in Scheme 9 are:
(a) HATU, DIPEA, or DCM, 0° C., 2 h; (b) DIPEA, DMF, 80° C., 16 h;
(c) 3M HCl•EA, DCM, 1 h; (d) HATU, DIPEA, DMF, room temperature, 12 h.

Example 3

In Vitro Enzymatic Assay Results

The ability of the three compounds in FIG. 1A to inhibit 3CLpro was tested using a fluorescence resonance energy transfer (FRET)-based continuous kinetic assay. A fluorescent peptide Dabcyl-KTSAVLQ↓SGFRKM-E(Edans) (SEQ ID NO: 4) was used as the substrate of purified 3CLpro. After cleavage by 3CLpro, the fragment SGFRKM-E (Edans) (SEQ ID NO: 5) was released and its fluorescence could be monitored with the excitation and emission wavelengths of 355 nm and 538 nm, respectively.

The final concentration of 3CLpro and the fluorogenic substrate (Dabcyl-KTSAVLQ↓SGFRKM-E(Edans) (SEQ ID NO: 4) were 100 nM and 100 μM, respectively. Briefly, 15 μL of the recombinant 3CLpro (0.4 μM) in the assay buffer (20 mM HEPES 7.4, 150 mM NaCl, 0.01% Triton X-100, 1 mM DTT) was incubated with 1.5 μL of a serial dilution of each compound at room temperature for 1 hour. A 384-well plate (Corning, CLS3575) was pre-warmed for 5 min at 30° C. Then 11 μL of the 3CLpro/inhibitor mixture was transferred to the 384-well plate. The reaction was initiated by adding 29 μL of the fluorogenic substrate (138 μM in the assay buffer). After that, the fluorescence signal was immediately measured every 1 min at 30° C. using a Thermol Varioskan LUX plate reader with 355 nm excitation and 538 nm emission.

Figure 7A:
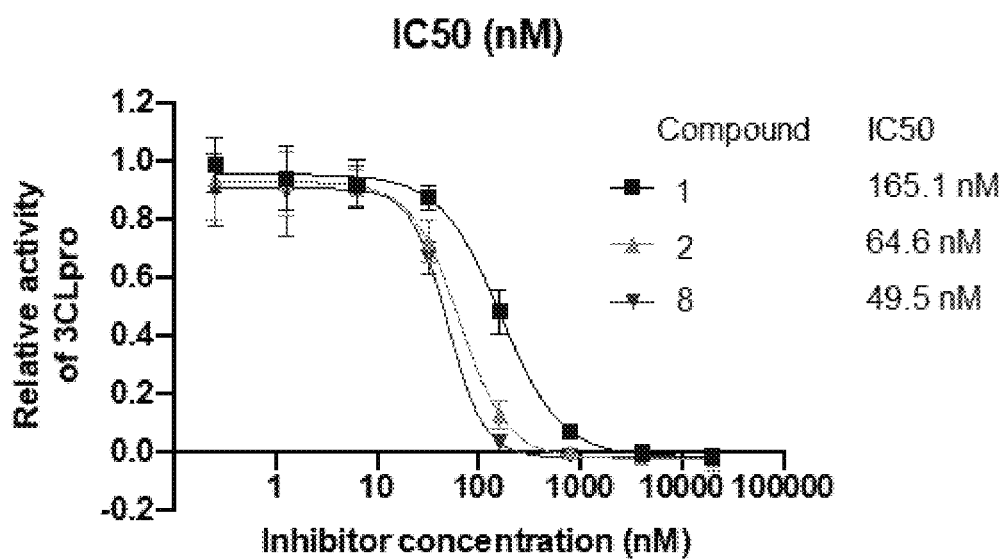
FIGS. 7A and 7B show the inhibitory activity of the compounds in FIG. 1 against SARS-CoV-2 3CLpro. Using an in vitro enzymatic assay, the half maximal inhibitory concentration ($IC_{50}$) of Compounds 1, 2, and 8 (FIG. 7A) and that of the two analogues of Compound 2, i.e., Compounds 10 and 23 (FIG. 7B) were measured.

The $IC_{50}$ of Compounds 1, 2, and 8 were 165.1 nM, 64.6 nM and 49.5 nM, respectively (FIG. 7A).

Figure 1B:
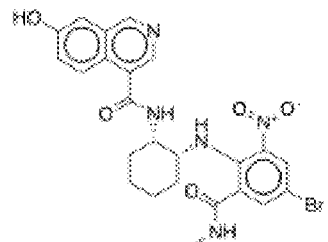
Figure 1B:
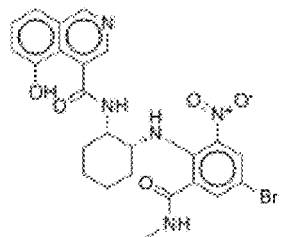
Figure 7B:
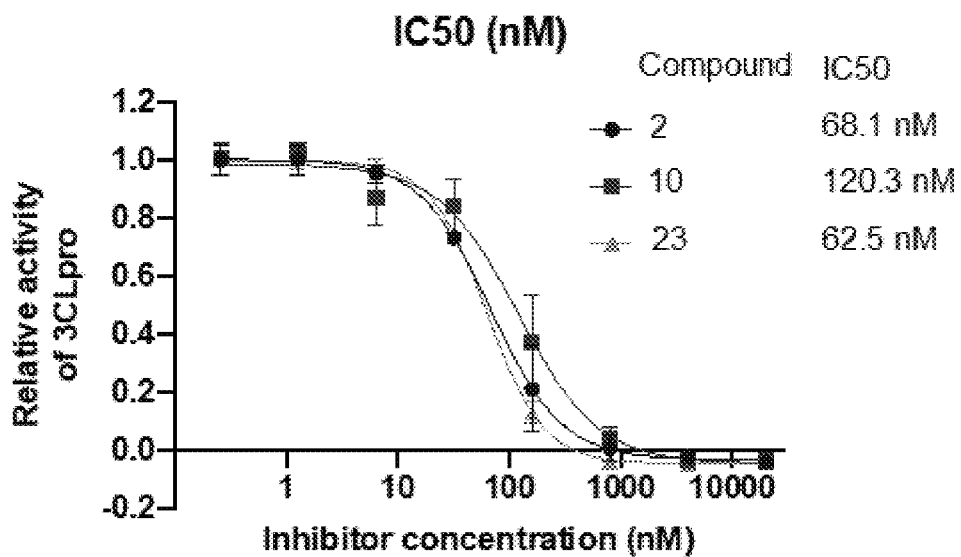

Two analogues of Compound 2, Compounds 10 and 23 (FIG. 1B), were synthesized and tested. One of the two analogues, Compound 23, showed an $IC_{50}$ similar to that of Compound 2 (FIG. 7B).

Example 4

Structural Biology Studies

To understand how the compounds as disclosed herein bind to and inhibit the enzymatic activity of 3CLpro, certain inhibitors were co-crystalized with SARS-CoV-2 3CLpro. The 3CLpro was over-expressed in *E. coli* and purified to homogeneity following a protocol used in the production of SARS-CoV 3CLpro (5). Before crystallization, a 10 mg/mL stock of the purified SARS-CoV-2 3CLpro in a buffer containing 20 mM HEPES pH 7.4 and 150 mM NaCl was incubated with 1.5 mM of the inhibitor at room temperature for 2 hours then the precipitate was removed by centrifugation. For crystallization, 0.2 μL of the 3CLpro/inhibitor complex was mixed with 0.2 μL of well buffers from commercially crystallization kits. Crystals were grown at 20° C. in a 96-well plate using the sitting-drop vapor-diffusion method. The diffraction data was collected at 100 K on a Rigaku XtaLAB Synergy Custom diffractometer and solved by molecular replacement using Phaser-MR (6) in the Phenix software suite (7). The crystal structure of the SARS-CoV-2 3CLpro (PDB code: 6Y2E) was used as the initial model. The 3CLpro/inhibitor complex structures were manually refined with Coot (8) and Phenix (7).

Figure 8A:
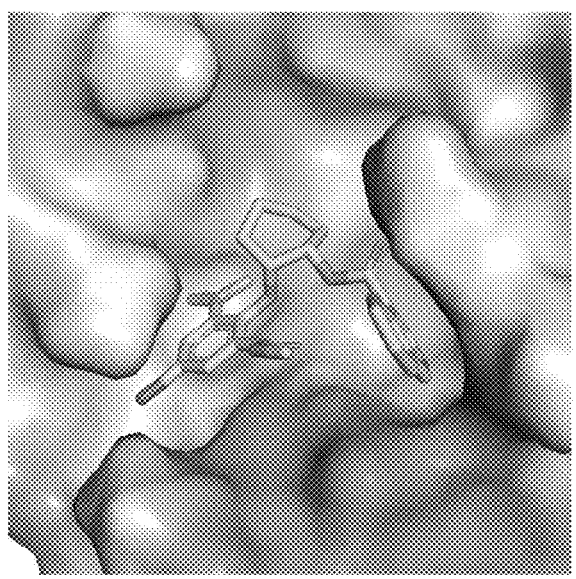
FIGS. 8A and 8B show the crystal structure of SARS-CoV-2 3CLpro in complex with Compound 2.
Figure 8B:
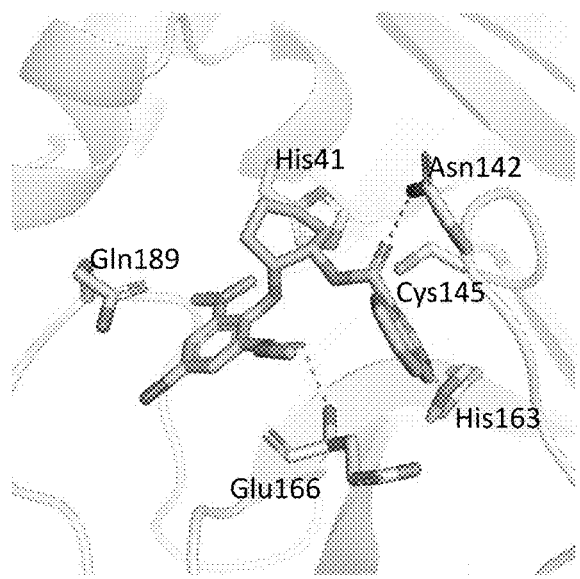

The crystal structure of 3CLpro/Compound 2 complex was determined by molecular replacement and refined to 1.83 Å. Compound 2 formed a 1:1 complex with 3CLpro. In the crystal structure, one molecule of Compound 2 bound into the catalytic pocket of 3CLpro thus competitively inhibiting the binding of 3CLpro substrates (FIG. 8A). Three hydrogen bonds formed between Compound 2 and 3CLpro:

the first one was between the nitrogen atom in the isoquinoline ring of Compound 2 and the side chain of His163; the second was between the carbonyl group attached to the isoquinoline ring and the side chain of Asn142; and the third one was between the carbonyl oxygen in the methylcarbamoyl group of Compound 2 and the main chain amide of Glu166 (FIG. 8B). In addition to hydrogen bonding, the amino-π interaction between phenyl ring and the side chain of Gln189 also contributed to the potency of Compound 2; the strong electron-withdrawing ability of the nitro group made the aromatic ring positive-charged therefore might have significantly enhanced this interaction (9).

Figure 9A:
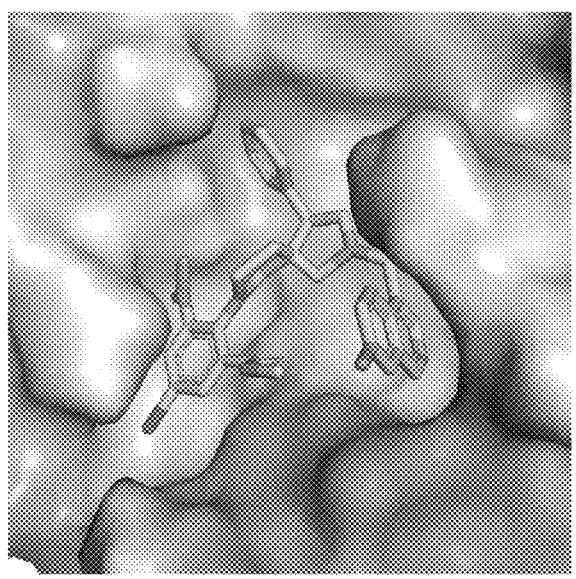
FIGS. 9A and 9B show the crystal structure of SARS-CoV-2 3CLpro in complex with Compound 8.
Figure 9B:
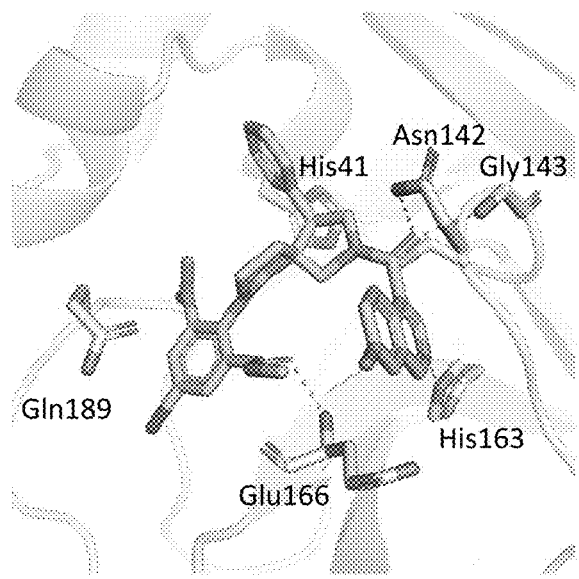

The crystal structure of 3CLpro/Compound 8 complex was refined to 1.9 Å (FIG. 9A). Compound 8 was found to bind to 3CLpro similar to that of Compound 2 (FIG. 9B), indicating that the isoquinoline ring and the nitrophenyl ring are important for the interactions with 3CLpro, while the linker region between them keep them at the appropriate positions.

Figure 10A:
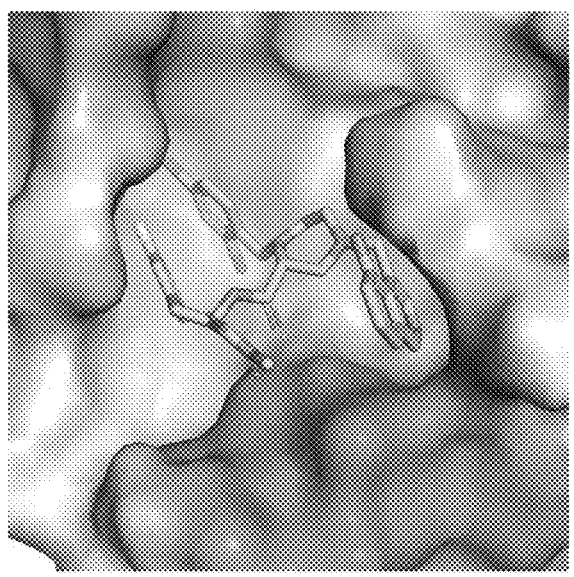
FIGS. 10A and 10B show the crystal structure of SARS-CoV-2 3CLpro in complex with Compound 1.
Figure 10B:
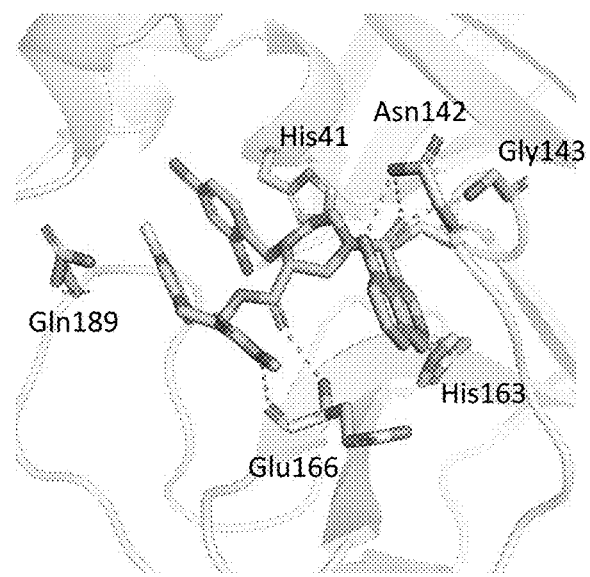

The crystal structure of 3CLpro/Compound 1 complex was refined to 1.69 Å (FIG. 10A). The isoquinoline ring of Compound 1 binds into a pocket in 3CLpro surrounded by residues Asn142, His163 and Glu166, similarly to the binding of the isoquinoline ring of Compound 2. The hydroxyl group at the isoquinoline ring forms an additional hydrogen bond with the side chain of Asn142, contributing to the binding between Compound 1 and 3CLpro. The dichlorobenzyl group interacts with the side chain of His41 through π-π stacking.

Example 5

Anti-SARS-CoV-2 Activity of 3Clpro Inhibitors in Cellular Assays

The anti-SARS-CoV-2 activities of Compounds 1, 2, and 8 were measured in three different cell lines, including the A549, VeroE6 and Calu3 cell lines. A nanoluciferase severe respiratory syndrome coronavirus 2 (SARS-CoV-2-Nluc) generated by incorporating the nanoluciferase gene into the SARS-CoV-2 genome was used to infect the host cells, then the antiviral assays were carried out following the methods in (10). The cytotoxicity assay was also carried following the methods in (10).

Figure 11A:
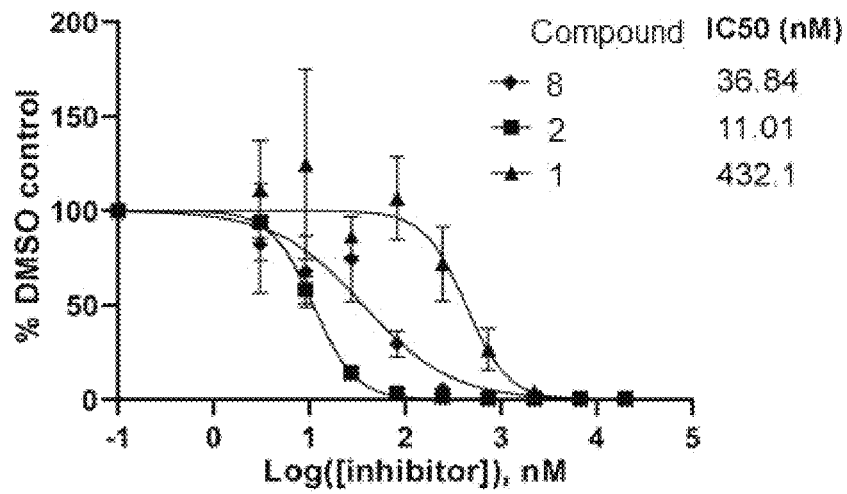
FIGS. 11A and 11B show the anti-SARS-CoV-2 activity (FIG. 11A) and the cytotoxic effects (FIG. 11B) of three inhibitors in A549 cells.
Figure 11B:
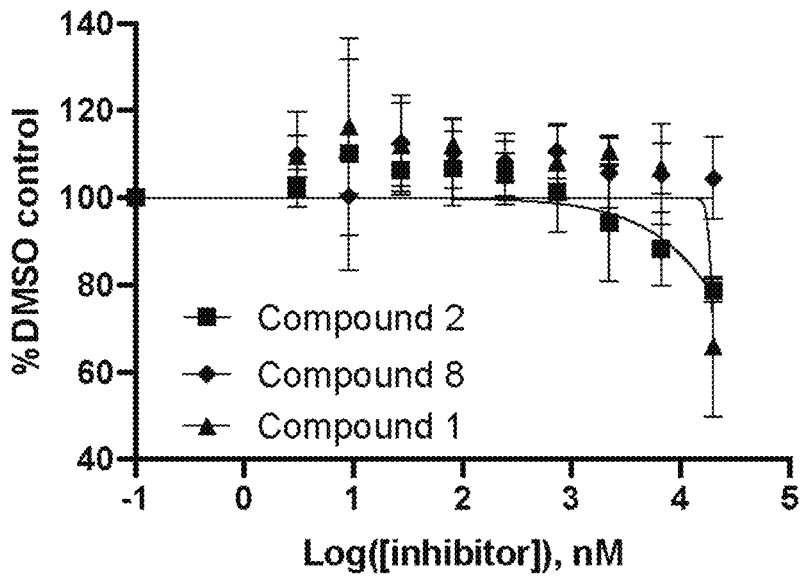

A549 is a carcinomic human alveolar epithelial cell line. The most potent compound in A549 cells was Compound 2, followed by Compound 8 and Compound 1, with their $IC_{50}$ values of 12.43 nM, 38.77 nM and 848.0 nM, respectively (FIG. 11A). The cytotoxic effects of these compounds in A549 cells were also evaluated. The cells were treated with serially diluted stock solutions of these compounds for three days. The 50% cytotoxic concentrations ($CC_{50}$) of all of these compounds were greater than 20 µM (FIG. 11B).

Figure 12A:
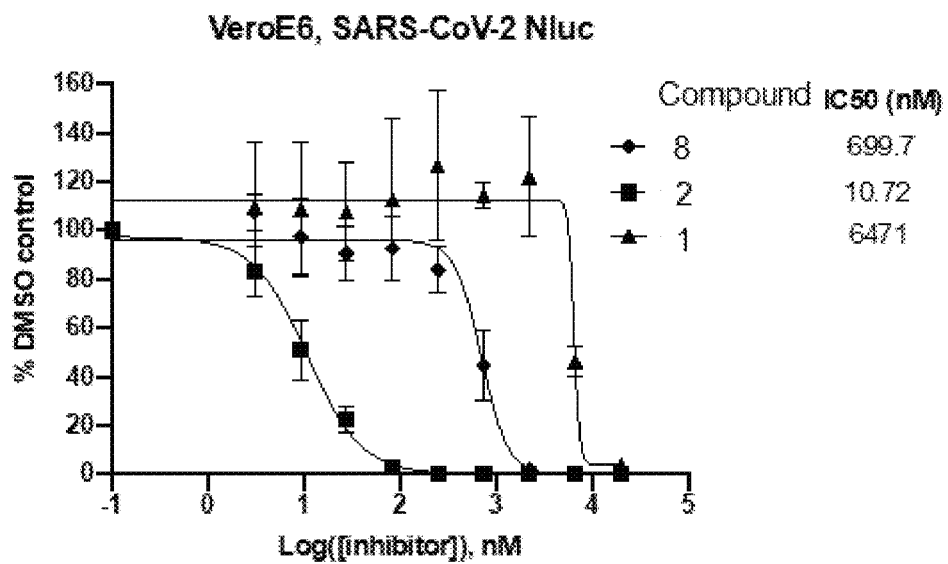
FIGS. 12A and 12B show the anti-SARS-CoV-2 activity of three inhibitors in VeroE6 cells (FIG. 12A) and in Calu3 cells (FIG. 12B).
Figure 12B:
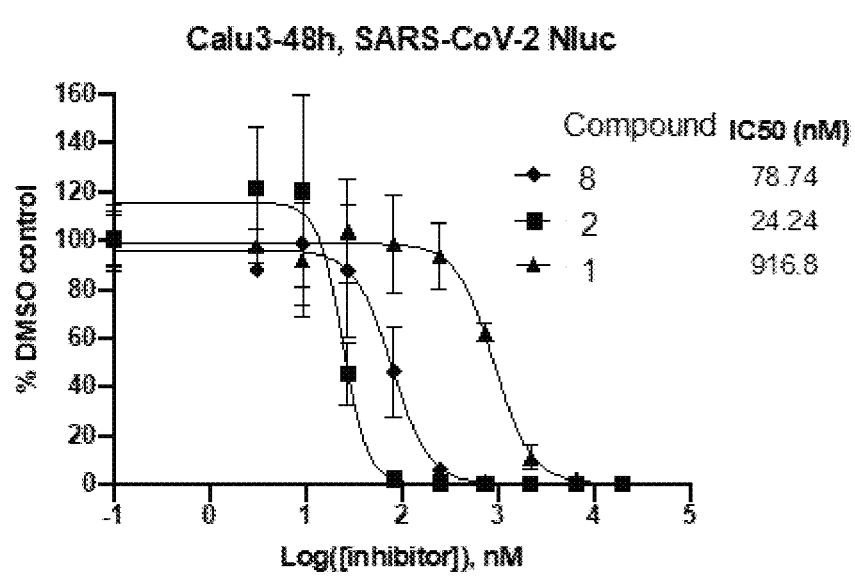

The 3CLpro inhibitors, especially Compound 2, also showed high potency to inhibit SARS-CoV-2 replication in VeroE6 cells (FIG. 12A) and in Calu3 cells (FIG. 12B).

The above testing results showed that several non-covalent small molecule inhibitors of SARS-CoV-2 3CLpro, e.g., Compounds 1, 2, and 8, effectively blocked coronavirus replication in host cells. For instance, Compound 2, showed high potency in both cell-free enzymatic assay and in cell-based anti-SARS-CoV-2 assays. Compound 2 and its analogues such as but not limited to Compounds 10, 18, and 23, can be used for the treatment of a disease or a symptom of a disease caused by a coronavirus, such as COVID-19.

Sequence analysis shows that the residues surrounding Compound 2 are highly conserved in SARS-CoV 3CLpro and MERS-CoV 3CLpro (FIG. 13 and Table 2), indicating that Compound 2 and its analogues can be pan-inhibitors of coronavirus 3CL proteases.

TABLE 2

Examples of coronavirus 3CLpro protein sequences

| SEQ ID NO | Description | Sequence |
|---|---|---|
| SEQ ID NO: 1 (SARS-CoV-2 3CLpro) | YP_009725301.1 3C-like proteinase [Severe acute respiratory syndrome coronavirus 2] | SGFRKMAFPSGKVEGCMVQVTCGTTTLNGLWLD DVVYCPRHVICTSEDMLNPNYEDLLIRKSNHNFLV QAGNVQLRVIGHSMQNCVLKLKVDTANPKTPKY KFVRIQPGQTFSVLACYNGSPSGVYQCAMRPNFTI KGSFLNGSCGSVGFNIDYDCVSFCYMHHMELPTG VHAGTDLEGNFYGPFVDRQTAQAAGTDTTITVNV LAWLYAAVINGDRWFLNRFTTTLNDFNLVAMKY NYEPLTQDHVDILGPLSAQTGIAVLDMCASLKELL QNGMNGRTILGSALLEDEFTPFDVVRQCSGVTFQ |
| SEQ ID NO: 2 (SARS-CoV 3CLpro) | NP_828863.1 nsp5 [SARS coronavirus Tor2] | SGFRKMAFPSGKVEGCMVQVTCGTTTLNGLWLD DTVYCPRHVICTAEDMLNPNYEDLLIRKSNHSFLV QAGNVQLRVIGHSMQNCLLRLKVDTSNPKTPKYK FVRIQPGQTFSVLACYNGSPSGVYQCAMRPNHTIK GSFLNGSCGSVGFNIDYDCVSFCYMHHMELPTGV HAGTDLEGKFYGPFVDRQTAQAAGTDTTITLNVL AWLYAAVINGDRWFLNRFTTTLNDFNLVAMKYN YEPLTQDHVDILGPLSAQTGIAVLDMCAALKELLQ NGMNGRTILGSTILEDEFTPFDVVRQCSGVTFQ |
| SEQ ID NO: 3 (MERS-CoV 3CLpro) | YP_009047217.1 nsp5 protein [Middle East respiratory syndrome-related coronavirus] | SGLVKMSHPSGDVEACMVQVTCGSMTLNGLWLD NTVWCPRHVMCPADQLSDPNYDALLISMTNHSFS VQKHIGAPANLRVVGHAMQGTLLKLTVDVANPST PAYTFTTVKPGAAFSVLACYNGRPTGTFTVVMRP NYTIKGSFLCGSCGSVGYTKEGSVINFCYMHQMEL ANGTHTGSAFDGTMYGAFMDKQVHQVQLTDKY CSVNVVAWLYAAILNGCAWFVKPNRTSVVSFNE WALANQFTEFVGTQSVDMLAVKTGVAIEQLLYAI QQLYTGFQGKQILGSTMLEDEFTPEDVNMQIMGV VMQ |

REFERENCES

1. A. R. Fehr, S. Perlman, Coronaviruses: an overview of their replication and pathogenesis. *Methods Mol. Biol.* 1282, 1-23 (2015).
2. P. Zhou et al., A pneumonia outbreak associated with a new coronavirus of probable bat origin. *Nature.* 579, 270-273 (2020).
3. J. Lei, Y. Kusov, R. Hilgenfeld, Nsp3 of coronaviruses: Structures and functions of a large multi-domain protein. *Antiviral Res.* 149, 58-74 (2018).
4. T. Pillaiyar, M. Manickam, V. Namasivayam, Y. Hayashi, S.-H. Jung, An Overview of Severe Acute Respiratory Syndrome-Coronavirus (SARS-CoV) 3CL Protease Inhibitors: Peptidomimetics and Small Molecule Chemotherapy. *J. Med. Chem.* 59, 6595-6628 (2016).
5. X. Xue et al., Production of authentic SARS-CoV M(pro) with enhanced activity: application as a novel tag-cleavage endopeptidase for protein overproduction. *J. Mol. Biol.* 366, 965-975 (2007).
6. A. J. McCoy et al., Phaser crystallographic software. *J Appl Crystallogr.* 40, 658-674 (2007).
7. D. Liebschner et al., Macromolecular structure determination using X-rays, neutrons and electrons: recent developments in Phenix. *Acta Crystallogr D Struct Biol.* 75, 861-877 (2019).
8. P. Emsley, B. Lohkamp, W. G. Scott, K. Cowtan, Features and development of Coot. *Acta Crystallogr. D Biol. Crystallogr.* 66, 486-501 (2010).
9. H. Wang, W. Wang, W. J. Jin, σ-Hole Bond vs π-Hole Bond: A Comparison Based on Halogen Bond. *Chem. Rev.* 116, 5072-5104 (2016).
10. X. Xie et al., A nanoluciferase SARS-CoV-2 for rapid neutralization testing and screening of anti-infective drugs for COVID-19. *Nat Commun.* 11, 5214-11 (2020).

One skilled in the art will readily recognize from the disclosure and claims that various changes, modifications, and variations can be made therein without departing from the spirit and scope of the disclosure as defined in the following claims.

---

The invention claimed is:

1. A compound of the following structural formula IIIa:

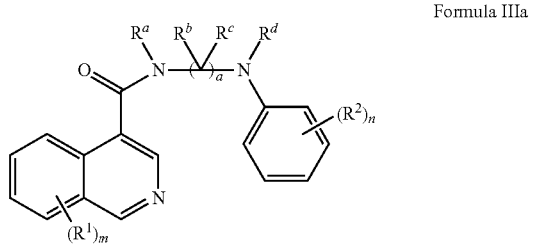

Formula IIIa a tautomer thereof, a deuterated derivative of the compound or the tautomer, or a pharmaceutically acceptable salt of the foregoing, wherein:

$R^a$ and $R^d$, for each occurrence, are each independently hydrogen or $C_1$-$C_4$ alkyl;

$R^b$ and $R^c$, for each occurrence, are each independently hydrogen or $C_1$-$C_4$ alkyl that is optionally substituted with 1 to 3 groups selected from halogen, cyano, and $C_1$-$C_4$ alkoxy;

a is an integer selected from 1, 2, 3, and 4;

$R^1$ and $R^2$, for each occurrence, are each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —NO$_2$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, —S(=O)$_3^-$, $C_3$-$C_{12}$ carbocyclyl, 3 to 12-membered heterocyclyl, phenyl, and 5 to 10-membered heteroaryl; wherein:

the $C_1$-$C_6$ alkyl, the $C_2$-$C_6$ alkenyl, and the $C_1$-$C_6$ alkoxy of any one of $R^1$ and $R^2$ and the $C_1$-$C_6$ alkyl of —C(=O)($C_1$-$C_6$ alkyl) are each optionally substituted with 1 to 3 groups selected from halogen, cyano, —C(=O)R$^s$, —C(=O)OR$^s$, —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, $C_3$-$C_6$ cycloalkyl, and phenyl that is optionally substituted with 1 to 3 halogen atoms;

the $C_3$-$C_{12}$ carbocyclyl, the 3 to 12-membered heterocyclyl, the phenyl, and the 5 to 10-membered heteroaryl of any one of $R^1$ and $R^2$ are each optionally substituted with 1 to 3 groups selected from halogen, cyano, $C_1$-$C_4$ alkyl, —NR$^p$R$^q$, and —OR$^s$;

$R^p$, $R^q$, and $R^r$, for each occurrence, are each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$ is optionally substituted with 1 to 3 groups selected from halogen, cyano, and —OH;

$R^s$, for each occurrence, is each independently selected from hydrogen, $C_1$-$C_4$ alkyl, and $C_3$-$C_6$ cycloalkyl;

w is an integer selected from 1 and 2; and $R^1$, for each occurrence, may be attached to any of the ring atoms of the isoquinoline in formula IIIa as long as valency permits; and m is an integer selected from 0, 1, 2, 3, 4, 5, and 6; and n is an integer selected from 1, 2, 3, 4, and 5.

2. The compound according to claim 1, wherein the compound is of the following structural formula IVa:

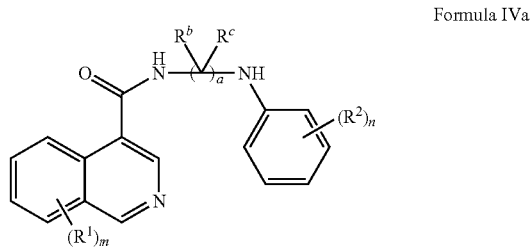

Formula IVa a tautomer thereof, a deuterated derivative of the compound or the tautomer, or a pharmaceutically acceptable salt of the foregoing; wherein:

$R^b$ and $R^c$, for each occurrence, are each independently hydrogen or $C_1$-$C_2$ alkyl that is optionally substituted with 1 to 3 groups selected from halogen, cyano, and $C_1$-$C_4$ alkoxy; and a is an integer selected from 1 and 2.

3. The compound according to claim 1, wherein the compound is of the following structural formula Va:

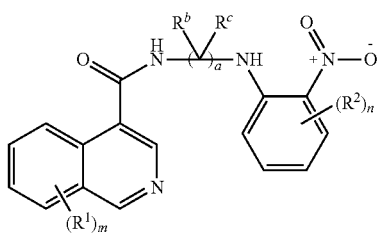

Formula Va a tautomer thereof, a deuterated derivative of the compound or the tautomer, or a pharmaceutically acceptable salt of the foregoing; wherein n is an integer selected from 1, 2, 3, and 4.

4. A compound of the following structural formula IIIb-1:

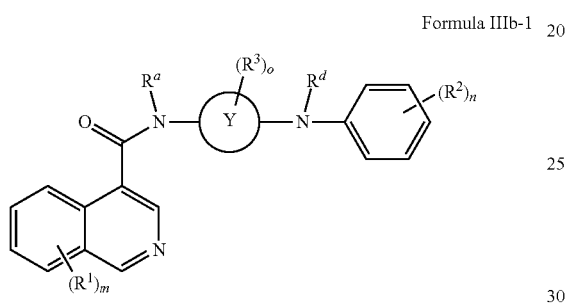

Formula IIIb-1 a tautomer thereof, a deuterated derivative of the compound or the tautomer, or a pharmaceutically acceptable salt of the foregoing; wherein:
- Y is $C_3$-$C_{10}$ cycloalkyl;
- $R^a$ and $R^d$, for each occurrence, are each independently hydrogen or $C_1$-$C_4$ alkyl;
- $R^1$, $R^2$, and $R^3$, for each occurrence, are each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)$NR^pR^q$, —$NR^pR^q$, —$NR^pC$(=O)$R^s$, —$NR^pC$(=O)$OR^s$, —$NR^pC$(=O)$NR^qR^r$, —$NR^pS$(=O)$_wR^s$, —$NO_2$, —$OR^s$, —OC(=O)$R^s$, —OC(=O)$OR^s$, —OC(=O)$NR^pR^q$, —S(=O)$_wR^s$, —S(=O)$_wNR^pR^q$, —$SO_3^-$, $C_3$-$C_{12}$ carbocyclyl, 3 to 12-membered heterocyclyl, phenyl, and 5 to 10-membered heteroaryl; wherein:
  - the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(=O)($C_1$-$C_6$ alkyl) are each optionally substituted with 1 to 3 groups selected from halogen, cyano, —C(=O)$R^s$, —C(=O)$OR^s$, —C(=O)$NR^pR^q$, —$NR^pR^q$, —$NR^pC$(=O)$R^s$, —$NR^pC$(=O)$OR^s$, —$NR^pC$(=O)$NR^qR^r$, —$NR^pS$(=O)$_wR^s$, —$OR^s$, —OC(=O)$R^s$, —OC(=O)$OR^s$, —OC(=O)$NR^pR^q$, —S(=O)$_wR^s$, —S(=O)$_wNR^pR^q$, $C_3$-$C_6$ cycloalkyl, and phenyl that is optionally substituted with 1 to 3 halogen atoms;
  - the $C_3$-$C_{12}$ carbocyclyl, the 3 to 12-membered heterocyclyl, the phenyl, and the 5 to 10-membered heteroaryl of any one of $R^1$, $R^2$, and $R^3$ are each optionally substituted with 1 to 3 groups selected from halogen, cyano, $C_1$-$C_4$ alkyl, —$NR^pR^q$, and —$OR^s$;
- $R^p$, $R^q$, and $R^r$, for each occurrence, are each independently selected from hydrogen, $C_1$-$C_4$ alkyl, and $C_3$-$C_6$ cycloalkyl; wherein:
  - the $C_1$-$C_4$ alkyl of any one of $R^p$, $R^q$, and $R^r$ is optionally substituted with 1 to 3 groups selected from halogen, cyano, and —OH;
- $R^s$, for each occurrence, is each independently selected from hydrogen, $C_1$-$C_4$ alkyl, and $C_3$-$C_6$ cycloalkyl;
- w is an integer selected from 1 and 2; and
- $R^1$, for each occurrence, may be attached to any of the ring atoms of the isoquinoline in formula IIIb-1, as long as valency permits;
- m is an integer selected from 0, 1, 2, 3, 4, 5, and 6;
- n is an integer selected from 1, 2, 3, 4, and 5; and
- is an integer selected from 0 and 1.

5. The compound according to claim 4, wherein the compound is of the following structural formula IVb-1:

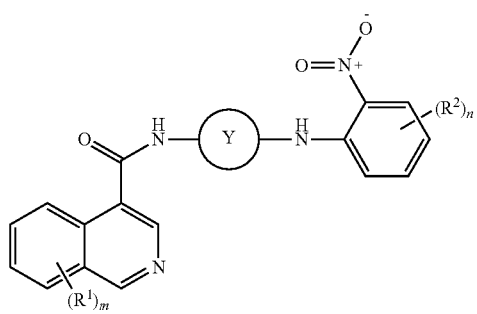

Formula IVb-1 a tautomer thereof, a deuterated derivative of the compound or the tautomer, or a pharmaceutically acceptable salt of the foregoing; wherein:
- Y is $C_3$-$C_6$ cycloalkyl; and
- n is an integer selected from 1, 2, 3, and 4.

6. The compound, tautomer, deuterated derivative, or pharmaceutically acceptable salt according to claim 5, wherein Y is cyclohexyl.

7. A compound of the following structural formula IIIb-2:

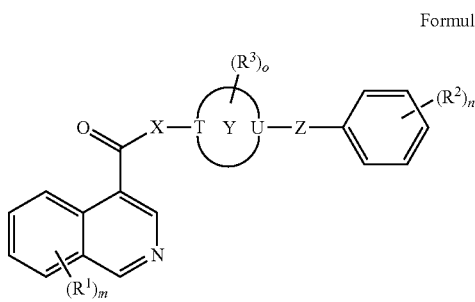

Formula IIIb-2 a tautomer thereof, a deuterated derivative of the compound or the tautomer, or a pharmaceutically acceptable salt of the foregoing; wherein:
- X is absent, and Z is —NH—, —[CH(CH($CH_3$)$_2$)]NH—, —C(=O)NHCH[(CONHCH$_3$)]CH$_2$—, or —CH($C_2H_5$)CH$_2$NH—; or
- X is —NH—, or —NHCH$_2$—, and Z is absent, —NH—, —[CH(CH($CH_3$)$_2$)]NH—, —C(=O)NHCH[(CONHCH$_3$)]CH$_2$—, or —CH($C_2H_5$)CH$_2$NH—;

Y is 3- to 10-membered heterocyclyl containing at least one N atom and optionally at least one other heteroatom selected from O and S;

at least one of T and U is N; and $R^1$ and $R^2$, for each occurrence, are each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)NR$^p$R$^q$, —NR$^p$R$^q$, —NR$^p$C(=O)R$^s$, —NR$^p$C(=O)R$^s$, —NR$^p$C(=O)NR$^q$R$^r$, —NR$^p$S(=O)$_w$R$^s$, —NO$_2$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, and —SO$_3^-$;

$R^3$, for each occurrence, is each independently selected from halogen, cyano, $C_1$-$C_6$ alkyl, $C_2$-$C_6$ alkenyl, $C_1$-$C_6$ alkoxy, —C(=O)($C_1$-$C_6$ alkyl), —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —NO$_2$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, —SO$_3$ and phenyl; wherein:

the $C_1$-$C_6$ alkyl, the $C_2$-$C_6$ alkenyl, and the $C_1$-$C_6$ alkoxy of any one of $R^1$, $R^2$, and $R^3$, and the $C_1$-$C_6$ alkyl of —C(=O)($C_1$-$C_6$ alkyl) are each optionally substituted with 1 to 3 groups selected from halogen, cyano, —C(=O)R$^s$, —C(=O)OR$^s$, —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, $C_3$-$C_6$cycloalkyl, and phenyl that is optionally substituted with 1 to 3 halogen atoms;

the phenyl of $R^3$ is each optionally substituted with 1 to 3 groups selected from halogen, cyano, and —OH;

$R^p$, $R^q$, and $R^r$, for each occurrence, are each independently selected from hydrogen, $C_1$-$C_4$ alkyl, and $C_3$-$C_6$ cycloalkyl; wherein:

the $C_1$-$C_4$ alkyl of any one of $R^p$, $R^q$, and $R^r$r is optionally substituted with 1 to 3 groups selected from halogen, cyano, and —OH;

$R^s$, for each occurrence, is each independently selected from hydrogen, $C_1$-$C_4$ alkyl, and $C_3$-$C_6$ cycloalkyl;

w is an integer selected from 1 and 2; and $R^1$, for each occurrence, may be attached to any of the ring atoms of the isoquinoline in formula IIIb-2, as long as valency permits;

m is an integer selected from 0, 1, 2, 3, 4, 5, and 6;

n is an integer selected from 1, 2, 3, and 4; and is an integer selected from 0, 1, and 2.

8. The compound, tautomer, deuterated derivative, or pharmaceutically acceptable salt according to claim 7, wherein:

X is absent, and Z is —NH—, —[CH(CH(CH$_3$)$_2$)]NH—, or C(=O)NHCH[(CONHCH$_3$)]CH$_2$—; or X is —NH—, or —NHCH$_2$—, and Z is absent, —NH—, —[CH(CH(CH$_3$)$_2$)]NH—, or C(=O)NHCH[(CONHCH$_3$)]CH$_2$—.

9. The compound according to claim 8, wherein the compound is of the following structural formula IVb-2:

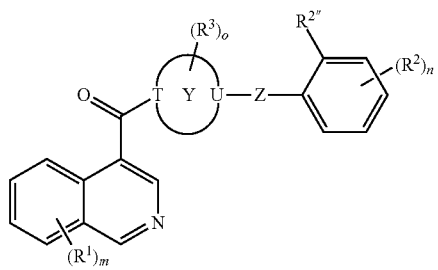

Formula IVb-2 a tautomer thereof, a deuterated derivative of the compound or the tautomer, or a pharmaceutically acceptable salt of the foregoing; wherein:

Y is 4- to 9-membered heterocyclyl containing at least one N atom and optionally at least one O atom;

at least one of T and U is N;

$R^{2'}$ is halogen, cyano, —NO$_2$, or —SO$_3^-$;

n is an integer selected from 1, 2, 3, and 4; and is an integer selected from 0 and 1.

10. The compound according to claim 9, wherein the compound is of the following structural formula Vb-2:

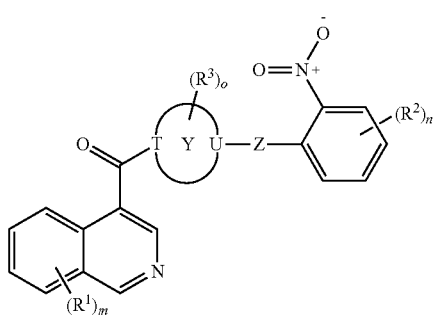

Formula Vb-2 a tautomer thereof, a deuterated derivative of the compound or the tautomer, or a pharmaceutically acceptable salt of the foregoing.

11. The compound, tautomer, deuterated derivative, or pharmaceutically acceptable salt according to claim 10, wherein Y is azetidinyl, piperidinyl, piperazinyl, 2,7-diazaspiro[4.4]nonanyl, octahydrocyclopenta[c]pyrrolyl, 2-oxa-6-azaspiro[3.4]octanyl, or octahydro-1H-isoindolyl.

12. A compound of the following structural formula IIIc:

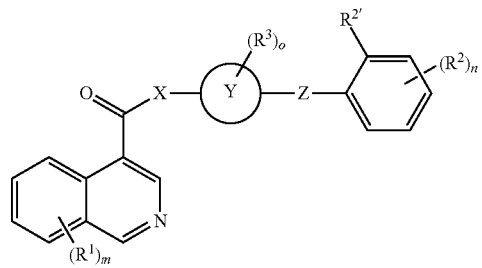

Formula IIIc a tautomer thereof, a deuterated derivative of the compound or the tautomer, or a pharmaceutically acceptable salt of the foregoing; wherein:

X is absent, —NH—, or —NHCH$_2$—;

Y is C$_3$-C$_{12}$ carbocyclyl, azetidinyl, piperidinyl, piperazinyl, 2,7-diazaspiro[4.4]nonanyl, octahydrocyclopenta[c]pyrrolyl, 2-oxa-6-azaspiro[3.4]octanyl, or octahydro-1H-isoindolyl; wherein the C$_3$-C$_{12}$ carbocyclyl of Y, the azetidinyl, piperidinyl, piperazinyl, 2,7-diazaspiro[4.4]nonanyl, octahydrocyclopenta[c]pyrrolyl, 2-oxa-6-azaspiro[3.4]octanyl, or octahydro-1H-isoindolyl of Y are each substituted with o groups of R$^3$;

Z is absent, —NH—, —[CH(CH(CH$_3$)$_2$)]NH—, C(=O)NHCH[(CONHCH$_3$)]CH$_2$— or —CH(C$_2$H$_5$)CH$_2$NH—;

R$^{2'}$ is cyano, —NO$_2$, or —SO$_3^-$;

wherein:

R$^1$ and R$^2$, for each occurrence, are each independently selected from halogen, cyano, C$_1$-C$_6$ alkyl, C$_2$-C$_6$ alkenyl, C$_1$-C$_6$ alkoxy, —C(=O)(C$_1$-C$_6$ alkyl), —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —NO$_2$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, and —SO$_3^-$;

R$^3$, for each occurrence, is each independently selected from halogen, cyano, C$_1$-C$_6$ alkyl, C$_2$-C$_6$ alkenyl, C$_1$-C$_6$ alkoxy, —C(=O)(C$_1$-C$_6$ alkyl), —C(=O)NR$^p$R$^q$, —NR$^p$R$^q$, —NR$^p$C(=O)R$^s$, —NR$^p$C(=O)OR$^s$, —NR$^p$C(=O)NR$^q$R$^r$, —NR$^p$S(=O)$_w$R$^s$, —NO$_2$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, —SO$_3$ and phenyl; wherein:

the C$_1$-C$_6$ alkyl, the C$_2$-C$_6$ alkenyl, and the C$_1$-C$_6$ alkoxy of any one of R$^1$, R$^2$, and R$^3$ and the C$_1$-C$_6$ alkyl of —C(=O)(C$_1$-C$_6$ alkyl) are each optionally substituted with 1 to 3 groups selected from halogen, cyano, —C(=O)R$^S$, —C(=O)OR$^s$, —C(=O)NR$^p$R$^q$, —NR$^p$R$^q$, —NR$^p$C(=O)R$^s$, —NR$^p$C(=O)OR$^s$, —NR$^p$C(=O)NR$^p$R$^r$, —NR$^p$S(=O)$_w$R$^s$, —OR$^s$, —OC(=O)R$^s$, —OC(=O)OR$^s$, —OC(=O)NR$^p$R$^q$, —S(=O)$_w$R$^s$, —S(=O)$_w$NR$^p$R$^q$, C$_3$-C$_6$ cycloalkyl, and phenyl that is optionally substituted with 1 to 3 halogen atoms;

the phenyl of R$^3$ is each optionally substituted with 1 to 3 groups selected from halogen, cyano, and —OH;

R$^p$, R$^q$, and R$^r$, for each occurrence, are each independently selected from hydrogen, C$_1$-C$_4$ alkyl, and C$_3$-C$_6$ cycloalkyl; wherein:

the C$_1$-C$_4$ alkyl of any one of R$^p$, R$^q$, and R$^r$ is optionally substituted with 1 to 3 groups selected from halogen, cyano, and —OH;

R$^s$, for each occurrence, is each independently selected from hydrogen, C$_1$-C$_4$ alkyl, and C$_3$-C$_6$ cycloalkyl;

w is an integer selected from 1 and 2; and

R$^1$, for each occurrence, may be attached to any of the ring atoms of the isoquinoline in formula IIIc, as long as valency permits;

m is an integer selected from 0, 1, 2, 3, 4, 5, and 6;

is an integer selected from 0, 1, 2, and 3; and n is an integer selected from 1, 2, 3, and 4.

13. The compound according to claim 12, wherein the compound is of the following structural formula IVc:

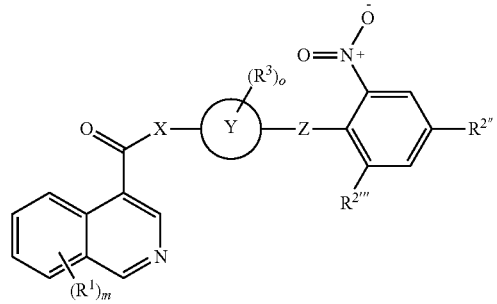

Formula IVc a tautomer thereof, a deuterated derivative of the compound or the tautomer, or a pharmaceutically acceptable salt of the foregoing; wherein:

R$^{2''}$ is halogen or C$_1$-C$_4$ alkyl; and

R$^{2'''}$ is —C(=O)NR$^p$R$^q$; wherein:

R$^p$ and R$^q$ are each independently hydrogen or C$_1$-C$_4$ alkyl.

14. The compound, tautomer, deuterated derivative, or pharmaceutically acceptable salt according to claim 13, wherein:

R$^{2''}$ is F, Cl, Br or C$_1$-C$_2$ alkyl; and

R$^{2'''}$ is —C(=O)NR$^p$R$^q$; wherein:

R$^p$ and R$^q$ are each independently hydrogen or C$_1$-C$_2$ alkyl.

15. The compound, tautomer, deuterated derivative, or pharmaceutically acceptable salt according to claim 14, wherein:

R$^{2''}$ is Br or —CH$_3$; and

R$^{2'''}$ is —C(=O)NHCH$_3$.

16. The compound, tautomer, deuterated derivative, or pharmaceutically acceptable salt according to claim 15, wherein R$^1$, for each occurrence, is independently selected from halogen, cyano, C$_1$-C$_4$ alkyl, C$_1$-C$_4$ alkoxy, —C(=O)(C$_1$-C$_4$ alkyl), —C(=O)NR$^p$R$^q$, —NR$^p$R$^q$, and —OR$^s$; wherein:

the C$_1$-C$_4$ alkyl and the C$_1$-C$_4$ alkoxy of R$^1$ and the C$_1$-C$_4$ alkyl of —C(=O)(C$_1$-C$_4$ alkyl) are each optionally substituted with 1 to 3 groups selected from halogen, cyano, and —OR$^s$;

R$^p$ and R$^q$, for each occurrence, are each independently selected from hydrogen and C$_1$-C$_2$ alkyl; and R$^s$, for each occurrence, is independently selected from hydrogen and C$_1$-C$_2$ alkyl.

17. The compound, tautomer, deuterated derivative, or pharmaceutically acceptable salt according to claim 16, wherein R$^1$, for each occurrence, is independently selected from F, Cl, Br, C$_1$-C$_2$ alkyl, and —OR$^s$; wherein:

the C$_1$-C$_2$ alkyl of R$^1$ is optionally substituted is optionally substituted with 1 to 3 groups of halogen; and R$^s$, for each occurrence, is independently selected from hydrogen and C$_1$-C$_2$ alkyl.

18. The compound, tautomer, deuterated derivative, or pharmaceutically acceptable salt according to claim 16, wherein R$^1$, for each occurrence, is independently selected from F and —OH.

19. The compound, tautomer, deuterated derivative, or pharmaceutically acceptable salt according to claim 18, wherein R$^3$, for each occurrence, is independently selected from halogen, cyano, C$_1$-C$_4$ alkyl, C$_1$-C$_4$ alkoxy, —C(=O)(C$_1$-C$_4$ alkyl), —C(=O)NR$^p$R$^q$, —NR$^p$R$^q$, —OR$^s$, and phenyl; wherein:
  the C$_1$-C$_4$ alkyl and the C$_1$-C$_4$ alkoxy of R$^3$ and the C$_1$-C$_4$ alkyl of —C(=O)(C$_1$-C$_4$ alkyl) are each optionally substituted with 1 to 3 groups selected from halogen, cyano, —OR$^s$, and phenyl that is optionally substituted with 1 to 3 halogen atoms;
  the phenyl of R$^3$ is optionally substituted with 1 to 3 groups selected from halogen, cyano, and C$_1$-C$_2$ alkyl;
  R$^p$ and R$^q$, for each occurrence, are each independently selected from hydrogen and C$_1$-C$_2$ alkyl; and
  R$^s$, for each occurrence, is independently selected from hydrogen and C$_1$-C$_2$ alkyl.

20. The compound, tautomer, deuterated derivative, or pharmaceutically acceptable salt according to claim 19, wherein R$^3$, for each occurrence, is independently selected from F, Cl, Br, C$_1$-C$_2$ alkyl, —OR$^s$, and phenyl; wherein:
  the C$_1$-C$_2$ alkyl of R$^3$ is optionally substituted is optionally substituted with 1 to 3 groups selected from halogen, cyano, and phenyl that is optionally substituted with 1 to 3 halogen atoms; and
  R$^s$, for each occurrence, is independently selected from hydrogen and C$_1$-C$_2$ alkyl.

21. The compound, tautomer, deuterated derivative, or pharmaceutically acceptable salt according to claim 20, wherein R$^3$, for each occurrence, is independently selected from —OH, phenyl and 2,4-dichloro-1-methylbenzene.

22. The compound, tautomer, deuterated derivative, or pharmaceutically acceptable salt according to claim 21, wherein R$^2$, for each occurrence, is independently selected from halogen, cyano, C$_1$-C$_4$ alkyl, C$_1$-C$_4$ alkoxy, —C(=O)(C$_1$-C$_4$ alkyl), —C(=O)NR$^p$R$^q$, —NR$^p$R$^q$, —NO$_2$, —OR$^s$, and —SO$_3^-$; wherein:
  the C$_1$-C$_4$ alkyl and the C$_1$-C$_4$ alkoxy of R$^2$ and the C$_1$-C$_4$ alkyl of —C(=O)(C$_1$-C$_4$ alkyl) are each optionally substituted with 1 to 3 groups selected from halogen, cyano, and —OR$^s$;
  R$^p$ and R$^q$, for each occurrence, are each independently selected from hydrogen and C$_1$-C$_2$ alkyl; and
  R$^s$, for each occurrence, is independently selected from hydrogen and C$_1$-C$_2$ alkyl.

23. The compound, tautomer, deuterated derivative, or pharmaceutically acceptable salt according to claim 22, wherein R$^2$, for each occurrence, is independently selected from F, Cl, Br, cyano, C$_1$-C$_2$ alkyl, —C(=O)NR$^p$R$^q$, —NO$_2$, —OR$^s$, and —SO$_3^-$; wherein:
  the C$_1$-C$_2$ alkyl of R$^2$ is optionally substituted with 1 to 3 groups of halogen;
  R$^p$ and R$^q$, for each occurrence, are each independently selected from hydrogen and —CH$_3$; and
  R$^s$, for each occurrence, is independently selected from hydrogen and C$_1$-C$_2$ alkyl.

24. The compound, tautomer, deuterated derivative, or pharmaceutically acceptable salt according to claim 23, wherein R$^2$, for each occurrence, is independently selected from Br, —CH$_3$, —C(=O)NHCH$_3$, —NO$_2$, and —SO$_3^-$.

25. The compound, tautomer, deuterated derivative, or pharmaceutically acceptable salt according to claim 21, wherein R$^2$, for each occurrence, is independently selected from halogen, cyano, C$_1$-C$_4$ alkyl, C$_1$-C$_4$ alkoxy, —C(=O)(C$_1$-C$_4$ alkyl), —C(=O)NR$^p$R$^q$, —NR$^p$R$^q$, and —OR$^s$; wherein:
  the C$_1$-C$_4$ alkyl and the C$_1$-C$_4$ alkoxy of R$^2$ and the C$_1$-C$_4$ alkyl of —C(=O)(C$_1$-C$_4$ alkyl) are each optionally substituted with 1 to 3 groups selected from halogen, cyano, and —OR$^s$;
  R$^p$ and R$^q$, for each occurrence, are each independently selected from hydrogen and C$_1$-C$_2$ alkyl; and
  R$^s$, for each occurrence, is independently selected from hydrogen and C$_1$-C$_2$ alkyl.

26. The compound, tautomer, deuterated derivative, or pharmaceutically acceptable salt according to claim 25, wherein R$^2$, for each occurrence, is independently selected from F, Cl, Br, cyano, C$_1$-C$_2$ alkyl, —C(=O)NR$^p$R$^q$, and —OR$^s$; wherein:
  the C$_1$-C$_2$ alkyl of R$^2$ is optionally substituted is optionally substituted with 1 to 3 groups of halogen;
  R$^p$ and R$^q$, for each occurrence, are each independently selected from hydrogen and —CH$_3$; and
  R$^s$, for each occurrence, is independently selected from hydrogen and C$_1$-C$_2$ alkyl.

27. The compound, tautomer, deuterated derivative, or pharmaceutically acceptable salt according to claim 26, wherein R$^2$, for each occurrence, is independently selected from Br, —CH$_3$, and —C(=O)NHCH$_3$.

28. The compound, tautomer, deuterated derivative, or pharmaceutically acceptable salt according to claim 1 wherein m is an integer selected from 0 and 1.

29. A compound selected from

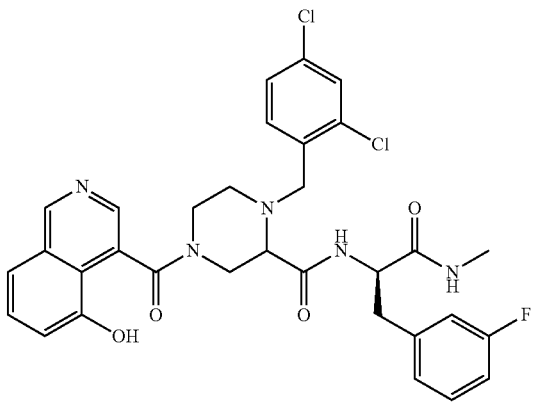

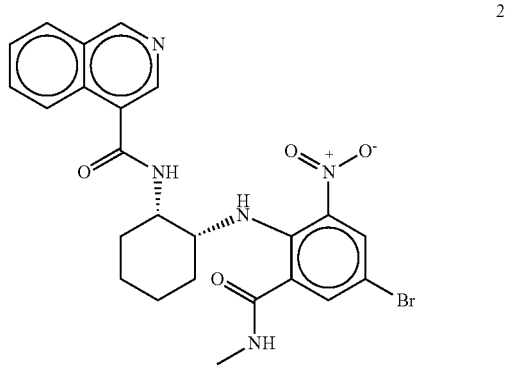

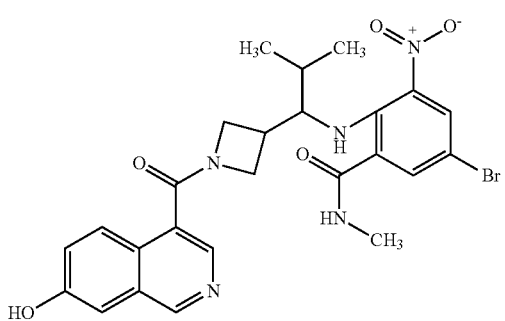
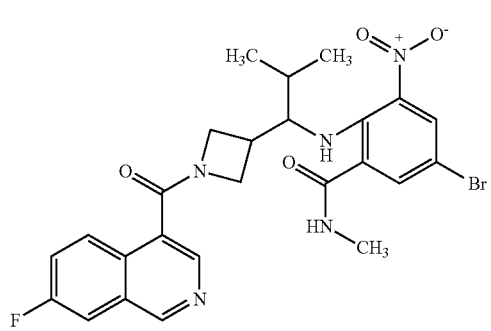
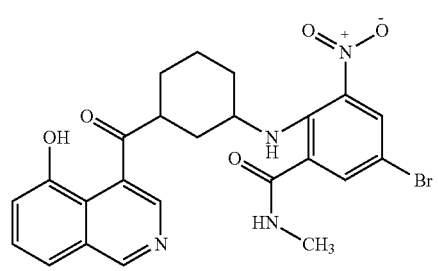
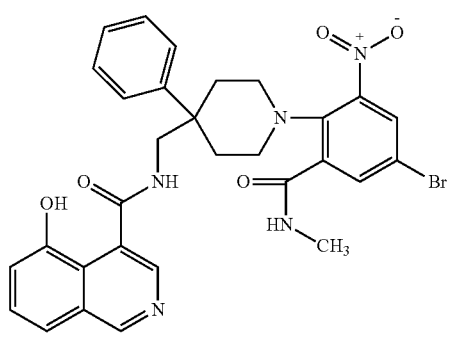
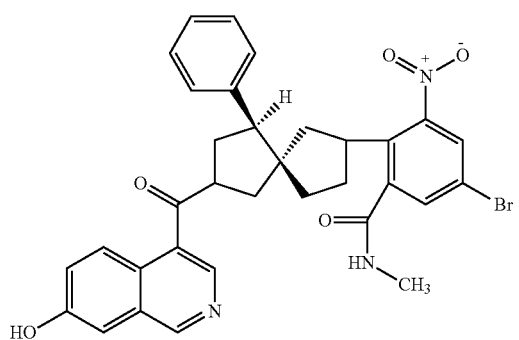
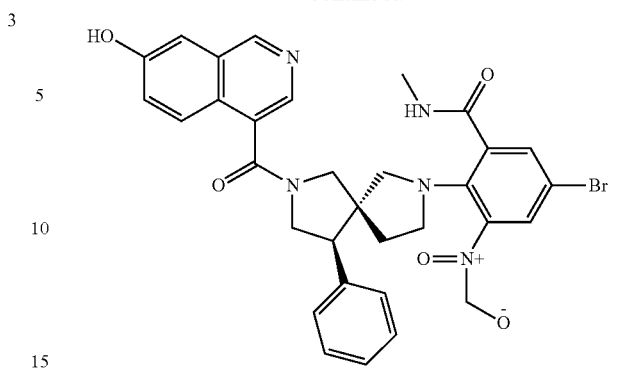
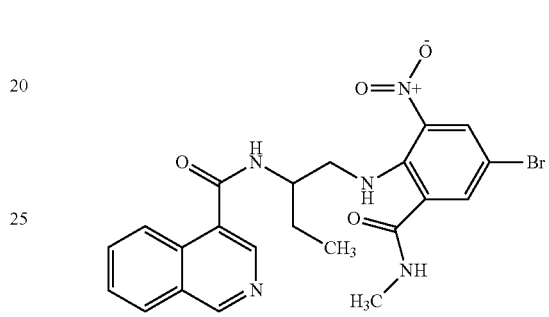
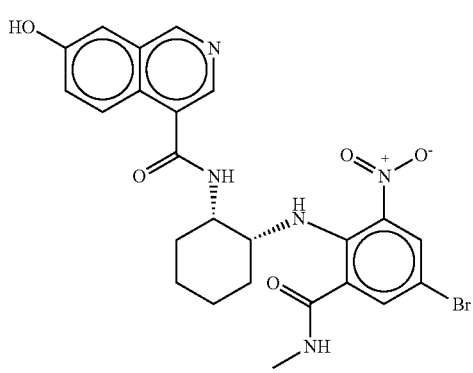
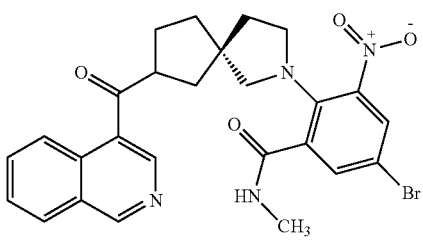
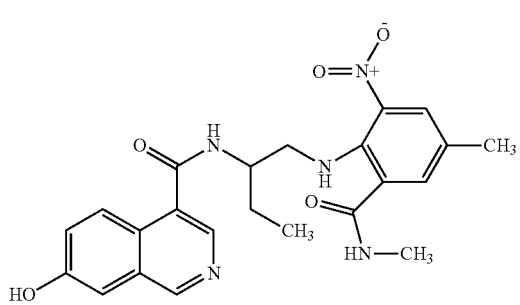

13
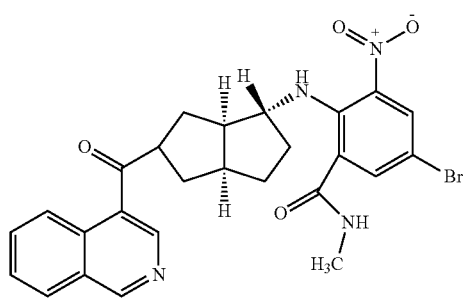
14
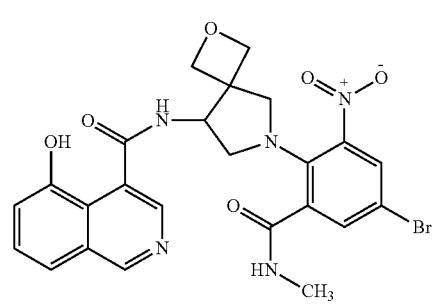
15
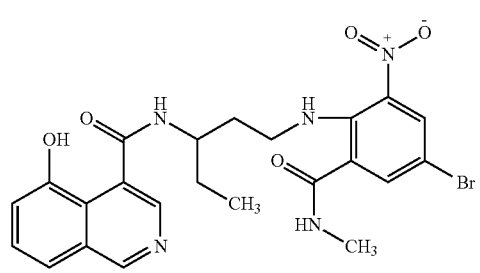
16
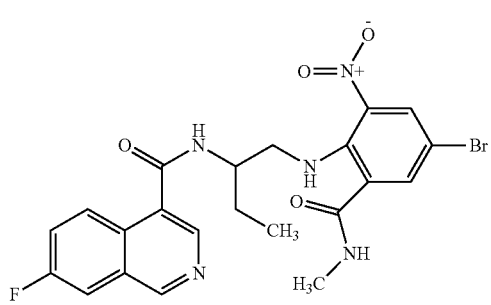
17
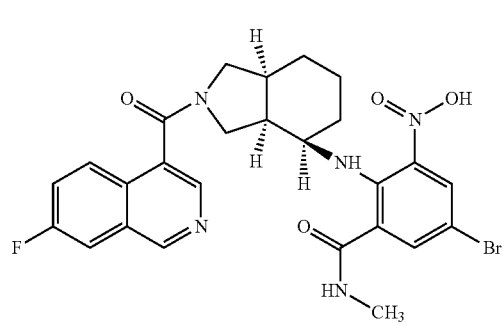
18
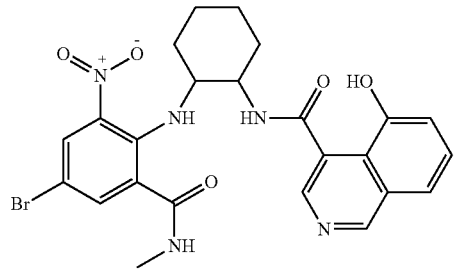 [SMILES: CNC(=O)c1cc(Br)cc([N+](=O)[O-])c1NC1CCCCC1NC(=O)c1cncc2cccc(O)c12]
19
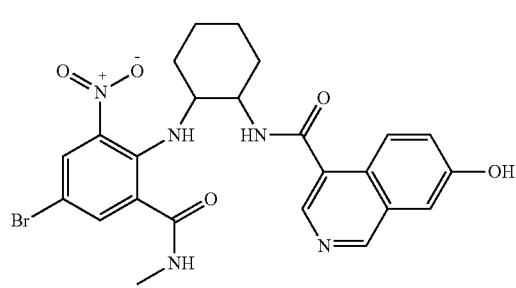 [SMILES: CNC(=O)c1cc(Br)cc([N+](=O)[O-])c1NC1CCCCC1NC(=O)c1cncc2cc(O)ccc12]
20
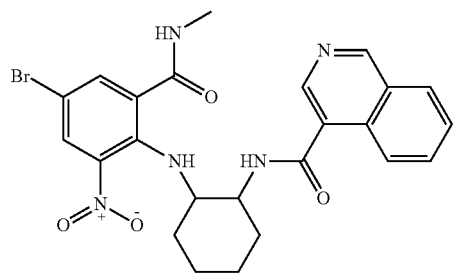
21
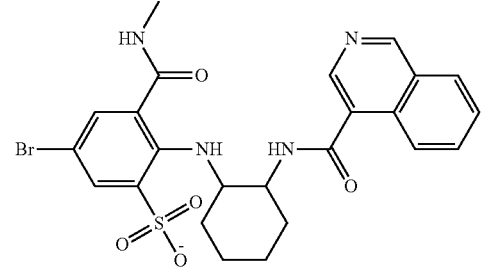 [SMILES: CNC(=O)c1cc(Br)cc(S(=O)(=O)[O-])c1NC1CCCCC1NC(=O)c1cncc2ccccc12]
22
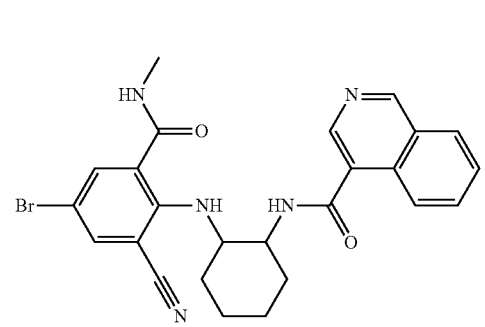 [SMILES: CNC(=O)c1cc(Br)cc(C#N)c1NC1CCCCC1NC(=O)c1cncc2ccccc12]

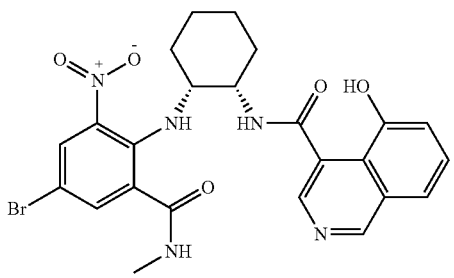 [SMILES: CNC(=O)c1cc(Br)cc([N+](=O)[O-])c1N[C@@H]1CCCC[C@@H]1NC(=O)c1cncc2cccc(O)c12]

a tautomer thereof, a deuterated derivative of the compound or tautomer, or a pharmaceutically acceptable salt of the foregoing.

30. A pharmaceutical composition comprising a compound according to claim 12 and at least one pharmaceutically acceptable carrier.

31. A method of treating a disease or a symptom of a disease caused by a coronavirus, comprising administering to a subject, a therapeutically effective amount of a compound according to claim 12.

32. The method according to claim 31, wherein the disease is a respiratory tract infectious disease.

33. The method according to claim 32, wherein the respiratory tract infectious disease is a severe acute respiratory syndrome.

34. The method according to claim 31, wherein the symptom is selected from fever or chills, cough, shortness of breath or difficulty in breathing, fatigue, muscle or body aches, headache, new loss of taste or smell, sore throat, congestion or runny nose, nausea or vomiting, diarrhea, persistent pain or pressure in the chest, new confusion, inability to wake or stay awake, bluish lips or face, and a combination thereof.

35. The method according to claim 31, wherein the coronavirus is severe acute respiratory syndrome coronavirus 2 (SARS-CoV-2).

36. A method of reducing or inhibiting the activity of a protease of a coronavirus, comprising contacting the protease with a compound according to claim 12.

37. The method according to claim 36, wherein the protease is a 3C-like protease.

38. The method according to claim 36, wherein the coronavirus is severe acute respiratory syndrome coronavirus 2 (SARS-CoV-2).

39. A method of reducing or inhibiting the replication of a coronavirus, contacting the coronavirus with a compound according to claim 12.

40. The method according to claim 39, wherein the coronavirus is severe acute respiratory syndrome coronavirus 2 (SARS-CoV-2).

* * * * *